(12) United States Patent
Boling

(10) Patent No.: US 8,694,130 B2
(45) Date of Patent: Apr. 8, 2014

(54) REINFORCED SENSING AND STIMULATION LEADS AND USE IN DETECTION SYSTEMS

(75) Inventor: C. Lance Boling, San Jose, CA (US)

(73) Assignee: NeuroPace, Inc., Sunnyvale, CA (US)

( * ) Notice: Subject to any disclaimer, the term of this patent is extended or adjusted under 35 U.S.C. 154(b) by 1114 days.

(21) Appl. No.: 12/688,814

(22) Filed: Jan. 15, 2010

(65) Prior Publication Data

US 2010/0107408 A1  May 6, 2010

Related U.S. Application Data

(60) Division of application No. 11/467,853, filed on Aug. 28, 2006, now Pat. No. 7,672,736, and a continuation of application No. 10/123,891, filed on Apr. 15, 2002, now Pat. No. 7,146,222.

(51) Int. Cl.
*A61N 1/05* (2006.01)
(52) U.S. Cl.
USPC .............................. 607/122; 607/116; 29/746
(58) Field of Classification Search
USPC ............................................. 607/122; 29/746
See application file for complete search history.

(56) References Cited

U.S. PATENT DOCUMENTS

| 4,161,952 | A | * | 7/1979 | Kinney et al. ................ 607/122 |
| 4,559,951 | A | | 12/1985 | Dahl et al. |
| 4,664,120 | A | | 5/1987 | Hess |
| 4,917,104 | A | | 4/1990 | Rebell |
| 5,954,759 | A | | 9/1999 | Swoyer et al. |
| 6,016,449 | A | | 1/2000 | Fischell et al. |
| 6,083,216 | A | | 7/2000 | Fischer, Sr. |
| 6,473,639 | B1 | | 10/2002 | Fischell et al. |
| 6,580,949 | B1 | | 6/2003 | Tsuboi et al. |

OTHER PUBLICATIONS

Ajmone-Marsan, C., "Electrocorticography: Historical Comments on its Development and the Evolution of its Practical Applications," Electroencephalogr. Clin. Neurophysiol. Suppl. (1998) 48: 10-16.
Black, P.M. et al., "Cortical Mapping for Defining the Limits of Tumor Resection," Neurosurgery (1987) 20: 914-919.
Cooper, I.S., et al., "Effects of Cerebellar Stimulation of Epilepsy, the EEG and Cerebral Palsy in Man," Electroencephalogr. Clin. Neurophysiol. Suppl. (1978) 34: 349-354.

* cited by examiner

*Primary Examiner* — Kennedy Schaetzle
(74) *Attorney, Agent, or Firm* — Arent Fox LLP

(57) ABSTRACT

A reinforced medical electrical lead for neurological applications has a reinforced construction for resisting the detachment of electrodes and lead connection terminals, thereby improving the robustness of the lead and extending the life of the lead by reducing the likelihood that a further surgical procedure will be required to remove the lead for repair or replacement thereof. The present reinforced lead construction maintains the integrity of the electrical connection between the conductor and the respective electrode and lead connection terminal by incorporating several reinforcing features in the lead construction in contrast to conventional lead constructions where it is possible to pull the electrodes and lead connection terminals away from their contact points with relatively little force.

7 Claims, 33 Drawing Sheets

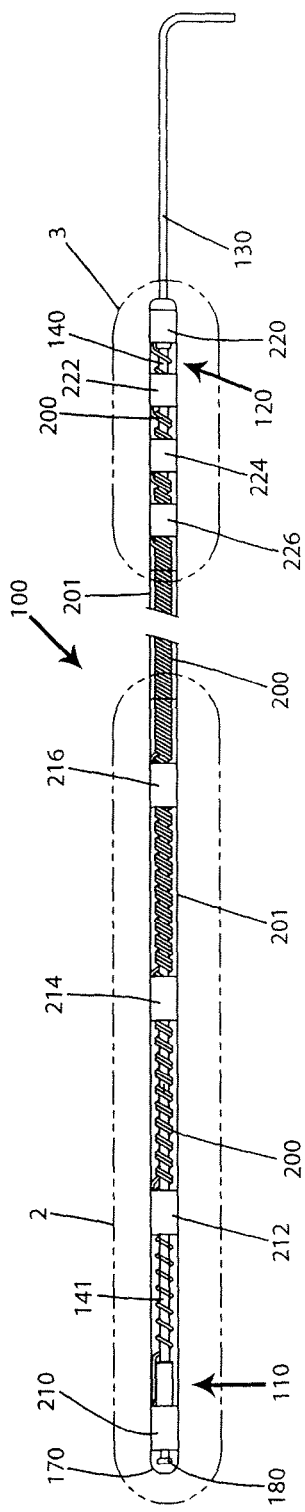
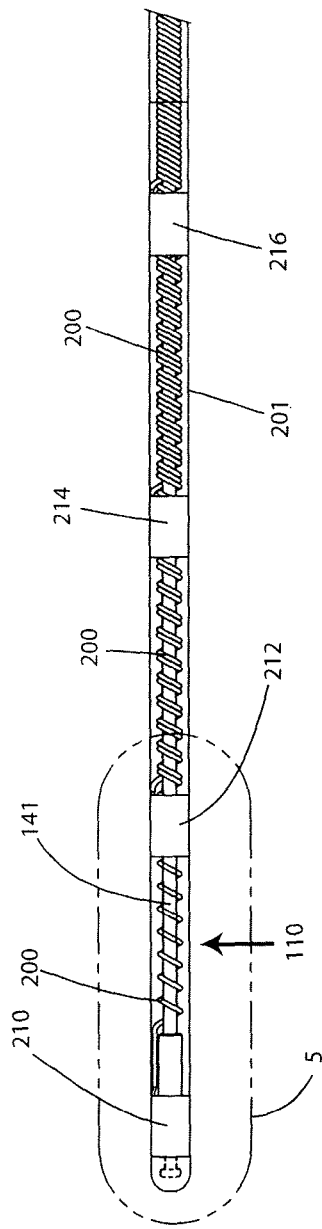
Fig. 1
Fig. 2

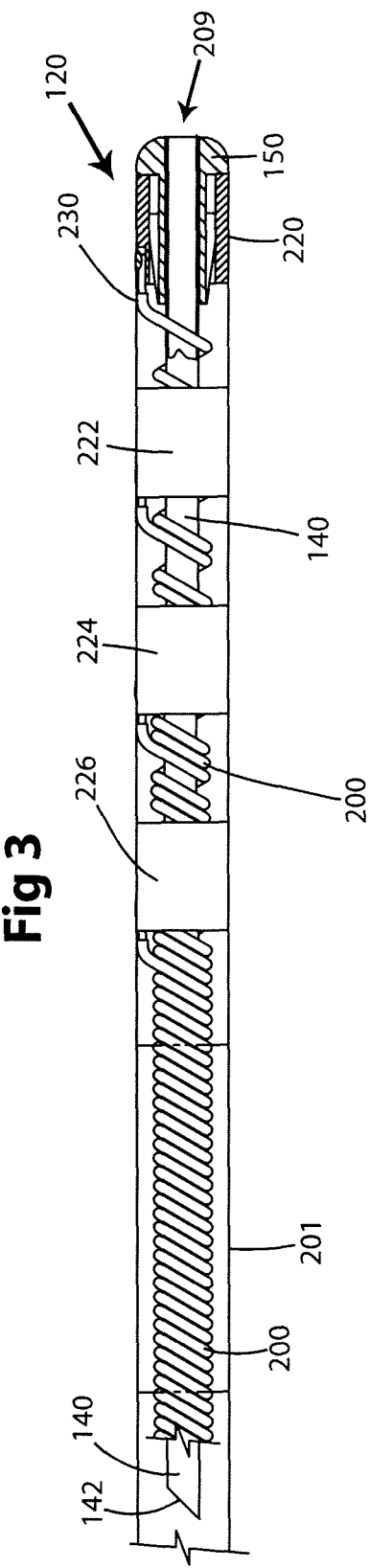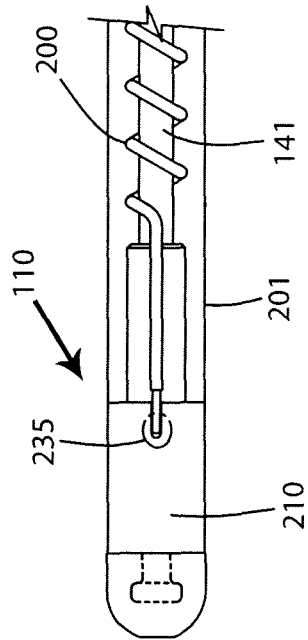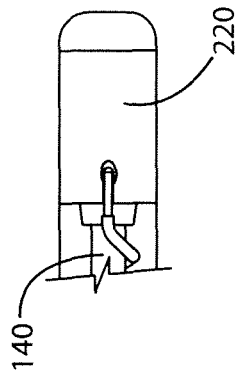

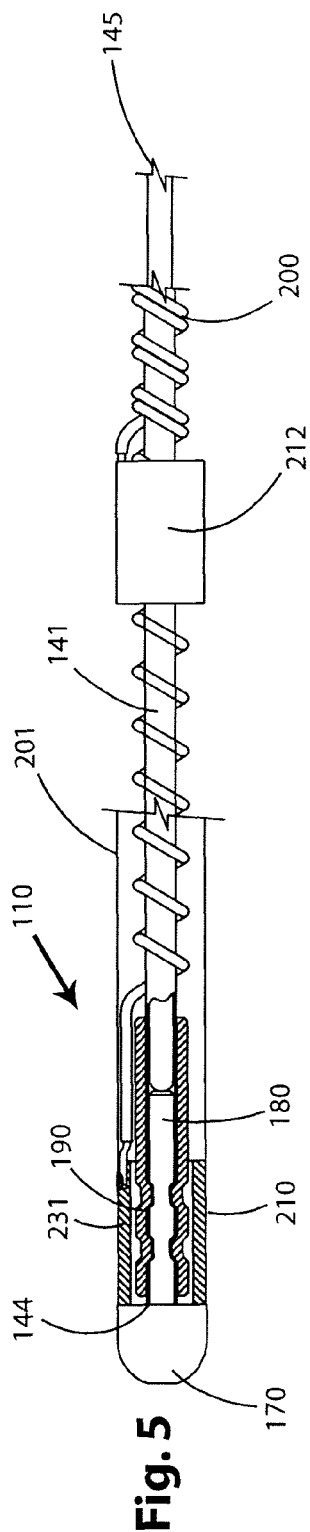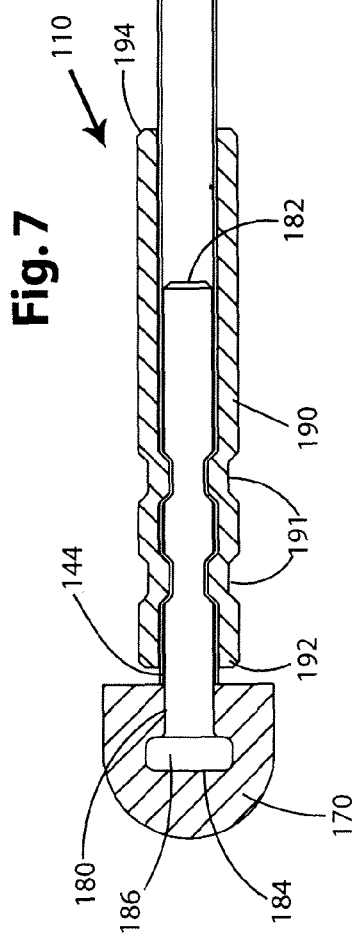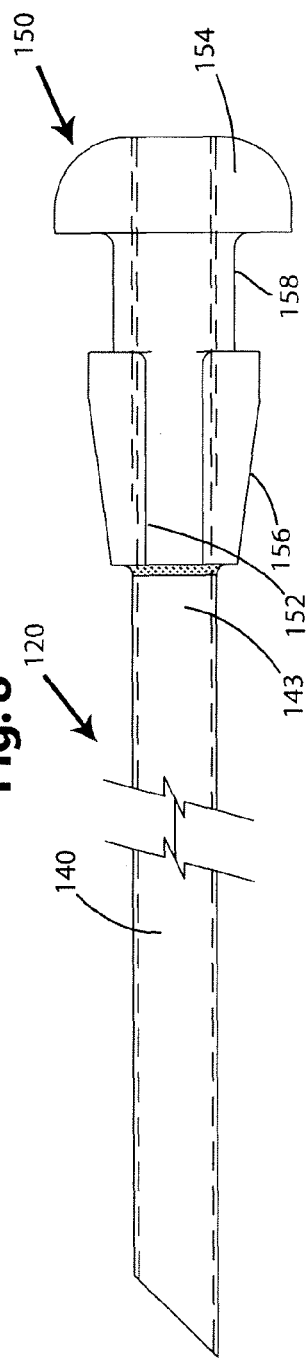

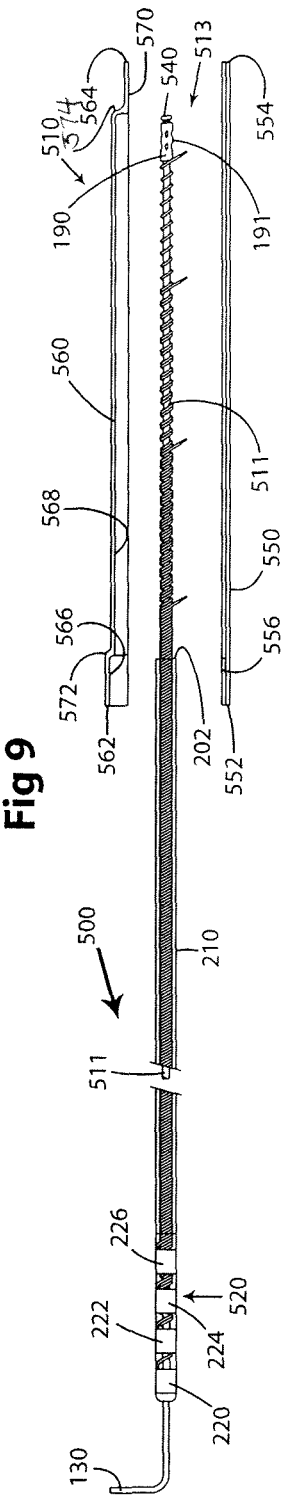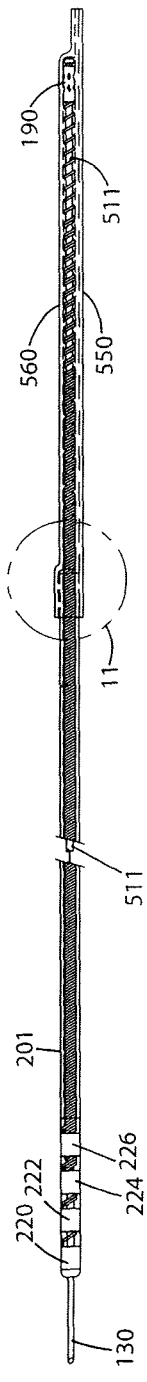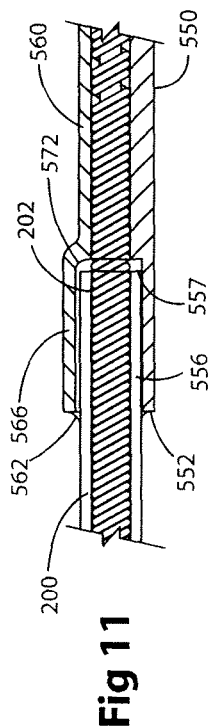
Fig 9
Fig 10
Fig 11

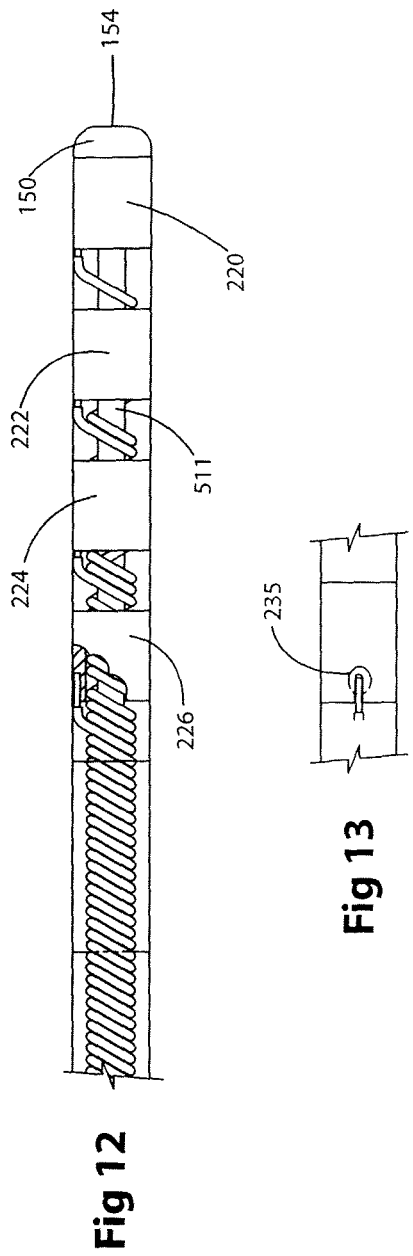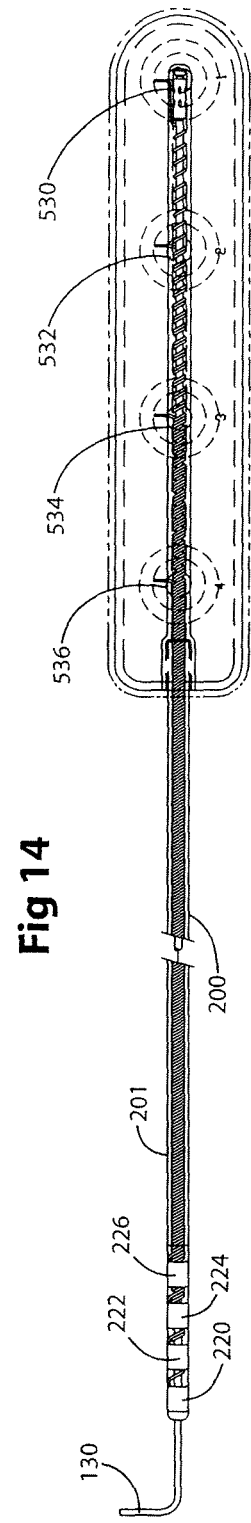

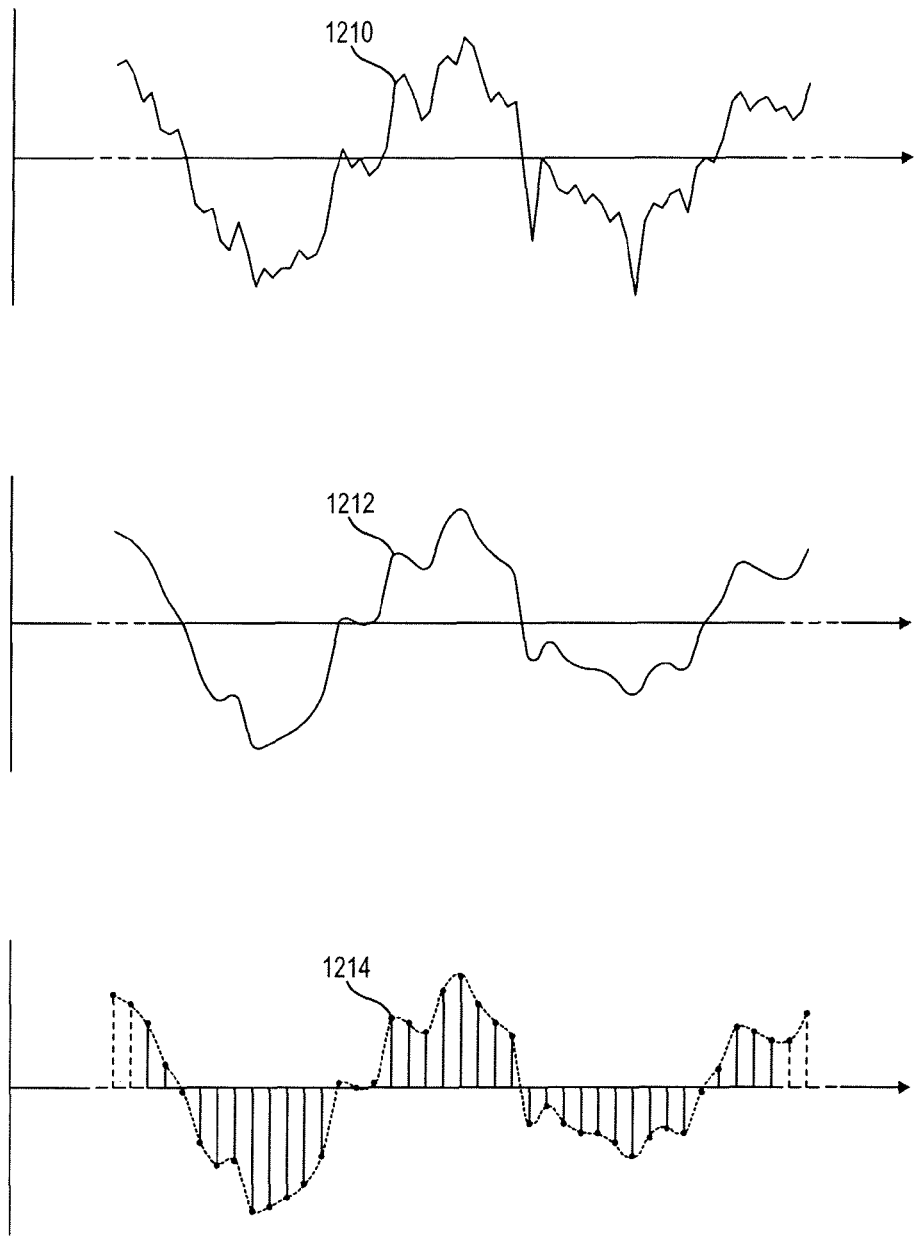

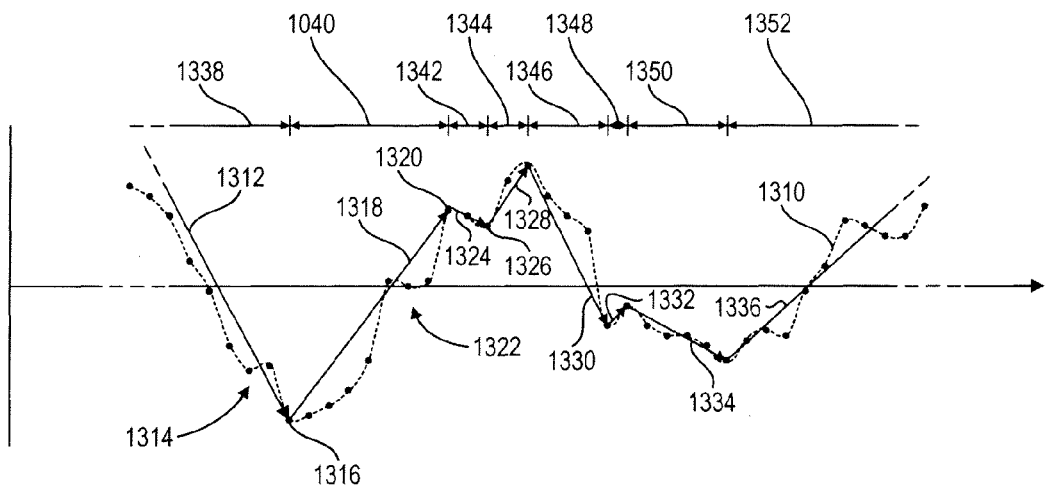
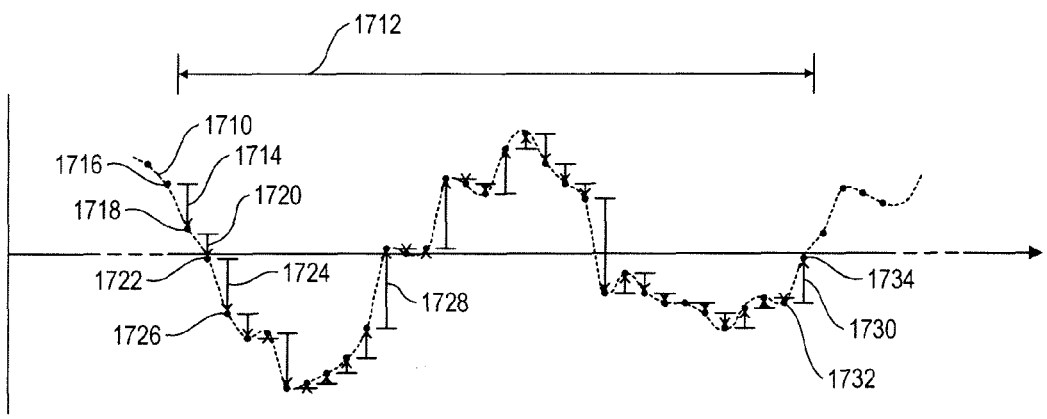
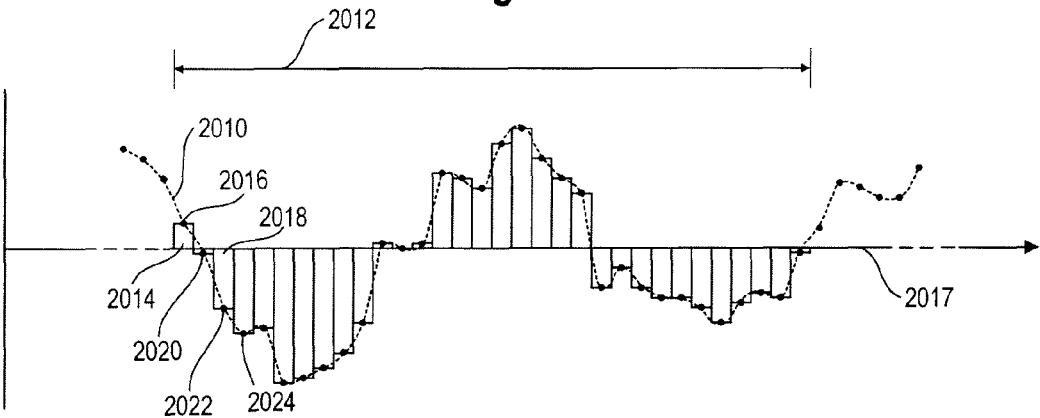

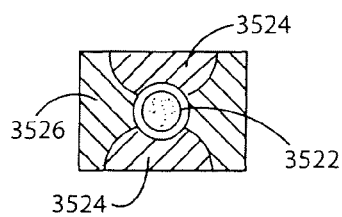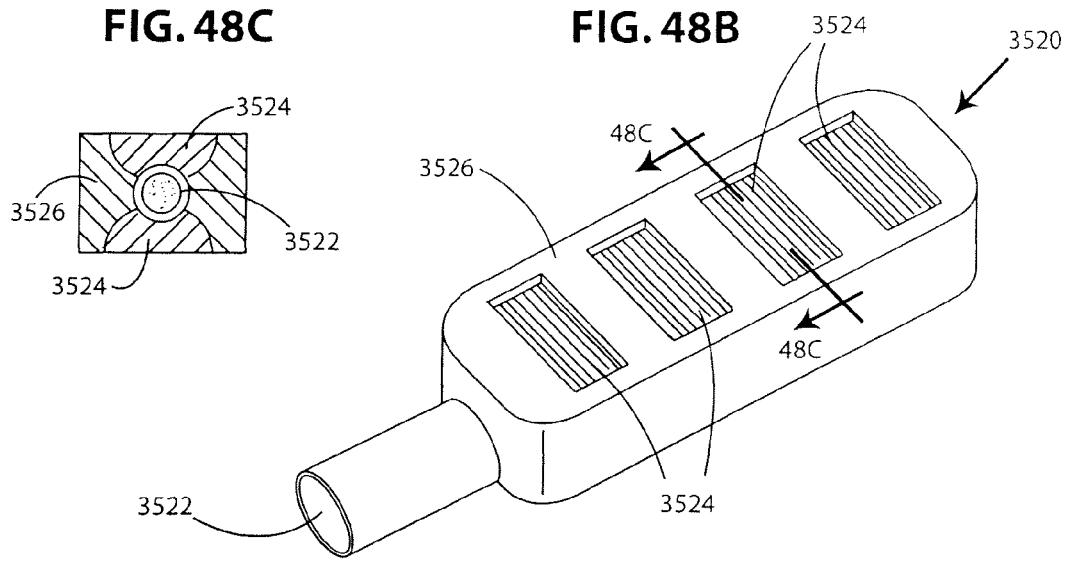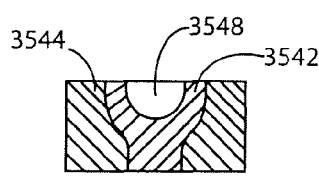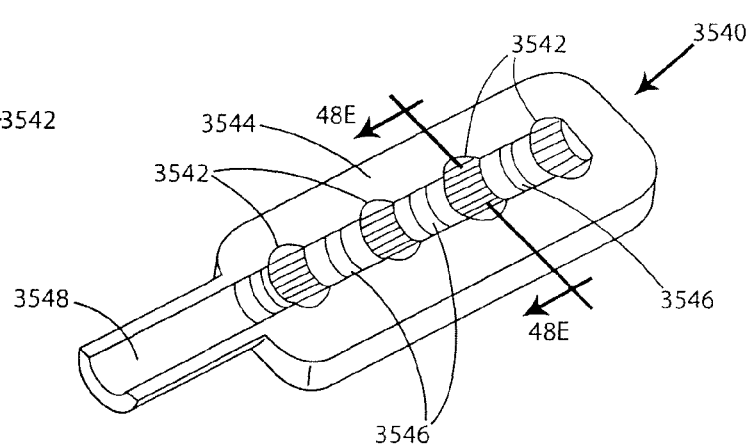

REINFORCED SENSING AND STIMULATION LEADS AND USE IN DETECTION SYSTEMS

CLAIM OF PRIORITY AND RELATED APPLICATIONS

This is a divisional of application Ser. No. 11 467,853, filed Aug. 28, 2006, now U.S. Pat. No. 7,672,736, which is a continuation of application Ser. No. 10 123,891, filed Apr. 15, 2002, now U.S. Pat. No. 7,146,222, each of which applications are incorporated by reference herein in the entirety.

NOT APPLICABLE

BACKGROUND

1. Technical Field

The present invention relates generally to implantable medical electrical leads, and more particularly to reinforced implantable depth and cortical medical electrical leads used to sense electrographic signals from a patient's brain or to apply electrical stimulation to the brain and to the use of the reinforced implantable medical electrical leads in a system for detecting neurological dysfunction.

2. Background

In the medical diagnosis and treatment of various brain disorders, including epilepsy, Parkinson's disease, sleep disorders, and psychiatric ailments, it is customary and frequently useful to analyze electrical signals originating in the brain. For a review of this technology, see Ajmone-Marsan, C. Electroarticography: Historical Comments on its Development and the Evolution of its Practical Applications, *Electroencephalogr. Clin. Neurophysiol. Suppl.* 1998, 48: 10-16; there are numerous applications. In common usage, the term "EEG" is often used to refer to signals representing aggregate neuronal activity potentials detectable via electrodes applied to a patient's scalp, though the term can also refer to signals obtained from deep in the patient's brain via depth electrodes and the like. Specifically, "EcoGs" refer to signals obtained from internal electrodes near the surface of the brain (generally on or under the dura mater); and EcoG is a particular type of EEG. Unless the context clearly and expressly indicates otherwise, the term "EEG" shall be used generically herein to refer to both EEG and EcoG signals, regardless of where in the patient's brain the electrodes are located.

It is also becoming accepted to apply electrical stimulation to various structures of the brain for both diagnostic and therapeutic purposes. For an exemplary diagnostic application, see Black, P. M. & Ronner S. F., "Cortical Mapping for Defining the Limits of Tumor Resection," *Neurosurgery* 1987, 20: 914-919, which addresses the use of electrical stimulation via deep brain electrodes to identify functional portions of the brain prior to and as a planning stage in surgical resection. For an example of a therapeutic application, see Cooper, I. S. & Upton, A. R. M., "Effects of Cerebellar Stimulation of Epilepsy, the EEG and Cerebral Palsy in Man," *Electroencephalogr. Clin. Neurophysiol. Suppl.* 1978, 34: 349-354. In both of these examples, acutely implanted brain electrodes are connected to external equipment.

It is also contemplated that chronic stimulation can be used as a direct treatment for disorders such as epilepsy. See, e.g., U.S. Pat. No. 6,016,449 to Fischell, et al., which describes an implantable neurostimulator that is coupled to relatively permanent deep brain electrodes.

Although it is frequently possible to employ scalp electrodes for certain types of EEG monitoring and analysis, it has been found that ambient electrical noise (such as from the 50/60 Hz power source) can adversely impact signal-to-noise ratio, and certain signal components of interest may be filtered out by the patient's intervening cranium and scalp tissue. Moreover, precise localization is less feasible with scalp electrodes.

Accordingly, intracranial signal analysis, that is, the consideration of signals that originate from a patient's cranium, whether by internal or external apparatus, is best accomplished with brain surfaces electrodes, such as strip and grid electrodes, cortical depth leads, or some combination of surface electrodes and depth leads.

Typical brain surface strip and grid electrodes arrays consist of flat, disc-shaped electrodes that are placed on the surface of the patient's brain. In a typical strip or grid electrode array, each electrode has an exposed diameter of approximately 3 mm (or ⅛ inch), and the electrodes are distributed along a line (for a strip electrode array) or in a rectangular grid (from a grid electrode array) at a pitch of approximately 10 mm.

Another disadvantage associated with conventional leads is that the construction of the leads is such that electrical contact between the conductor and the electrodes is often unsatisfactory as the electrical connection between the conductor and a respective electrode can fail. Further, the installation and normal positioning of the lead places stress on both the distal and proximal portions of the lead. One type of conventional implantable electrical lead consists of a 1 mm diameter silicon tube with a conductor element being disposed within the tube and extending a length thereof. The electrical lead includes electrodes (e.g., ring electrodes) at both distal and proximal ends of the tube. Each electrode is electrically connected to the conductor at a contact point to permit current to follow therebetween. During implantation and or use, the robustness of the electrical connection between the conductor and one or more electrodes can degrade or fail due to forces (i.e., stress) being applied to the distal and/or proximal ends of the lead. In other words, the electrodes can become dislodged from the conductor with relative ease, thereby causing the electrical connection to fail and also possibly causing the electrode to completely become dislodged from the lead. This is undesirable since it may result in the electrode being left in situ. This is an unsatisfactory result as it renders the electrical lead operating at less than optimal conditions and in order to repair the electrical lead, the electrical connection must be restored by repairing the electrical lead or by replacing the electrical lead with a different one. Both of these options are not very attractive since each requires additional surgery (with the associated risks for the patient).

Accordingly, it would be desirable to have an implantable medical electrical lead that provides improved electrical connection between the conductor and the electrodes spaced along the medical electrical lead and eliminates or reduces the likelihood that an electrode can become dislodged from the lead during implantation and/or use.

SUMMARY

A medical electrical lead having a reinforced construction is provided. The medical electrical lead is adapted to be at least partially implanted in a human patient and in one exemplary embodiment, the medical electrical lead is a depth lead, while in another embodiment, the medical electrical lead is a cortical lead. In the depth lead embodiment, the lead includes a proximal portion having a lead connection area and a distal portion having at least one electrode in communication with the lead connection area of the proximal portion via the at least one conductor. First and second longitudinal reinforcing members (e.g., stiffening sheaths) are provided with the first longitudinal reinforcing member being disposed at the proximal portion for enhancing the rigidity of the proximal portion and the second longitudinal reinforcing member being disposed at the distal portion for enhancing the rigidity of the distal portion. A body, such as a silicone shaft, is provided around the reinforcing element for interconnecting the proximal portion and the distal portion.

Each of the first and second reinforcing members is preferably a thin-walled polymeric reinforcing sheath defining a longitudinal lumen and providing a structure around which the conductor can be arranged. The at least one conductor is adapted to be arranged around (e.g., in a helical manner) the first and second reinforcing sheaths and in one embodiment, the at least one conductor has a medial section which is a coiled section that does not have either the first or second reinforcing sheath disposed therethrough.

The distal portion of the lead includes a core member at least partially inserted into the longitudinal lumen defined by the first reinforcing sheath and a reinforcing sleeve is disposed around the first reinforcing sheath such that the sleeve surrounds at least the portion of the core member inserted into the first reinforcing sheath. The reinforcing sleeve is then crimped around the first reinforcing sheath and the inserted core member to thereby enhance the structural rigidity of the distal portion.

In another exemplary embodiment, the distal portion includes a lower electrode strip having at least one electrode in communication with a lead connection area of the proximal portion by way of at least one conductor and also includes a cover that mates with the lower electrode strip to enclose at least a portion of a reinforcing sheath in the distal portion. As in the other embodiments, the reinforcing sheath defines a longitudinal lumen and also provides a structure around which the at least one conductor can be arranged. The reinforcing sheath also provides enhanced structural rigidity to the distal portion.

The proximal portion of the lead preferably includes a bushing that is coupled to one end of the second reinforcing sheath. The bushing has a bore formed therethrough to provide access for a stylet into the longitudinal lumen defined by the second longitudinal lumen defined by the second reinforcing sheath and the body of the lead. The proximal portion is reinforced by disposing a proximal reinforcing element around the bushing. In one exemplary embodiment, the bushing is wrapped with a non-absorbable fibrous suture stock (e.g., polyester fibers configured as a twisted cable). The twisted fibrous cable is positioned to help hold the lead connection terminal in place and also, due to its construction, it resists any disruptive forces that may be applied to the lead at the proximal portion thereof, thereby ensuring that the lead connection terminal remains in place and the integrity of the electrical connection between the conductor and the lead connection terminal is maintained.

Accordingly, in comparison to traditional strip and grid electrode arrays, the present reinforced medical lead has a reinforced construction that resists the detachment of the electrodes and lead connection terminals and also improves the robustness of the lead, thereby extending the life of the lead and reducing the likelihood that a further surgical procedure will be required to remove the lead for repair or replacement thereof. The present reinforced lead construction maintains the integrity of the electrical connection between the conductor and the respective electrode and the lead connection terminal in contrast to conventional lead constructions where the electrodes and lead connection terminals can become dislodged, thereby breaking their contact points upon the application of relatively little force. This is accomplished by incorporating reinforcing members into the lead construction, whereby the reinforcing members disperse the normal stress that is observed in the distal and proximal portions of the lead. Unlike conventional leads where stress is localized in the distal and proximal portions, the reinforcing members of the present lead disperse the stress over a greater longitudinal surface of the lead, thereby eliminating or greatly reducing the likelihood that the electrodes can become dislodged from the lead body or otherwise damaged to a degree where the electrical connection is broken. This results in a much more robust medical electrical lead being provided.

Other features and advantages of the present invention will be apparent from the following detailed description when read in conjunction with the accompanying drawings.

BRIEF DESCRIPTION OF THE DRAWINGS

The foregoing and other features of the present invention will be more readily apparent from the following detailed description and drawings of illustrative embodiments of the invention in which:

FIG. 1 is a schematic sectional view of an exemplary reinforced lead according to one embodiment;

FIG. 2 is an enlarged sectional detail view taken from ellipse 2 of FIG. 1 illustrating a distal portion of the reinforced lead;

FIG. 3 is an enlarged sectional detail view taken from ellipse 3 of FIG. 1 illustrating a proximal portion of the reinforced lead;

FIG. 4 is a sectional view of the proximal portion of FIG. 3 illustrating a connection between a conductor and a contact;

FIG. 5 is an enlarged sectional detail view taken from ellipse 5 of FIG. 2;

FIG. 6 is a top plan view in partial section of the distal portion of FIG. 2 illustrating a connection between a conductor and an electrode;

FIG. 7 is a sectional view of the distal portion of FIG. 2;

FIG. 8 is an elevational view of a bushing and a stiffening sheath that form a part of the proximal portion of FIG. 3;

FIG. 9 is an exploded schematic sectional view of an exemplary reinforced lead according to another embodiment;

FIG. 10 is a schematic sectional view of the reinforced lead of FIG. 9;

FIG. 11 is an enlarged sectional detail view taken from circle 11 of FIG. 10;

FIG. 12 is a schematic sectional view of the reinforced lead of FIG. 10 illustrating a proximal portion thereof;

FIG. 13 is a top plan view of a section of the proximal portion of FIG. 12 illustrating a connection between a conductor and a contact;

FIG. 14 is a bottom plan view of the reinforced lead of FIG. 9 in an assembled state;

FIG. 29 is a graph of an exemplary EEG signal, illustrating decomposition of the signal into time windows and samples;

FIG. 30 is a graph of the exemplary EEG signal of FIG. 29, illustrating the extraction of half waves from the signal;

FIG. 34 is a graph of the exemplary EEG signal of FIG. 29, illustrating the calculation of a line length function;

FIG. 37 is a graph of the exemplary EEG signal of FIG. 29, illustrating the calculation of an area function;

FIG. 48B is a perspective view of a variation of an interposer;

FIG. 48C is a cross-section of the interposer variation shown in FIG. 48B;

FIG. 48D is a perspective view of a variation of an interposer;

FIG. 48E is a cross-section of the interposer shown in FIG. 48D;

DETAILED DESCRIPTION

Figure 15:
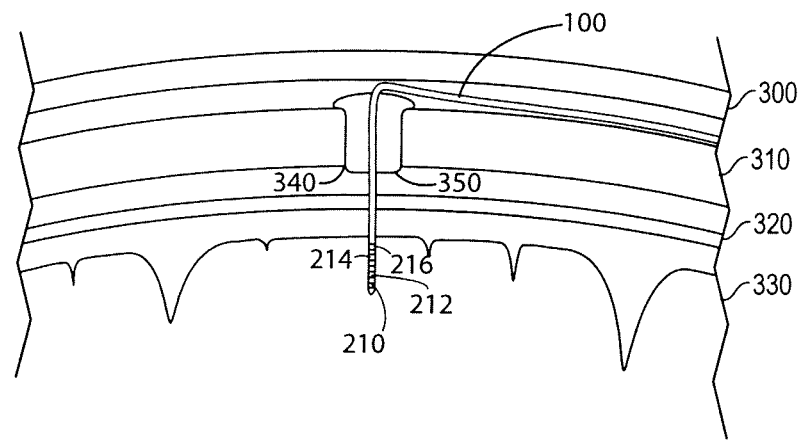
FIG. 15 is an illustration showing the use of the lead of FIG. 1 in an exemplary section of a patient's head, including the patient's brain, dura mater, and cranium.

Referring initially to FIG. 1, an exemplary implantable reinforced medical electrical lead 100 according to one embodiment is illustrated. The lead 100 is an elongated structure having a distal portion 110 and an opposing proximal portion 120. Generally, the lead 100 is flexible, and as described in further detail below, is fabricated to include a body (e.g., flexible shaft 201) formed of a biocompatible elastomer, such as silicone, urethane, or any of a number of suitable biocompatible materials. A stylet 130 is received within the lead 100 for providing additional rigidity to the lead to assist in the movement and placement of the lead 100 into the patient's brain tissue, as will be described in further detail below.

Referring now to FIGS. 1 through 8, the lead 100 according to one embodiment includes a first reinforcing sheath (stiffening sheath) 140 at the proximal portion 120 and a second reinforcing sheath 141 at the distal portion 110. Each of the sheaths 140, 141 is a generally thin-walled tubular member that is of sufficient rigidity that it maintains its shape during use of the lead 100, while at the same time, each sheath 140, 141 is flexible so that it can assume different bent positions when the lead 100 is being positioned within the patient's brain. The sheaths 140, 141 act as stiffening members, as will be described in detail below, in that the sheaths 140, 141 provide additional rigidity to the lead 100. The reinforcing sheaths 140, 141 can be formed of any number of materials that are suitable for the intended use. For example, the reinforcing sheaths 140, 141 can be formed of a polymeric material that can be formed into a thin wall structure and in one exemplary embodiment, the reinforcing sheaths 140, 141 are formed of polyimide. While the reinforcing sheaths 140, 141 are described as each having a tubular shape, it will be understood that the reinforcing sheaths 140, 141 can have any number of different shapes.

The first reinforcing sheath 140 serves as a proximal reinforcing member and has an end 142 that is disposed within the interior of the lead 100 away from the proximal lead end and an opposing end 143 that is disposed near the proximal end of the proximal portion 120 of the lead 100. In one exemplary embodiment, the first reinforcing sheath 140 has a length of about 1 inch. The first reinforcing sheath 140 serves to receive the stylet 130 within a longitudinal lumen that is defined by the body of the reinforcing sheath 140. Accordingly, the dimensions of the first reinforcing sheath 140 should be sufficient to accommodate the stylet 130 within the longitudinal lumen. As shown in FIGS. 3 and 8, the end 143 of the first reinforcing sheath 140 is securely coupled to a bushing 150 using conventional techniques. For example, a frictional fit may be provided between the bushing 150 and the first reinforcing sheath 140 by disposing the end 143 within a bore 152 formed through the bushing 150. The end 143 can also be coupled to the bushing 150 by applying a small amount of adhesive to the interface between the end 143 and the bushing 150, as shown in FIG. 8.

The bushing 150 has a head 154 at one end thereof and a tapered section 156 at the other end with the bore 152 extending through the bushing 150 from one end to the other end. A recessed section 158 (i.e., a radial groove) is formed between the tapered section 156 and the head 154. The bushing 150 is generally annular in shape and the bore 152 has dimensions that can accommodate the stylet 130 as it is introduced into the lead 100, and more particularly into the lumen of the first reinforcing sheath 140, by being inserted into and fed through the bore 152. In this embodiment, the recessed section 158 has an annular shape and the tapered section 156 is generally conically shaped with an inward taper toward the end of the bushing 150 opposite the head 154. The bushing 150 can be formed of any number of suitable bio-stable materials, including metals and plastics. In one exemplary embodiment, the bushing 150 is formed of platinum.

The other reinforcing sheath (i.e., the second reinforcing sheath 141) acts as a reinforcing member for the distal portion 110. In the illustrated exemplary embodiment, the lead 100 contains two separate reinforcing sheaths, namely the distal second reinforcing sheath 141 and the proximal first reinforcing sheath 140, which are disposed at opposite ends of the lead 100. Accordingly, the reinforcing sheath is not a continuous member that extends from the distal portion 110 to the proximal portion 120 but rather is formed in two discrete sections. However, it will be understood that in an alternative embodiment, the reinforcing sheath extends uninterrupted from the distal portion 110 to the proximal portion 120 and in this embodiment, only a single piece of reinforcing sheath is used to construct the lead 100.

As best shown in FIGS. 5 and 7, the distal reinforcing sheath 141 includes an end 144 and an opposing end 145. In one exemplary embodiment, the distal reinforcing sheath 141 is longer than the proximal reinforcing sheath 140 and has a length of approximately 2.25 inches. The end 144 of the second reinforcing sheath 141 extends to a distal tip 170 that is formed at the distal end of the distal portion 110 of the lead 100. As shown, the end 144 preferably does not extend into the distal tip 170 but is adjacent thereto. The distal portion 110 includes a core member 180 that is partially disposed within the lumen of the second reinforcing sheath 141.

The core member 180 is preferably a solid structure having a first end 182 and a second end 184 that terminates in a head 186. The first end 182 serves as a stop for the stylet 130 as it is fed through the lumen of the second reinforcing sheath 141 toward the distal end of the lead 100. The head 186 is arranged so that it is disposed beyond the end 144 of the second reinforcing sheath 141.

The core member 180 has an outer diameter that is slightly less than the inner diameter of the distal reinforcing sheath 141 to permit the core member 180 to be inserted a predetermined distance into the lumen of the second reinforcing sheath 141. While, the core member 180 is a solid structure that serves as a die (as will be described in greater detail hereinafter), the core member 180 is formed so that it slightly compresses and elongates slightly when subjected to a crimping force. The material which is used to form the core member 180 should be selected with this objective in mind. In one exemplary embodiment, the core member 180 is formed of a metal and in one specific embodiment, the core member 180 is formed of platinum.

In this embodiment, the distal tip 170 is generally dome-shaped and surrounds the head 186 of the core member 180. The distal tip 170 is a relatively rigid tip that represents the distal end of the lead 100 and is preferably formed from a relatively rigid biocompatible polymer and is coupled to the head 186 using any number of conventional methods. For example and according to one exemplary embodiment, the distal tip 170 is molded in place around the head 186 and in this embodiment, the distal tip 170 is formed of a polymeric material that lends itself to being used in a molding process for fabricating the distal tip 170 around the core member 180. In accordance with conventional molding techniques, the head 186 can be disposed within a mold cavity and the moldable polymeric material is introduced into the mold cavity around the head and is fabricated into the dome-shaped structure due to the shape of the mold cavity. In one exemplary embodiment, the distal tip 170 is a rigid plastic (bionate) tip. However, it will be appreciated that there are numerous materials for forming the distal tip 170 including various categories of polymers and plastics, such as polyester, polyimide, polyamide, polyetheretherketone (PEEK), and specific materials falling into those categories, such as nylon and aramid (e.g., Kevlar®).

The distal portion 110 of the lead 100 further includes a sleeve 190 that is disposed around a length of the second reinforcing sheath 141. More specifically, the sleeve 190 is formed of a material that can be crimped or otherwise compressed in selected regions so as to securely locate and hold other components in place at the distal portion 110. Prior to being compressed, the sleeve 190 is a tubular member with an inner channel extending therethrough for receiving the second reinforcing sheath 141, along with a barrel portion of the core member 180. The inner diameter of the inner channel of the sleeve 190 is therefore selected so as to permit the distal reinforcing sheath 141 to be disposed within the inner channel, preferably resulting in a frictional fit between the sleeve 190 and the distal reinforcing sheath 141.

The sleeve 190 has a first end 192 and a second end 194 with the first end 192 being disposed in close proximity to the distal tip 170. As best shown in FIG. 7, there is a very slight gap formed between the first end 192 and the distal tip 170. In this gap, the core member 180 is covered with the second reinforcing sheath 141. The second end 194 extends beyond the end 182 of the core member 180 which is disposed within the inner lumen of the second reinforcing sheath 141.

The sleeve 190 is then crimped or otherwise compressed at selected regions along its length, resulting in the core member 180 and the second reinforcing sheath 141 being securely held in place at the distal portion 110 of the lead 100. The core member 180 thus serves as a die against which the sleeve 190 is crimped. During use, movement of the core member 180, as well as the distal tip 170 formed at the head 186 thereof, is not desired. Because the core member 180 is simply inserted into the second reinforcing sheath 141 and initially held in place therein by frictional forces, the crimping of the sleeve 190 around the core member 180 effectively provides a retention force that supplements the existing frictional fit between the sleeve 190 and the second reinforcing sheath 141 and the core member 180.

By crimping the distal portion 110 in the above-described manner, several advantages are realized. First, the distal portion 110 includes the second reinforcing sheath 141 which provides rigidity and reinforcement of the distal portion 110 so that when the distal portion 110 is placed under stress, the second reinforcing sheath 141 serves to disperse the stress longitudinally over a surface thereof and away from the distal tip 170. The crimped sleeve 190 also acts to longitudinally disperse the stress (induced by an external force being applied to the distal portion 110 during implantation and or normal use of the lead 100) along the distal portion 110. The crimped components of the distal portion 110 act to distribute stress over a much larger area compared to conventional lead constructions, and this results in the stress point of the distal portion being moved away from the distal tip 170. In other words, the stress is dispersed longitudinally along the distal portion 110, thereby reducing the stress that is applied to a distalmost electrode. The achieved result is a great reduction or elimination in the likelihood that this distalmost electrode will become dislodged or that the conductive connection will fail due to excessive stress.

After the crimping operation is performed, crimped sections 191 are formed in the sleeve 190 in the regions which were pinched or pressed together by a conventional crimping apparatus (not shown). Because the distal reinforcing sheath 141 is a thin-walled polymeric member, the crimping action should only be performed in regions where the core member 180 is present as the intended function of the crimping action is to securely hold and retain the core member 180 in place within the inner lumen of the distal reinforcing sheath 141. The core member 180 provides a sufficiently rigid member to permit the crimping action to performed thereagainst.

The sleeve 190 can be formed from a number of different suitable materials; however, it has been found that the sleeve 190 should be formed of a metal material as metal materials have improved crimping capabilities, resulting in the core member 180 being securely held in place by the crimped sleeve 190. For example, the sleeve 190 can be formed of a biocompatible material, such as platinum or a platinum-iridium alloy.

The proximal portion 120 of the lead 100 is used to attach the lead 100 to a device or some other type of equipment. In various embodiments, the proximal portion 120 may be adapted for implantable use or may be designed for external attachment for short-term inpatient or long-term percutaneous use. The proximal portion 120 may have a specifically designed lead connection adapter or may simply include separate conductors to attach to a junction block. According to one embodiment, the proximal portion 120 includes four coaxial lead connection terminals 220, 222, 224, 226 (also referred to herein as "electrical contacts"), each of which is electrically connected to one of a plurality of distal electrodes 210, 212, 214, 216 via an electrical conductor 200 extending through the lead 100. In the disclosed embodiment, the four lead connection terminals 220, 222, 224, 226 are provided to enable compatibility between the lead 100 and an implantable neurostimulator having a corresponding inline connector, as will be described in greater detail hereinafter.

The electrical conductors 200 form a part of a conductor set and preferably, each electrical conductor 200 is arranged in a generally helical manner through the interior of the lead 100 and around the first reinforcing sheath 140 in the proximal portion 120 and around the second reinforcing sheath 141 in the distal portion 110. A helical configuration is favored because of its ability to tolerate longitudinal stretching of the lead 100 without breaking. The conductor set thus includes a sufficient number of electrical conductors 200 for establishing an electrical connection between the lead connection terminals 220, 222, 224, 226 and the respective electrodes 210, 212, 214, 216 formed at the distal portion 110.

The individual electrical conductors 200 can be formed of a number of different conductive materials so long as the electrical conductors can be fabricated in the preferred coiled (helical) arrangement that is shown in FIGS. 2 through 5. In addition, each electrical conductor 200 is fabricated so that it contains an outer insulating layer for conductively insulating one electrical conductor 200 from the other electrical conductors 200. For example, each electrical conductor 200 can be formed of platinum or a platinum-iridium alloy with the outer insulating layer being formed of a fluorinated nylon material for independently insulating each electrical conductor 200.

In the exemplary embodiment where the lead 100 contains four electrodes 210, 212, 214, 216 and four lead connection terminals 220, 222, 224, 226, the conductor set 200 includes four electrical conductors 200, one for each of the electrodes 210, 212, 214, 216 and its corresponding lead connection terminal 220, 222, 224, 226. The conductor set is thus characterized as being a "quad conductor" in this exemplary embodiment. As will be described in greater detail below, each of the electrical conductors 200 in the conductor set is affixed to and in conductive communication with one of the electrodes 210, 212, 214, 216 and one of the lead connection terminals 220, 222, 224, 226.

It will be appreciated that in the above-described embodiment, a length of each conductor 200 is not supported by one of the reinforcing sheaths 140, 141 since the combined reinforcing sheaths 140, 141 do not extend along the complete length of the lead 100. In other words, a medial section 101 of the lead 100 does not contain a reinforcing sheath as part of its structure and therefore the conductors 200 are simply coiled in this medial section 101 and are not arranged around a reinforcing member. Because the medial section 101 does not contain a reinforcing member as a backbone, the medial section 101 is very flexible and permits the lead 100 to be easily bent in a variety of directions, thereby facilitating the implantation of the lead 100. This medial section 101 thus extends between the first end 142 of the first (proximal) reinforcing sheath 140 and the second end 145 of the second (distal) reinforcing sheath 141. Preferably, the length of the first reinforcing sheath 140 is selected so that when the lead 100 is assembled, each of the lead connection terminals 220, 222, 224, 226 is disposed around the first reinforcing sheath 140. Similarly, the length of the second reinforcing sheath 141 is selected so that each of the electrodes 210, 212, 214, 216 is disposed around the second reinforcing sheath 141. It will be understood that in the embodiment where the reinforcing sheath extends substantially the entire length of the lead 100, the medial section 101 is eliminated.

As illustrated in the Figures, the electrical conductors 200 of the conductor set are each coiled around the reinforcing sheaths 140, 141 about the longitudinal axis of each sheath. It will be appreciated that a first electrical conductor 200 is affixed to and in conductive communication with the electrode 210 at one end thereof and is affixed to and in conductive communication with the lead connection terminal 220 at another end thereof. Similarly, a second electrical conductor 200 is affixed to and in conductive communication with the electrode 212 and the lead connection terminal 222; the third electrical conductor 200 being affixed to and in conductive communication with the electrode 214 and the lead connection terminal 224; and the fourth electrical conductor 200 being affixed to and in conductive communication with the electrode 216 and the lead connection terminal 226. Other configurations are, of course, possible, including asymmetric configurations in which one terminal is connected to multiple electrodes, or vice versa. As previously mentioned, each of the electrical conductors 200 is electrically insulated from adjacent electrical conductors 200. One exemplary method of attaching one electrical conductor 200 to one respective electrode and one respective lead connection terminal will be described in greater detail below.

It will be appreciated that between the first lead connection terminal 220 and the second lead connection terminal 222, only the first electrical conductor 200 is present and similarly between the first electrode 210 and the second electrode 212, only the first electrical conductor is present. The concentration of electrical conductors 200 is greatest between the lead connection terminal 226 and the electrode 216 since all four electrical conductors 200 are present in this region.

It will be understood that there are a number of different ways to conductively link one of the lead connection terminals 220, 222, 224, 226 to one of the electrodes 210, 212, 214, 216 using the electrical conductors 200 besides the aforementioned arrangement where the one electrical conductor 200 is attached at one end to the proximalmost lead connection terminal (first electrical contact 220) and at the other end to the distalmost electrode (first electrode 210). For example, one electrical conductor 200 can be attached at one end to the proximalmost lead connection terminal (first electrical contact 220) and at the other end to the proximalmost electrode (fourth electrode 216). The specific arrangement of the electrical conductors 200 between the lead connection terminals 220, 222, 224, 226 and the electrodes 210, 212, 214, 216 is not critical so long as each electrical conductor 200 is electrically isolated from the other electrical conductors 200, as well as each lead connection terminal being electrically isolated from the other lead connection terminals and each electrode being electrically isolated from the other electrodes.

One exemplary method of attaching one of the electrical conductors 200 to a respective lead connection terminal and a respective electrode is best illustrated with reference to FIGS. 3-6. FIGS. 3 and 4 illustrate the attachment of the electrical conductors 200 to the individual lead connection terminals 220, 222, 224, 226, while FIGS. 2, 5 and 6 illustrate the attachment of the electrical conductors 200 to the individual electrodes 210, 212, 214, 216.

As previously mentioned, one end of the first electrical conductor 200 is conductively attached to the first lead connection terminal 220. Because it is preferable for each electrical conductor 200 not to extend beyond the outer surface of the respective electrical contact, the electrical conductor 200 is preferably conductively attached to the lead connection terminal by disposing the one end of the electrical conductor 200 into a receiving feature formed in the lead connection terminal. For example, the lead connection terminal can be fabricated to have a slot or bore formed therein for receiving the electrical conductor 200 such that the electrical conductor 200 does not extend beyond the outer surface of the lead connection terminal when the electrical conductor 200 is inserted and retained within the receiving feature (e.g., slot or bore), as illustrated in FIG. 3. In the embodiment of FIG. 3, the end of the electrical conductor 200 is inserted and retained within the receiving feature (e.g., slot or bore), as illustrated in FIG. 3. In the embodiment of FIG. 3, the end of the electrical conductor 200 is inserted into a slot 230 formed in the first lead connection terminal 220. The end of the electrical conductor 200 is then fixedly secured to the first lead connection terminal 220 using conventional means that is suitable for the intended purpose. For example, the electrical conductor 200 can be fixedly secured to the first lead connection terminal 220 by welding the one end thereto. The slot 230 is preferably configured so that its depth permits the end of the electrical conductor 200 to lie within the slot 230 flush against the first lead connection terminal 220 and not protrude beyond the outer surface of the first lead connection terminal 220. From the point of attachment with the first lead connection terminal 220, the electrical conductor 200 extends downwardly to a coiled configuration such that the reinforcing sheath 140 can be received between the coils.

Figure 20A:
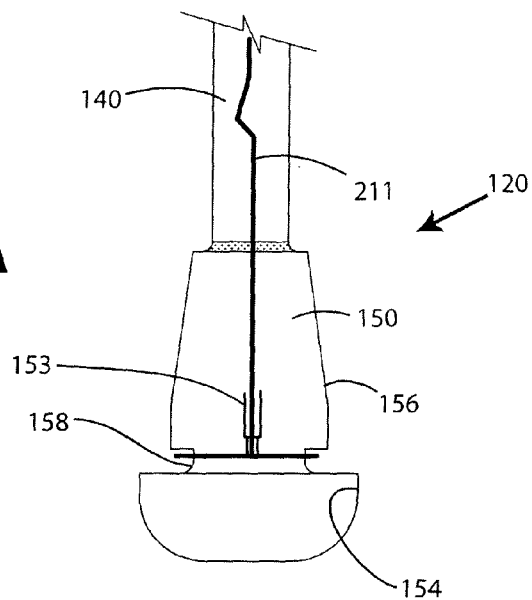
FIG. 20A is a top plan view of a partial section of the proximal portion of the lead showing a proximal reinforcing sheath attached to a bushing with a reinforcing fiber being arranged around and secured to the bushing.
Figure 20B:
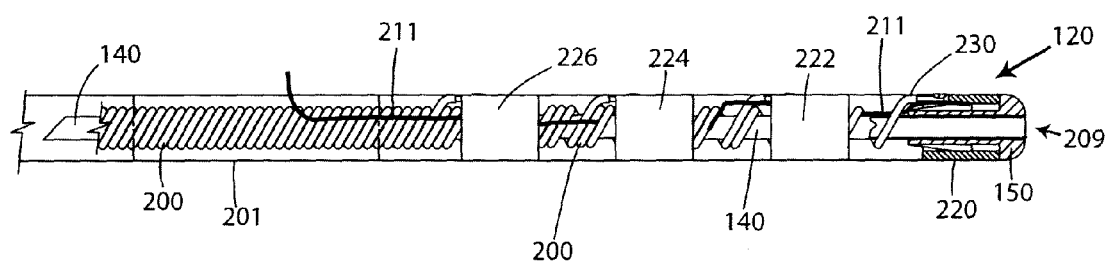
FIG. 20B is a partial cross-sectional view of the lead of FIG. 1 showing the reinforcing fiber of FIG. 20A being arranged around an outer surface of the conductors.

Referring now to FIGS. 20A and 20B, an additional reinforcing element 211 is preferably included as part of the proximal portion 120 of the lead 100. This reinforcing element 211 is disposed around an outer surface of the bushing 150 underneath the first lead connection terminal 220. The reinforcing element 211 can be disposed around the bushing 150 using any number of techniques, including but not limited to wrapping and tying the reinforcing member around the bushing 150. The reinforcing element 211 is designed to further reinforce the proximal portion 120 of the lead 100 as will be described in greater detail below.

The reinforcing element 211 can be formed of any number of bio-compatible materials that can accomplish the intended function. Some exemplary materials from which the reinforcing element 211 can be fabricated include but are not limited to Kevlar® (from DuPont of Wilmington, Del.), nylon, polyethylene, and liquid crystal polymer (LCP). The reinforcing element 211 can be colored using a non-nutrient die that is designed to color suture material. In one preferred embodiment, the reinforcing element 211 is formed of a polyester, non-absorbable suture stock. In this embodiment, the polyester reinforcing element 211 is fabricated using a number of polyester fiber strands (e.g., 20 or more fibers that each have a thickness of about 0.0003 inch) that are arranged to form a twisted cable structure.

In addition to having a radial groove in the form of the recessed section 158, the bushing 150 further has an axial slot 153 formed therein. The axial slot 153 is formed in the tapered section 156 and is formed generally perpendicular to the radial groove 158. In the embodiment where the reinforcing element 211 is formed of polyester fibers, the reinforcing element 211 is cut to a predetermined length and is then wrapped around the bushing 150 within the radial groove 158 and is then tied in a knot in the radial groove 158, leaving two free ends. The two free ends of the reinforcing element 211 are then brought together and the two end sections of the reinforcing element 211 are orientated within the axial slot 153. The length of the reinforcing element 211 is preferably such that even after the reinforcing element 211 is laid within the axial slot 153, the two end sections of the reinforcing element 211 can extend the complete length of the proximal reinforcing sheath 140. As will be described in greater detail below, in the assembled lead 100, the reinforcing element 211 remains disposed within the axial slot 153 and the two end sections of the reinforcing element 211 are disposed around a length of the conductors 200. In the assembled state the polyester fibers forming the reinforcing element 211 tend to flatten out, especially in the area where the polyester fibers are disposed between the bushing 150 and then the first lead connection terminal 220.

The proximal reinforcing element 211 acts to longitudinally disperse stress induced by external forces being applied to the proximal portion 120. More specifically, the wrapping of the proximal reinforcing element 211 around the bushing 150, between the first lead connection terminal 220 and the bushing 150, provides a member which longitudinally disperses stress over a greater area compared to conventional lead constructions that do not have any reinforcing/stress dispersing elements incorporated therein. Similar to the reinforcement at the distal portion 110, the incorporation of the reinforcing element 211 into the proximal portion 120 effectively moves the stress point away from the proximal end and as a result, the first connection terminal 220 is not placed under excessive stress that could cause the electrical connection to fail or even the dislodgement of the first connection terminal 220 from the lead 100.

Referring again to FIGS. 1 through 8 the other lead connection terminals 222, 224, 226 are spaced along the conductors 200 and the reinforcing sheath 140 in a similar manner as the first lead connection terminal 220. The lead connection terminals 220, 222, 224, 226 are spaced along the proximal portion 220 at any desired interval, and preferably, the distance between the next adjacent lead connection terminals is the same. For example, the lead connection terminals 220, 222, 224, 226 can be spaced at a pitch of approximately 3.5 mm to approximately 10 mm. It will be understood that these pitch values are merely exemplary and not limiting since the lead 100 can have pitch values outside of the above range depending upon the precise application.

Because the lead connection terminals 220, 222, 224, 226 are preferably ring-shaped, the reinforcing sheath 140, well as the respective conductors 200 coiled around the reinforcing sheath 140, pass through openings formed through the lead connection terminals 220, 222, 224, 226. While, the first lead connection terminal 220 has only one electrical conductor 200 passing through the opening formed therethrough due to its proximalmost location, the opening formed through the fourth lead connection terminal 226 can accommodate the four electrical conductors 200 that are coiled around the reinforcing sheath 140.

The electrical conductors 200 are preferably attached to the electrodes 210, 212, 214, 216 in the same manner as the electrical conductors 200 are attached to the lead connection terminals 220, 222, 224, 226. In one embodiment, the first electrode 210 serves as the distalmost electrode and is disposed around the sleeve 190.

The electrical conductor 200 is conductively attached to the first electrode 210 by disposing the one end of the electrical conductor 200 into a receiving feature formed in the first electrode 210. As with the lead connection terminals, each of the electrodes 210, 212, 214, 216 can be fabricated to have a slot or bore formed therein for receiving the electrical conductor 200 such that the electrical conductor 200 does not extend beyond the outer surface of the respective electrode when the electrical conductor 200 is inserted and retained within the receiving feature as illustrated in FIG. 5. In the embodiment of FIG. 5, the end of the electrical conductor 200 is inserted into a slot 231 formed in the first electrode 210. The end of the electrical conductor 200 is then fixedly secured to the first electrode 210 using conventional means that are suitable for the intended purpose, such as welding, etc. When the end of the electrical conductor 200 is welded to the first electrode 210, a weld zone 235 is formed as illustrated in FIG. 6. The slot 231 is preferably configured so that its depth permits the end of the electrical conductor 200 to lie within the slot 231 flush against the first electrode 210 and not protrude beyond the outer surface of the first electrode 210.

In the assembled state, the first lead connection terminal 220 is disposed around the bushing 150 at the proximal portion 120 of the lead 100. Preferably, one end of the first lead connection terminal 210 is placed in an abutting relationship with the head 154 of the bushing 150. The other end of the first lead connection terminal 220 preferably does not extend beyond the tapered section 156 of the bushing 150; however, it may extend beyond the tapered section 156 in some embodiments. The outer diameter of the first lead connection terminal 220 is preferably equal to or less than the greatest outer diameter of the bushing 150 so that the first lead connection terminal 220 does not extend radially beyond the bushing 150.

More specifically, the first electrode 210 is disposed as close to the distal tip 170 as practical (e.g., in an abutting relationship therewith). A slight gap may be formed between the first electrode 210 and the sleeve 190 when the first electrode 210 is disposed in place. The first electrode 210 is dimensioned so that the outer diameter thereof is equal to or less than the greatest diameter of the distal tip 170.

Another feature of the present lead 100 is that the design of the distal tip 170 facilitates an iso-diametric tip as there is an almost seamless transition between the tip and contact arrangement. This seamless transition results because the outer diameter of the distal tip 170 and the first electrode 210 are substantially equal and the first electrode 210 is disposed in abutment with or in very close proximity to the distal tip 170. The advantage of having an iso-diametric tip is realized during lead revision. If the diameter of the distal tip 170 exceeds the diameter of the first electrode 210, detrimental tissue damage could result during the implantation process as the lack of a smooth transition between the two components could result in the tissue being "snagged" by the distal portion 110 due to the differing diameters.

The un-crimped portion of the sleeve 190 extends beyond the end of the first electrode 210 with the electrical conductor 200 extending across the sleeve 190 to the slot 231. The outer dimensions of the sleeve 190, the first electrode 210, and the electrical conductor 200 are preferably selected so that the electrical conductor 200 does not radially extend beyond the outer surface of the first electrode 210 when the electrical conductor 200 is disposed in place along the sleeve 190. Because the electrodes 210, 212, 214, 216 are preferably ring-shaped, the reinforcing sheath 141, as well as the respective conductors 200 coiled around the reinforcing sheath 141, pass axially through openings formed through the electrodes 210, 212, 214, 216.

The lead 100 includes a flexible shaft 201 (lead body) that surrounds the internal components of the lead 100. The flexible shaft 201 thus houses the internal components (e.g., reinforcing sheaths 140, 141; electrical conductors 200; at least a portion of the bushing 150; sleeve 190, etc.) and extends from the distal end of the distal portion 110 to the proximal end of the proximal portion 120. In the illustrated embodiment, the flexible shaft 201 is in the form of a tubular shaft. The shaft 201 is preferably fabricated from silicone or some other flexible, durable, and biocompatible material.

In one exemplary embodiment, the fabrication of the flexible shaft 201 is completed after the electrodes and the lead connection terminals have been conductively joined to the conductors 200. In this one exemplary embodiment, the flexible shaft 201 is actually formed by first disposing a flexible shaft 201 of a predetermined length around the coiled conductors 200 such that opposing ends of the coiled conductors 200 extend beyond the ends of the flexible shaft 201. The electrodes and the lead connection terminals are then disposed around the exposed ends of the conductors 200 and conductively connected to the respective conductors at preselected locations to maintain a desired spacing therebetween. The spaced electrodes and lead connection terminals are thus initially disposed beyond the ends of the cut flexible shaft 201. The lead 100 is then further fabricated by disposing the reinforcing sheath 140 through the conductors 200 at the proximal portion 110 and disposing the reinforcing sheath 141 through the opposite end of the conductors at the distal portion 110, then crimping the components at the distal portion 110, and constructing the proximal portion 120 by coupling the bushing 150 to the sheath 140. The fabrication of the flexible shaft 201 is then completed by placing the partially assembled lead 100 into a mold where liquid silicone is injected around and under the electrodes and the lead connection terminals to extend the flexible shaft 201 to the distal and proximal ends. The injected silicone thus becomes integral with the initial cut length of the flexible shaft 201, resulting in a unitary flexible shaft 201 being formed that extends substantially the entire length of the lead 100 and is selectively formed around the electrodes and the lead connection terminals so that a portion of each electrode and lead connection terminal is exposed. As previously mentioned, the flexible shaft 201 is preferably formed so the outer diameter thereof is substantially equal to the outer diameter of the electrodes and the lead connection terminals.

The injected silicone also flows between the initial cut length of the flexible shaft 201 and the conductors 200—thereby at least partially embedding the conductors 200 within the flexible shaft 201—and serves to bind the conductors 200 in place along selected portions thereof. The injected silicone also flows over the end sections of the proximal reinforcing element 211 (FIGS. 20A and 20B) which are disposed, in a random manner, along the outer surfaces of the conductors 200. Upon curing, the injected silicone thus serves to bind the end sections within the interior of the lead 100 along the outer surfaces of the conductors 200. In one exemplary embodiment, after the end sections of the reinforcing member 211 are disposed within the axial slot 153, the free ends are brought to the first end 142 of the proximal reinforcing sheath 140 and then threaded through the longitudinal lumen defined by the proximal reinforcing sheath 140 before being threaded through the bore 152 formed in the bushing 150. The proximal reinforcing sheath 140 is then inserted into the conductors 200 so that the conductors are coiled therearound. Using several techniques, the free ends of the reinforcing member 211 are then directed back through the bore 152 and the longitudinal lumen so that the end sections are disposed within the interior of the conductor coils. The end sections are then threaded through the conductor coils to cause the end sections to migrate to the outer surfaces of the conductors 200. The end result of this process is that the end sections lie randomly along the outer surfaces of the conductors 200. The injected silicone then serves to generally bind and immobilize the end sections as the end sections are bound to adjacent structures, such as the conductors 200 and the lead body (flexible shaft 201) itself.

The electrodes 210, 212, 214, 216, as well as the lead connection terminals 220, 222, 224, 226 are formed of a biocompatible conductive material, preferably platinum or a platinum-iridium alloy. The electrodes 210, 212, 214, 216 are arranged around and somewhat embedded into the flexible shaft 200 at the distal portion thereof as a result of the above-described exemplary fabrication process. Similarly, the lead connection terminals 220, 222, 224, 226 are arranged around and somewhat embedded into the flexible shaft 201 at the proximal portion thereof. The individual electrical conductors that are arranged around the stiffening sheath 140 and in conductive communication with the lead connection terminals 210, 222, 224, 226 and the individual electrical conductors that are arranged around the stiffening sheath 141 and in conductive communication with the electrodes 210, 212, 214, 216 are preferably either flush with or below an outer surface of the flexible shaft 201 so that the outer surface of the flexible shaft 201 is relatively smooth and free of obstructions. Of course, the flexible shaft 201 is fabricated so that a surface of each electrode 210, 212, 214, 216 and each lead connection terminal 220, 222, 224, 226 is exposed to permit the electrodes and lead connection terminals to perform their intended functions.

At the proximal end of the lead 100, a stylet opening 209 is formed and is in communication with the longitudinal lumen, defined by the reinforcing sheath 140, thereby permitting the stylet 130 to be inserted into the lead 100. The stylet 130 is then fed through the conductors 200 in the medial section 201 of the lead 100 before then being inserted into the longitudinal lumen defined by the reinforcing sheath 141 at the distal portion 110. The stylet 130 is thus extended along a length of the lead 100 to provide a temporary measure of rigidity to assist in placement of the lead 100. The use of a stylet 130 to implant brain electrodes is a common practice. Although implantable lead 100 should be able to tolerate some leakage and penetration of body fluids when chronically implanted, it is advantageous to provide this structure to avoid excessive contamination.

In one embodiment, when the lead 100 is coupled to an implanted neurostimulator via the lead connection area of the proximal portion 120, a suitable overall length for the lead 100 is between approximately 100 and 500 mm. The body portion (flexible shaft 201) of the lead 100 has a diameter between approximately 0.5 mm and approximately 2.0 mm, and is preferably between approximately 1.0 mm and approximately 1.3 mm. It is preferable for the lead 100 to have a thinner construction since this provides advantages in structural integrity, ease of manufacturing, and ease of handling. A thinner construction has the advantage that during use, less brain trauma will result because of the reduced dimensions of the lead 100; however, as the thickness of the lead 100 is increased, the robustness will improve.

The electrodes 210, 212, 214, 216 may vary in size. As is well known in the art of designing physiological sensing and stimulation electrodes, a stimulation electrode's surface area is proportional to the electrical current density (and charge density) delivered by the electrode, and analogously, a sensing electrode's surface area is proportional to its sensitivity to electrographic signals. To minimize departures from the electrical parameters used with traditional strip and grid electrodes, it may be beneficial to provide distal electrodes 210, 212, 214, 216 with surface areas comparable to those of traditional electrodes.

A standard strip or grid electrode has a surface area of approximately 4 to 15 $mm^2$, with a representative electrode having a surface area of approximately 8 $mm^2$. The latter surface area measurement corresponds to an exposed circular contact surface having a diameter of approximately ⅛ inch (or 3.2 mm). To provide the equivalent surface area on a ring electrode having a diameter of 0.5 mm, an electrode length of approximately 5 mm would be necessary.

For varying neurological sensing and stimulation applications, it is currently believed that electrode surface areas between 0.75 mm$^2$ and 15 mm$^2$ would be advantageous. On a distal end segment having a ring electrode with a diameter of 0.5 mm, an electrode length of 0.5 mm yields a surface area of approximately 0.75 mm$^2$, and on a distal end segment having a ring electrode with a diameter of 1.5 mm, an electrode length of 3 mm yields a surface area of approximately 15 mm$^2$. In any event, it is not necessarily advantageous to match the surface area of the electrodes of lead 100 with traditional strip, grid, and depth electrodes, particularly when current and charge parameters can be adjusted to compensate. It should be noted, however, that decreasing the surface area of an electrode might, in some circumstances, disadvantageously decrease sensitivity in a sensing application, or fail to stimulate a sufficient population of neurons in a stimulation application. Similarly, increasing the surface area too far might decrease precision in a sensing application and might require a prohibitively high current to be applied in a stimulation application. These considerations are known in the art of medical sensing and stimulation electrode design.

All of the dimensions set forth above are considerably variable, particularly when the lead 100 is employed in different applications. The specific measurements and dimensions provided herein are intended to provide details on specific exemplary embodiments, and the scope of the invention should not be limited thereby.

Figure 16:
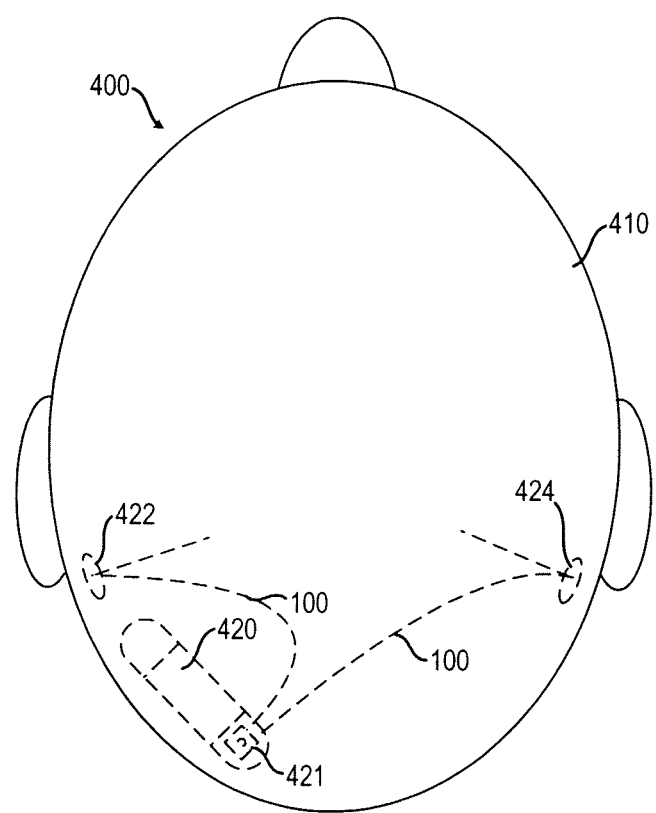
FIG. 16 is a schematic view of an implantable neurostimulator system incorporating the lead of FIG. 1.

Now referring to FIGS. 15 through 16, the lead 100 is used according to one exemplary embodiment as a depth lead for implantation into the brain. Traditional deep brain leads are frequently positioned in desired deep brain structure with the assistance of a cannula, a rigid tunneling and positioning tool capable of sliding over the shaft of the brain electrode. The cannula is retreated once the cannula (and the lead inside) is appropriately placed. However, the present lead 100 does not necessarily require the use of a cannula since the entire lead 100 is not necessarily embedded in the brain in all surgical procedures.

FIG. 15 is a schematic cross-section of the anatomy of a patient's head, illustrating an example of how the lead 100 may be employed. The drawing of FIG. 15 is not to scale, and is not necessarily intended to represent any particular anatomical features or landmarks.

In general, the lead 100 is advantageously situated below a patient's scalp 300, and extends through the patient's cranium 310 and dura mater 320 to access the patient's cortex 330. The lead 100, and more particularly, the distal portion 110 thereof, is inserted into a desired electrode site (target area) depending on the specific application. Choosing desired electrode sites may be performed at any appropriate stage of the surgical procedure, including presurgically in an operative planning stage; intraoperatively after a craniotomy has been performed or a burr hole has been made; or intraoperatively after one or more other procedures, such as functional mapping, have been performed.

The lead 100 can be inserted a short distance into the cortex 330, only enough to ensure that one or more of the electrodes 210, 212, 214, 216 are fully embedded in neural tissue. In a depth lead application, such as the one illustrated in FIG. 15, the lead 100 is inserted into deeper tissue of the cortex 330 in comparison to a strip electrode application, where the electrodes are positioned on the cortex 330 in an essentially collinear configuration. Other configurations are, of course, possible, and are described elsewhere herein. Not all of the electrodes 210, 212, 214, 216 need to be embedded within neural tissue since in some applications, it may be desirable to embed only the first electrode 210, or the first and second electrodes 210, 212 or the first, second, and third electrodes 210, 212, 214. In other words, the distal portion 110 can be implanted to a desired depth to reach the target area that has been selected.

The distal portion 110, including the electrodes 210, 212, 214, is inserted, according to one embodiment, into the cortex 330 substantially normal to the surface of the brain (as illustrated) since this arrangement minimizes tissue damage. However, it will be appreciated that the distal portion 110 is not limited to being implanted in such a configuration and the distal portion 110 can be implanted at any stereotactic angle that is possible. For example, certain target areas will have to be approached in different ways since there are certain obstacles (e.g., blood vessels, ventricles, certain functional brain areas, etc.) that can prevent the simple insertion of the lead 100 into the cortex 330.

Preferably, the distal portion 110 has sufficient flexibility where it exits the cortex 330 to avoid adverse pressure effects on the brain or any portion of the lead 100. In the absence of external forces, the distal portion 110 will ordinarily remain implanted in the desired electrode site without any affixation means, but if desired, anchors (not shown) can be provided at the distal portion 110 to improve retention. Such anchors can be in the form of barbs provided on the flexible shaft 201 or a textured surface formed as part of the flexible shaft 201. However, providing such retention mechanisms is ordinarily not desirable, since these mechanisms can potentially adversely impact ease of extraction or repositioning when necessary.

The distal portion 110 is inserted into the cortex 330 through a burr hole 340 defined in the patient's cranium 310 and preferably surgically formed. The lead 100 is anchored within the burr hole 340 by way of a burr hole cover 350 inserted within and affixed to the burr hole 340. The burr hole cover 350 is adapted to hold the lead 100 in place and prevent undesired movement of the distal portion 110, even if a force is applied to another portion of the lead 100. Various configurations of burr hole covers are well known in the art and are commercially available. Alternatively, the lead 100 can be cemented within the access hole.

As described above, the proximal portion 120 of the lead 100 connects to an implanted neurostimulator (not shown) or the like. Because of this arrangement, it may be advantageous in some applications to anchor the lead 100 to the patient's cranium 310 at one or more points between the burr hole 340 and the neurostimulator, so that the lead 100 remains in a preferred location under the patient's scalp 300.

During the above-described insertion process, the stylet 130 remains inserted into the interior of the lead 100 such that it extends along the longitudinal length of the lead 100 from the proximal portion 120 to the distal portion 110. The stylet 130 provides rigidity and serves to "push" the lead 100 through the soft brain tissue. Once the distal portion 110 of the lead 100 and more particularly, the electrodes 210, 212, 214, 216 are disposed in their desired locations, the stylet 130 is removed from the lead 100. The lead 100 remains implanted in place due to the frictional fit between the lead 100 and the surrounding brain tissue. Moreover, the burr hold cover 350 further serves to hold the lead 100 in place.

FIG. 16 schematically illustrates an exemplary configuration of an implantable system 400 for the treatment of neurological disorders, as it would be generally situated under the scalp of a patient's head 410 and implanted intracranially.

The illustrated embodiment of the system 400 has a control module 420 and two leads 100, each of which connects a lead connector 421 on the control module 420 to a plurality of distal electrodes 210, 212, 214, 216. It will be appreciated that the control module 420 can be of the type that can be permanently implanted into the patient's cranium in a location where the bone is fairly thick. In an alternative embodiment, the control module 420 can be located in the trunk of the patient's body like a heart pacemaker with the connecting wires being run under the patient's skin. As described above, the electrodes 210, 212, 214, 216 (FIG. 15) are placed deep into the brain when the depth leads 100 of FIGS. 1-8 are used. The leads 100 are run from the control module 420, underneath the patient's scalp 300, through burr holes 422, 424 to the electrodes placed beneath the patient's cranium. Although this embodiment is described as each lead 100 having four distal electrodes 210, 212, 214, 216, it will be appreciated that more (or fewer) than four electrodes with connecting conductors can be used in the present leads 100.

As described above, the leads 100 carry EEG signals from the electrodes 210, 212, 214, 216 to the neurostimulator (control module 420). The electrodes 210, 212, 214, 216 can also be selectively energized by the neurostimulator (control module 420) via the leads 100 to electrically stimulate the patient's brain. Further information on detector methods, stimulation schemes, and systems adaptable to employ the systems and methods set forth herein are described in detail in U.S. Pat. No. 6,016,449 to Fischell et al., which has been previously incorporated by reference in its entirety.

Now referring to FIGS. 9-14, a lead according to another embodiment is illustrated and generally indicated at 500. The lead 500 of this embodiment is of a type that is known as a surface cortical lead. FIG. 9 is an exploded view of the lead 500. The lead 500 has some similar components and similar features as the lead 100 and therefore, not all of the components of the lead 500 will be discussed in great detail. More specifically, only the differences between the lead 500 and the lead 100 will be discussed in great detail and like elements are numbered alike.

Similar to the lead 100, the lead 500 is an elongated structure having a distal portion 510 and a proximal portion 520. The proximal portion 520 has a very similar, if not identical, construction compared to the proximal portion 120 of the lead 100. Similar to the alternative first embodiment, the lead 500 includes a longitudinal reinforcing sheath 511 that, in one embodiment, extends from the proximal portion 520 to the distal portion 510 for enhancing the rigidity of the lead 500. In another embodiment, two distinct reinforcing sheaths are provided, as previously described in an earlier embodiment, with one reinforcing sheath being disposed at the distal portion 510 and another reinforcing sheath being disposed at the proximal portion 520. A proximal end of the reinforcing sheath 511 is securely coupled to the bushing 150 using conventional techniques (e.g., an adhesive). The head 154 of the bushing 150 forms a proximal end of the lead 500. The stylet 130 is received within a bore formed through the bushing 150 and is then received within the longitudinal lumen of the reinforcing sheath 511, where the stylet 130 travels therethrough and through the conductors 200 to the distal portion 510 of the lead 500.

The proximal portion 520 of the lead 500 also includes a predetermined number of lead connection terminals that are each connected to an electrode at the distal portion 510 via electrical conductors. In the illustrated embodiment, the lead 500 includes four lead connection terminals 220, 222, 224, 226 and four electrodes 530, 532, 534, 536 with an independent electrical conductor 200 extending between one of the lead connection terminals 220, 222, 224, 226 and a respective one of the electrodes 530, 532, 534, 536. It will be understood that the distal portion 510 and the proximal portion 520 include reinforcing elements to disperse any stress at each of the respective portions.

As shown in FIGS. 12 and 13, the independent electrical conductors 200 are coiled around the stiffening sheath 511 in a helical configuration with each electrical conductor 200 being conductively insulated from adjacent other electrical conductors 200. One end of each electrical conductor 200 is attached to one of the lead connection terminals 220, 222, 224, 226 and to one of the electrodes 530, 532, 534, 536. The ends of the electrical conductor 200 can be attached using any of the techniques mentioned previously herein, including welding (which forms a weld zone 235).

The lead connection terminal 220 is disposed around the bushing 150 at the proximal portion 520 of the lead 500. Preferably, the lead connection terminal 220 is disposed as close as possible to the bushing 150 (i.e., in an abutting relationship with the head of the bushing 150). The other lead connection terminals 222, 224, 226 are spaced along the reinforcing sheath 511 in a similar manner as the lead connection terminal 220. In other words, the lead connection terminals 220, 222, 224, 226 are spaced along the proximal portion 520 at any desired interval, and preferably, the distance between next adjacent lead connection terminals is the same (e.g., 10 mm pitch). The lead connection terminals 220, 222, 224, 226 are somewhat embedded into the flexible shaft 201.

The lead 500 includes the flexible shaft 201 which acts as a lead body and extends from the proximal end of the lead 500 to an intermediate point. Unlike the lead 100 embodiment, the flexible shaft 201 does not extend to distal portion 510 of the lead 500. The flexible shaft 201 terminates at the 202 which is disposed prior to the location of the proximalmost electrode 526 when the lead 500 is assembled.

The difference between the lead 500 and the lead 100 is most notable in the distal portion 510 of the lead 500. The distal portion 510 is configured as an electrode strip assembly 513. The electrode strip assembly 513 includes a distal section of the reinforcing sheath 511 having the electrical conductors 200 wrapped therearound, as well as a core member 540 (which may be similar to core member 180 or may be any other type of plug-like member). The core member 540 is partially disposed within the lumen of the reinforcing sheath 511. A head of the core member 540 extends beyond the distal reinforcing sheath 511. A core member 540 has a bore formed therein for receiving the stylet 130 as the stylet 130 is fed through the lumen of the reinforcing sheath 511 toward the distal end of the lead 500. In one exemplary embodiment, the core member 540 is formed of a metal, e.g., platinum or platinum-iridium alloy.

As with the lead 100, the assembly 513 includes the sleeve 190 that is disposed around a length of the stiffening sheath 511. The sleeve 190 is formed of a material that can be crimped or otherwise compressed in selected regions so as to securely locate and hold other components of the assembly 513 in place at the distal portion 510. Prior to being compressed, the sleeve 190 is a tubular member that receives a length of the reinforcing sheath 511 and a barrel portion of the core member 540. The sleeve 190 is then crimped or otherwise compressed at selected regions along its length, resulting in the core member 540 and the reinforcing sheath 511 being securely held in place at the distal portion 510 of the lead 500. The crimping operation produces crimped sections 191 in the sleeve 190. Then, the distal portion 510 provides a similar stress dispersing feature similar to that described with reference to the depth lead embodiment. The crimping causes the stress to be dispersed longitudinally along the distal portion 510 instead of being localized at the distal tip thereof (which can result in the electrode 530 being placed under excessive stress).

In this embodiment, each of the electrodes 530, 532, 534, 536 has a flat disc shape with the electrode 530 being the distalmost electrode and the electrode 536 being the proximalmost electrode. In the exploded view of FIG. 9, the free ends of the electrical conductors 200 are illustrated and indicate the approximate location of the respective electrodes 530, 532, 534, 536. The electrode assembly 513 includes a lower electrode strip 550 (that includes the electrodes 530, 532, 534, 536) and an opposing cover 560, both of which mate with the other components to form the distal portion 510. The lower electrode strip 550 has a first end 552 and a second end 554. As best shown in FIGS. 9 through 11, the first end 552 has a groove or slot 556 formed therein for receiving the end 202 of the flexible shaft 200. The slot 556 terminates in a shoulder 557 that serves to locate the end 202 and further acts as a stop for preventing further movement of the end 202 in the distal direction.

The lower electrode strip 550 contains the electrodes 530, 532, 534, 536 which are disposed in predetermined locations along the length of the lower electrode strip 550 such that each one of the electrodes is conductively isolated from the other electrodes. Surfaces of the electrodes 530, 532, 534, 536 are exposed to permit the electrodes 530, 532, 534, 536 to contact target brain tissue when the lower electrode strip 550 is placed against the target brain tissue.

The cover 560 is a contoured member having a first end 562 and a second end 564. More specifically, the cover 560 has a general step-like shape having three distinct segments 566, 568, 570. The first segment 566 extends from the first end 562 to a first shoulder 572, the second segment 568 extends from the first shoulder 572 to a second shoulder 574, and the third segment 570 extends from the second shoulder 574 to the second end 564. When viewing the cover 560 from the top, the second segment 568 is recessed relative to the first segment 566 and the third segment 570 is recessed relative to the second segment 568.

The cover 560 is constructed so that the third segment 570 seats against the second end 554 of the lower electrode strip 550, the reinforcing sheath 511 with the electrical conductors 554 of the lower electrode strip 550, the reinforcing sheath 511 with the electrical conductors 200 wrapped therearound and the sleeve 190 are securely disposed between the second segment 568 and the lower electrode strip 550. The sleeve 190 and the core member 540 seat proximate to or in contact with the second shoulder 574 when the electrode assembly 513 is assembled. The distance between the first segment 566 and the lower electrode strip 550 is sufficient to accommodate the flexible shaft 201, whereby the flexible shaft 201 seats within the groove slot 556 formed in the bottom support plate 500. When the lower electrode strip 550 and the cover 560 mate together, the end 202 of the flexible shaft 201 is received within the cavity formed between the first segment 566 and the lower electrode strip 550, with the shoulder 557 and the first shoulder 572 aligning with one another to provide a stop means for preventing the end 202 from moving further in the distal direction. The end 202 can be retained within the cavity formed between the first segment 566 and the lower electrode strip 550 using any number of techniques including filleting an adhesive around the first end 562 of the cover 560 and an outer circumferential surface of the flexible shaft 201. The adhesive thus securely bonds the flexible shaft 201 to both the lower electrode strip 550 and the cover 560.

The third segment 570 is securely coupled to the second end 554 of the lower electrode strip 550 using conventional techniques. For example, the third segment 570 can be bonded to the second end 554 using a bonding agent, such as an adhesive or the like, or another type of process can be used. In this manner when the cover 560 is coupled to the lower electrode strip 550, the electrode assembly 513 is completed and the internal components of the distal portion 510 are securely housed between the cover 560 and the lower electrode strip 550, as well as having the electrodes 530, 532, 534, 536 electrically connected to the lead connection terminals 220, 222, 224, 226 via the electrical conductors.

Figure 17:
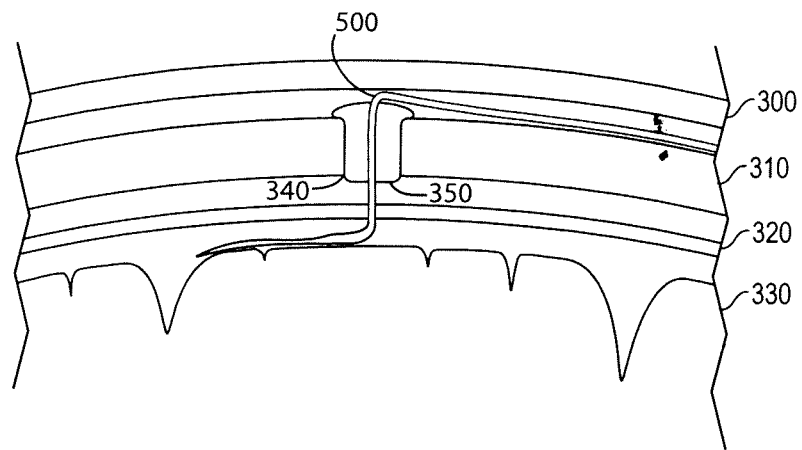
FIG. 17 is an illustration showing the use of the lead of FIG. 9 in an exemplary section of a patient's head, including the patient's brain, dura mater, and cranium.
Figure 18:
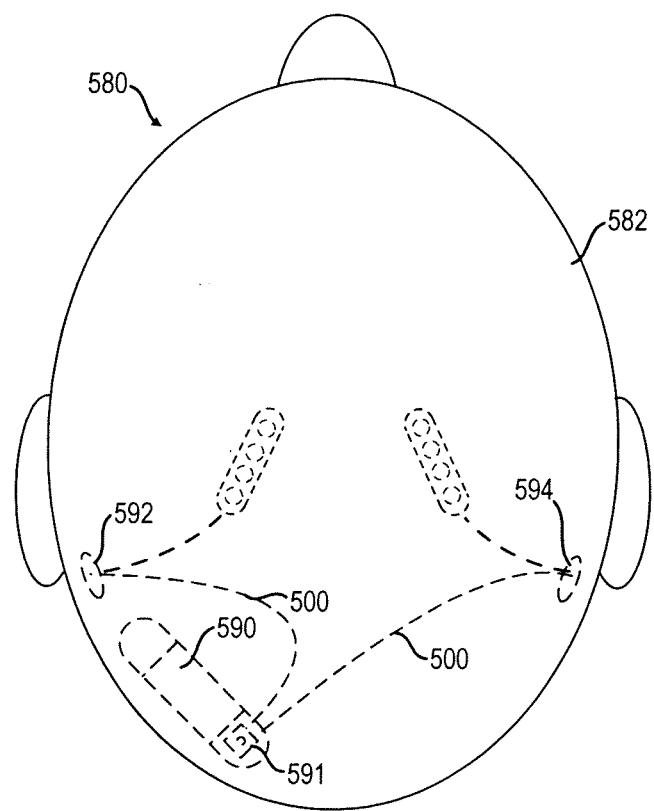
FIG. 18 is a schematic view of an implantable neurostimulator system incorporating the lead of FIG. 9.

Now referring to FIGS. 17 through 18, the lead 500 is illustrated as being used as a surface cortical lead for implantation into the brain. FIG. 17 is a schematic cross-section of the anatomy of a patient's head, illustrating an example of how the lead 500 may be employed. The drawing of FIG. 17 is not to scale, and is not necessarily intended to represent any particular anatomical features or landmarks.

In general, the lead 500 is advantageously situated below a patient's scalp 300, and extends through the patient's cranium 310 and dura mater 320 to access the patient's cortex 330. The lead 500, and more particularly, the lower electrode strip 550 thereof, is inserted into a desired electrode site (target area) depending upon the specific application. Choosing desired electrode sites may be performed at any appropriate stage of the surgical procedure, including presurgically in an operative planning stage; intraoperatively after a craniotomy has been performed or a burr hole has been made; or intraoperatively after one or more other procedures, such as functional mapping, have been performed.

The distal portion 510 is inserted through a burr hole 340 defined in the patient's cranium 310 and preferably surgically formed and then the lower electrode strip 550 is disposed against target brain tissue of the cranium. The lower electrode strip 550 is disposed underneath the dura mater 320 with the disc electrodes 530, 532, 534, 536 contacting the target brain surface. The lead 500 is anchored within the burr hole 340 by way of the burr hole cover 350 inserted within and affixed to the burr hole 340. The burr hole cover 350 is adapted to hold the lead 500 in place and prevent undesired movement of the distal portion 510, even if a force is applied to another portion of the lead 500.

During the above-described insertion process, the stylet 130 remains inserted into the interior of the lead 500 such that it extends along the longitudinal length of the lead 500 from the proximal portion 520 to the distal portion 510. Once the distal portion 510 of the lead 500 and more particularly, the electrodes 530, 532, 534, 536 are disposed in their desired locations, the stylet 130 is removed form the lead 500. The lead 500 remains implanted in place due to the frictional fit between the lead 500 and the surrounding tissue. Moreover, the burr hole cover 350 further serves to hold the lead 500 in place. However, it will be appreciated that the lead 500 can be implanted without the use of the stylet 130.

Figure 19:
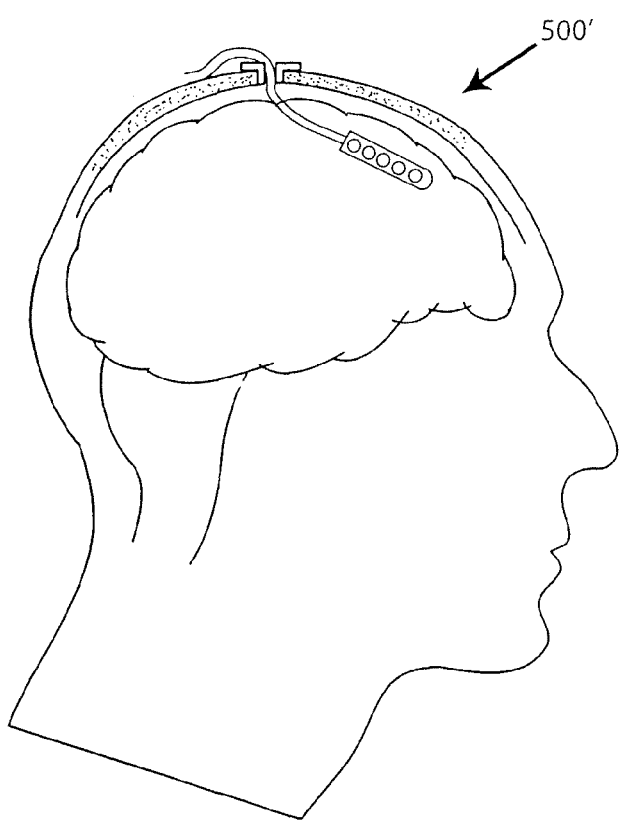
FIG. 19 is another schematic view of an implantable neurostimulator system incorporating the lead of FIG. 9.

FIG. 18 schematically illustrates an exemplary configuration of an implantable system 580 for the treatment of neurological disorders, as it would be generally situated under the scalp of a patient's head 582 and implanted intracranially. The illustrated embodiment of the system 580 has a control module 590 and two leads 500, each of which connects a lead connector 591 on the control module 620 to the plurality of distal electrodes 530, 532, 534, 536 (FIGS. 9-14). It will be appreciated that the control module 590 can be of the type that can be permanently implanted into the patient's cranium in a location where the bone is fairly thick. In an alternative embodiment, the control module 590 can be located in the trunk of the patient's body like a heart pacemaker with the connecting wires being run under the patient's skin. As described above, the disc electrodes 530, 532, 534, 536 are placed on the brain surface at a target location. The leads 500 are run from the control module 590, underneath the patient's scalp 582, through burr holes 592, 594 to the electrodes placed beneath the patient's cranium. Although this embodiment is described as each lead 500 having four disc electrodes 530, 532, 534, 536, it will be appreciated that more (or fewer) than four electrodes with connecting conductors can be used with and by the present leads 500. For example, FIG. 19 is a schematic cross-section of the anatomy of a patient's head, illustrating an example of how a surface cortical lead 500' may be employed, wherein the lead 500' contains five independent electrodes.

Figure 21:
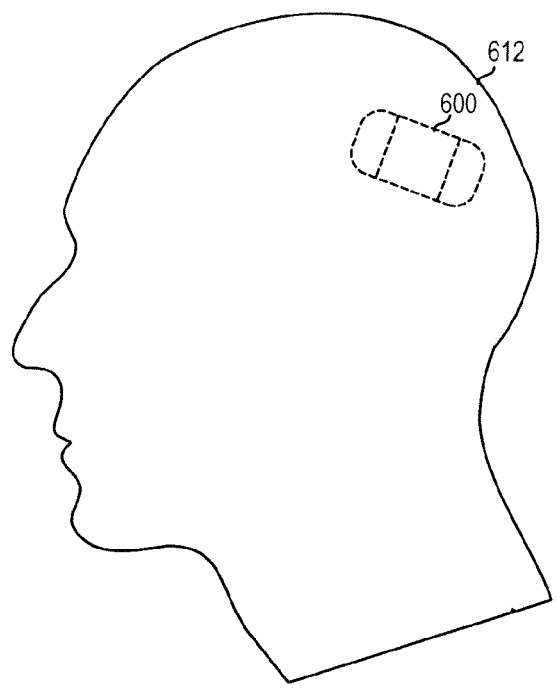
FIG. 21 is a schematic illustration of a patient's head showing the placement of an implantable neurostimulator according to one embodiment.

FIG. 21 depicts an intracranially implanted device 600 which according to one exemplary embodiment is a small self-contained responsive neurostimulator. As the term is used herein, a responsive neurostimulator is a device capable of detecting or predicting ictal activity (or other neurological events) and providing electrical stimulation to neural tissue in response to that activity, where the electrical stimulation is specifically intended to terminate the ictal activity, treat a neurological event, prevent an unwanted neurological event from occurring, or lessen the severity or frequency of certain symptoms of a neurological disorder. As disclosed herein, the responsive neurostimulator detects ictal activity by systems and methods according to the invention.

Preferably, the implantable device is capable of detecting or predicting any kind of neurological event that has a representative electrographic signature. While the disclosed embodiment is described primarily as responsive to epileptic seizures, it should be recognized that it is also possible to respond to other types of neurological disorders, such as movement disorders (e.g., the tremors characterizing Parkinson's disease), migraine headaches, chronic pain, and neuropsychiatric disorders such as depression. Preferably, neurological events representing any or all of these afflictions can be detected when they are actually occurring, in an onset stage, or as a predictive precursor before clinical symptoms begin.

Figure 22:
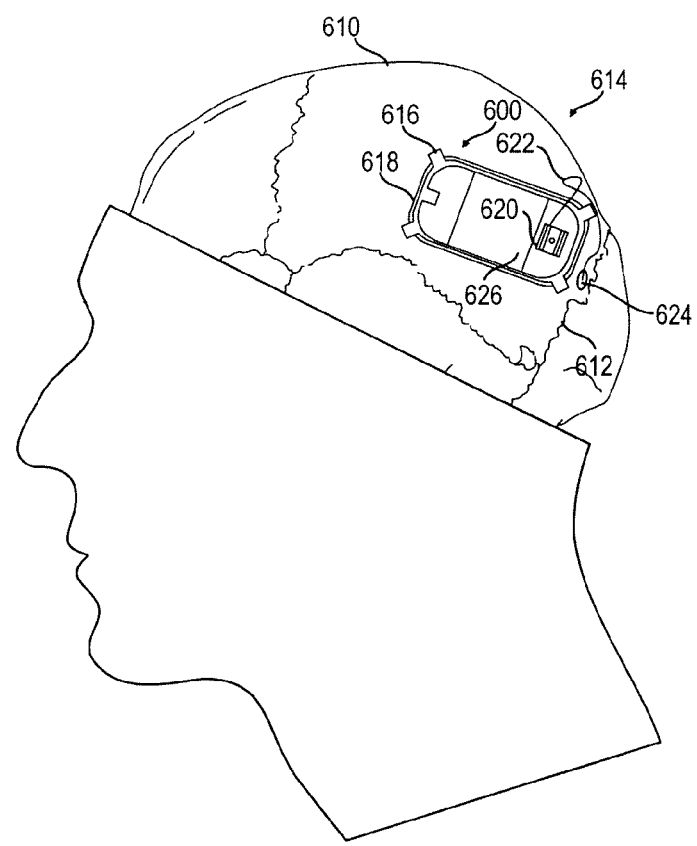
FIG. 22 is a schematic illustration of a patient's cranium showing the implantable neurostimulator of FIG. 1 as implanted, including leads extending to the patient's brain.

In the disclosed embodiment, the neurostimulator is implanted intracranially in a patient's parietal bone 610, in a location anterior to the lambdoidal suture 612 (see FIG. 22). It should be noted, however, that the placement described and illustrated herein is merely exemplary, and other locations and configurations are also possible, in the cranium or elsewhere, depending on the size and shape of the device and individual patient needs, among other factors. The device 600 is preferably configured to fit the contours of the patient's cranium 614. In an alternative embodiment, the device 600 is implanted under the patient's scalp 612 but external to the cranium; it is expected, however, that this configuration would generally cause an undesirable protrusion in the patient's scalp where the device is located. In yet another embodiment, when it is not possible to implant the device intracranially, it may be implanted pectorally (not shown), with leads extending through the patient's neck and between the patient's cranium and scalp, as necessary.

It should be recognized that the embodiment of the device 600 described and illustrated herein is preferably a responsive neurostimulator for detecting and treating epilepsy by detecting seizures or their onsets or precursors, and preventing and or terminating such epileptic seizures.

In an alternative embodiment of the invention, the device 600 is not a responsive neurostimulator, but is an apparatus capable of detecting neurological conditions and events and performing actions in response thereto. The actions performed by such an embodiment of the device 600 need not be therapeutic, but may involve data recording or transmission, providing warnings to the patient, or any of a number of known alternative actions. Such a device will typically act as a diagnostic device when interfaced with external equipment, as will be discussed in further detail below.

The device 600, as implanted intracranially, is illustrated in greater detail in FIG. 22. The device 600 is affixed in the patient's cranium 614 by way of a ferrule 616. The ferrule 616 is a structural member adapted to fit into a cranial opening, attach to the cranium 614, and retain the device 600.

To implant the device 600, a craniotomy is performed in the parietal bone anterior to the lambdoidal suture 612 to define an opening 618 slightly larger than the device 600. The ferrule 616 is inserted into the opening 618 and affixed to the cranium 614, ensuring a tight and secure fit. The device 600 is then inserted into and affixed to the ferrule 616.

As shown in FIG. 22, the device 600 includes a lead connector 620 adapted to receive one or more electrical leads, such as a first lead 622. It will be appreciated that the first lead 622 can be in the form of the reinforced depth lead 100 of FIG. 1 or the reinforced cortical lead of FIG. 9. The lead connector 620 acts to physically secure the lead 622 to the device 600, and facilitates electrical connection between a conductor in the lead 622 coupling an electrode to circuitry within the device 600. The lead connector 620 accomplishes this in a substantially fluid-tight environment with biocompatible materials.

The lead 622, as illustrated, and other leads for use in a system or method according to the present embodiments, is a flexible elongated member having one or more conductors (i.e., lead 100 of FIG. 1 and lead 500 of FIG. 9). As shown, the lead 622 is coupled to the device 600 via the lead connector 620, and is generally situated on the outer surface of the cranium 614 (and under the patient's scalp 612), extending between the device 600 and a burr hole 624 or other cranial opening, where the lead 622 enters the cranium 614 and is coupled to a depth electrode (see FIG. 24) implanted in a desired location in the patient's brain. If the length of the lead 622 is substantially greater than the distance between the device 600 and the burr hole 624, any excess may be urged into a coil configuration under the scalp 612. As described in U.S. Pat. No. 6,006,124 to Fischell, et al., which is hereby incorporated by reference as though set forth in full herein, the burr hole 624 is sealed after implantation to prevent further movement of the lead 622; in an embodiment of the invention, a burr hole cover apparatus is affixed to the cranium 614 at least partially within the burr hole 624 to provide this functionality.

The device 600 includes a durable outer housing 626 fabricated form a biocompatible material. Titanium, which is light, extremely strong, and biocompatible, is used in analogous devices, such as cardiac pacemakers, and would serve advantageously in this context. As the device 600 is self-contained, the housing 626 encloses a battery and any electronic circuitry necessary or desirable to provide the functionality described herein, as well as any other features. As will be described in further detail below, a telemetry coil may be provided outside of the housing 626 (and potentially integrated with the lead connector 620) to facilitate communication between the device 600 and external devices.

The neurostimulator configuration described herein and illustrated in FIG. 22 provides several advantages over alternative designs. First, the self-contained nature of the neurostimulator substantially decreases the need for access to the device 600, allowing the patient to participate in normal life activities. Its small size and intracranial placement causes a minimum of cosmetic disfigurement. The device 600 will fit in an opening in the patient's cranium, under the patient's scalp, with little noticeable protrusion or bulge. The ferrule 616 used for implantation allows the craniotomy to be performed and fit verified without the possibility of breaking the device 600, and also provides protection against the device 600 being pushed into the brain under external pressure or impact. A further advantage is that the ferrule 616 receives any cranial bone growth, so at explant, the device 600 can be replaced without removing any bone screws—only the fasteners retaining the device 600 in the ferrule 616 need be manipulated.

Figure 23:
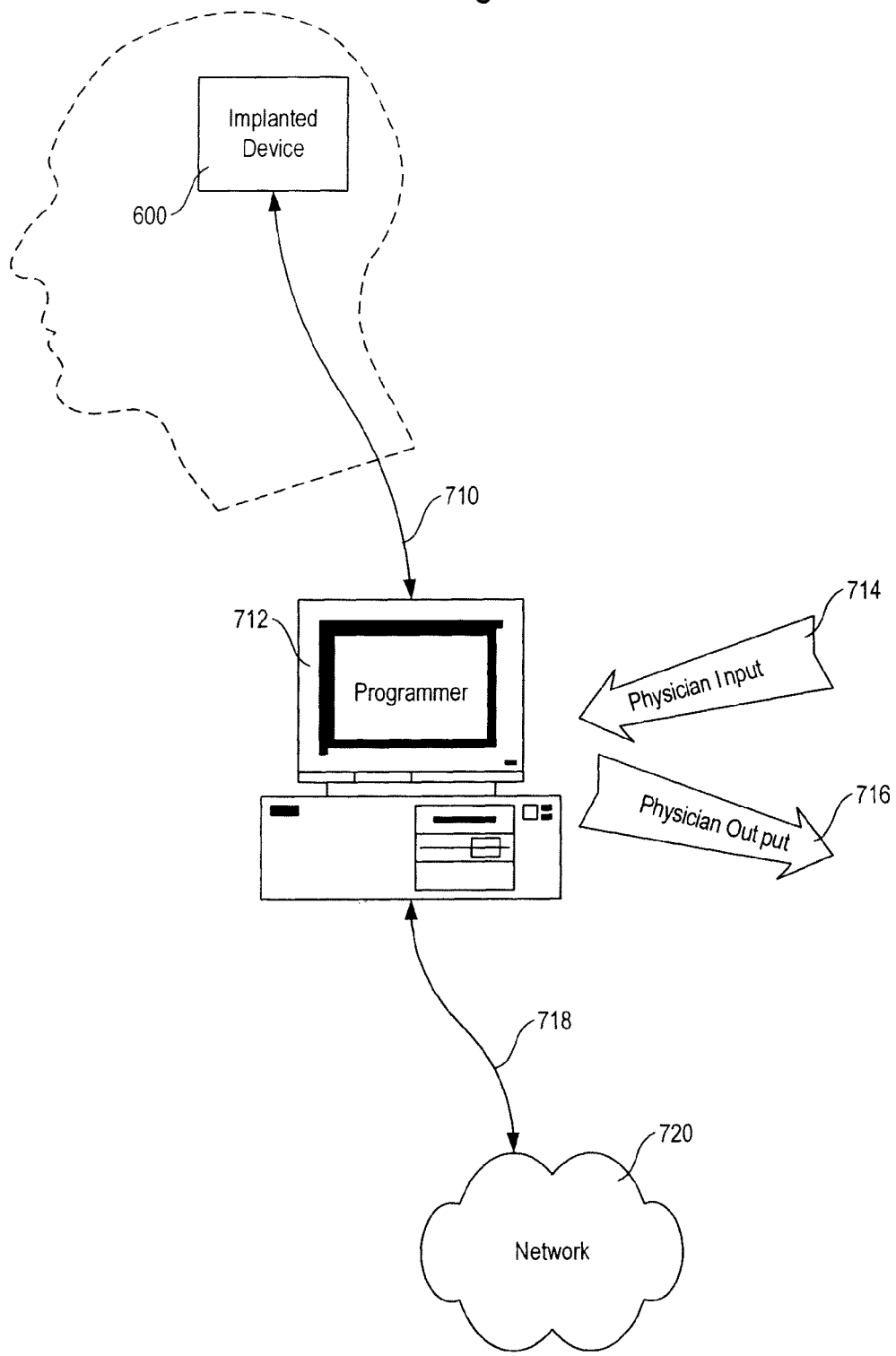
FIG. 23 is a block diagram illustrating context in which an implantable neurostimulator according to one embodiment being implanted and operated.

As stated above, and as illustrated in FIG. 23, a neurostimulator according to the invention operates in conjunction with external equipment. The device 600 is mostly autonomous (particularly when performing its usual sensing, detection, and stimulation capabilities), but preferably includes a selectable part-time wireless link 710 to external equipment such as a programmer 712. In the disclosed embodiment of the invention, the wireless link 710 is established by moving a wand (or other apparatus) having communication capabilities and coupled to the programmer 712 into range of the device 600. The programmer 712 can then be used to manually control the operation of the device 600, as well as to transmit information to or receive information from the device 600. Several specific capabilities and operations performed by the programmer 712 in conjunction with the device 600 will be described in further detail below.

The programmer 712 is capable of performing a number of advantageous operations in connection with the invention. In particular, the programmer 712 is able to specify and set variable parameters in the device 600 to adapt the function of the device 600 to meet the patient's needs, download or receive data (including but not limited to stored EEG waveforms, parameters, or logs of actions taken) from the device 600 to the programmer 712, upload or transmit program code and other information from the programmer 712 to the device 600, or command the device 600 to perform specific actions or change modes as desired by a physician operating the programmer 712. To facilitate these functions, the programmer 712 is adapted to receive physician input 714 and provide physician output 716; data is transmitted between the programmer 712 and the device 600 over the wireless link 710.

The programmer 712 may be coupled via a communication link 718 to a network 720 such as the Internet. This allows any information downloaded from the device 600, as well as any program code or other information to be uploaded to the device 600, to be stored in a database at one or more data repository locations (which may include various servers and network-connected programmers like the programmer 712). This would allow a patient (and the patient's physician) to have access to important data, including past treatment information and software updates, essentially anywhere in the world that there is a programmer (like the programmer 712) and a network connection.

The programmer 712 may be coupled via a communication link 718 to a network 720 such as the Internet. This allows any information downloaded from the device 600, as well as any program code or other information to be uploaded to the device 600, to be stored in a database at one or more data repository locations (which may include various servers and network-connected programmers like the programmer 712). This would allow a patient (and the patient's physician) to have access to important data, including past treatment information and software updates, essentially anywhere in the world that there is a programmer (like the programmer 712) and a network connection.

Figure 24:
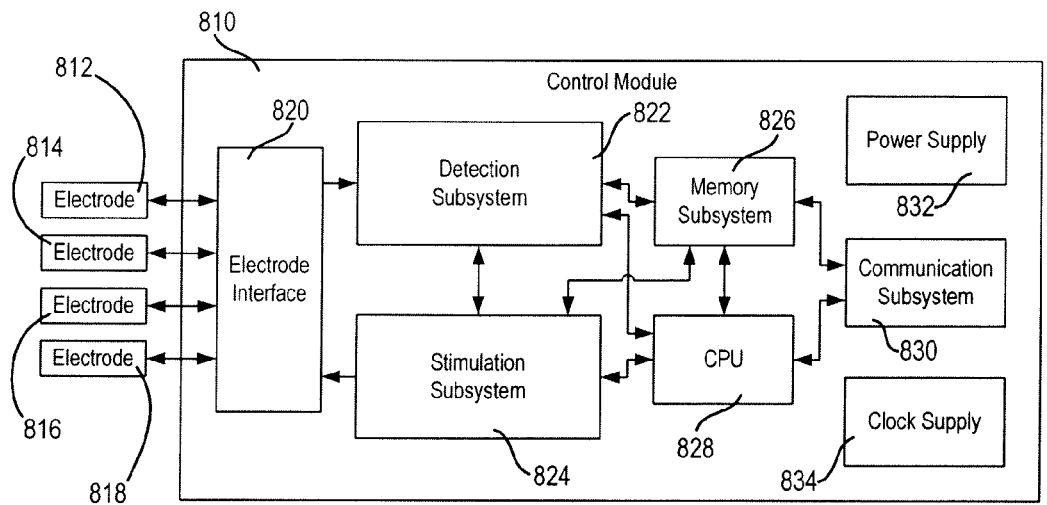
FIG. 24 is a block diagram illustrating the major functional subsystems of an implantable neurostimulator according to one embodiment.

An overall block diagram of the device 600 used for measurement, detection, and treatment according to the invention is illustrated in FIG. 24. Inside the housing 626 of the device 600 are several subsystems making up a control module 810. The control module 810 is capable of being coupled to a plurality of electrodes 812, 814, 816, 818 (each of which may be connected to the control module 810 via a lead that is analogous or identical to the lead 622 of FIG. 22) for sensing and stimulation. In the illustrated embodiment, the coupling is accomplished through the lead connector 620 (FIG. 22). Although four electrodes are shown in FIG. 24, it should be recognized that any number is possible, and in the embodiment described in detail below, eight electrodes are used. In fact, it is possible to employ an embodiment of the invention that uses a single lead with at least two electrodes, or two leads each with a single electrode (or with a second electrode provided by a conductive exterior portion of the housing 626 in one embodiment), although bipolar sensing between two closely spaced electrodes on a lead is preferred to minimize common mode signals including noise.

The electrodes 812-818 are connected to an electrode interface 820. Preferably, the electrode interface is capable of selecting each electrode as required for sensing and stimulation; accordingly the electrode interface is coupled to a detection subsystem 822 and a stimulation subsystem 824. The electrode interface also may provide any other features, capabilities, or aspects, including but not limited to amplification, isolation, and charge-balancing functions, that are required for a proper interface with neurological tissue and not provided by any other subsystem of the device 600.

The detection subsystem 822 includes an EEG analyzer function. The EEG analyzer function is adapted to receive EEG signals from the electrodes 812-818, through the electrode interface 820, and to process those EEG signals to identify neurological activity indicative of a seizure, an onset of a seizure, or a precursor to a seizure. One way to implement such EEG analysis functionality is disclosed in detail in U.S. Pat. No. 6,016,449 to Fischell et al., incorporated by reference above; additional inventive methods are described in detail below. The detection subsystem may optionally also contain further sensing and detection capabilities, including but not limited to parameters derived from other physiological conditions (such as electrophysiological parameters, temperature, blood pressure, etc.).

The stimulation subsystem 824 is capable of applying electrical stimulation to neurological tissue through the electrodes 812-818. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal events detected by the EEG analyzer function of the detection subsystem 822. As illustrated in FIG. 24, the stimulation subsystem 824 and the EEG analyzer function of the detection subsystem 822 are in communication; this facilitates the ability of stimulation subsystem 824 to provide responsive stimulation as well as an ability of the detection subsystem 822 to blank the amplifiers while stimulation is being performed to minimize stimulation artifacts. It is contemplated that the parameters of the stimulation signal (e.g., frequency, duration, waveform) provided by the stimulation subsystem 824 would be specified by other subsystems in the control module 810, as will be described in further detail below.

Also in the control module 810 is a memory subsystem 826 and a central processing unit (CPU) 828, which can take the form of a microcontroller. The memory subsystem is coupled to the detection subsystem 822 (e.g., for receiving and storing data representative of sensed EEG signals and evoked responses), the stimulation subsystem 824 (e.g., for providing stimulation waveform parameters to the stimulation subsystem), and the CPU 828, which can control the operation of the memory subsystem 826. In addition to the memory subsystem 826, the CPU 828 is also connected to the detection subsystem 822 and the stimulation subsystem 824 for direct control of those subsystems.

Also provided in the control module 810, and coupled to the memory subsystem 826 and the CPU 828, is a communication subsystem 830. The communication subsystem 830 enables communication between the device 610 (FIG. 21) and the outside world, particularly the external programmer 612 (FIG. 23). As set forth above, the disclosed embodiment of the communication subsystem 830 includes a telemetry coil (which may be situated outside of the housing 626) enabling transmission and reception of signals, to or from an external apparatus, via inductive coupling. Alternative embodiments of the communication subsystem 830 could use an antenna for an RF link or an audio transducer for an audio link.

Rounding out the subsystems in the control module 810 are a power supply 832 and a clock supply 834. The power supply 832 supplies the voltages and currents necessary for each of the other subsystems. The clock supply 834 supplies substantially all of the other subsystems with any clock and timing signals necessary for their operation.

It should be observed that while the memory subsystem 826 is illustrated in FIG. 24 as a separate functional subsystem, the other subsystems may also require various amounts of memory to perform the functions described above and others. Furthermore, while the control module 810 is preferably a single physical unit contained within a single physical enclosure, namely the housing 626 (FIG. 22), it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 828 and the other functional subsystems may also vary—the functional distinctions illustrated in FIG. 24 may not reflect the integration of functions in a real-world system or method according to the invention.

Figure 25:
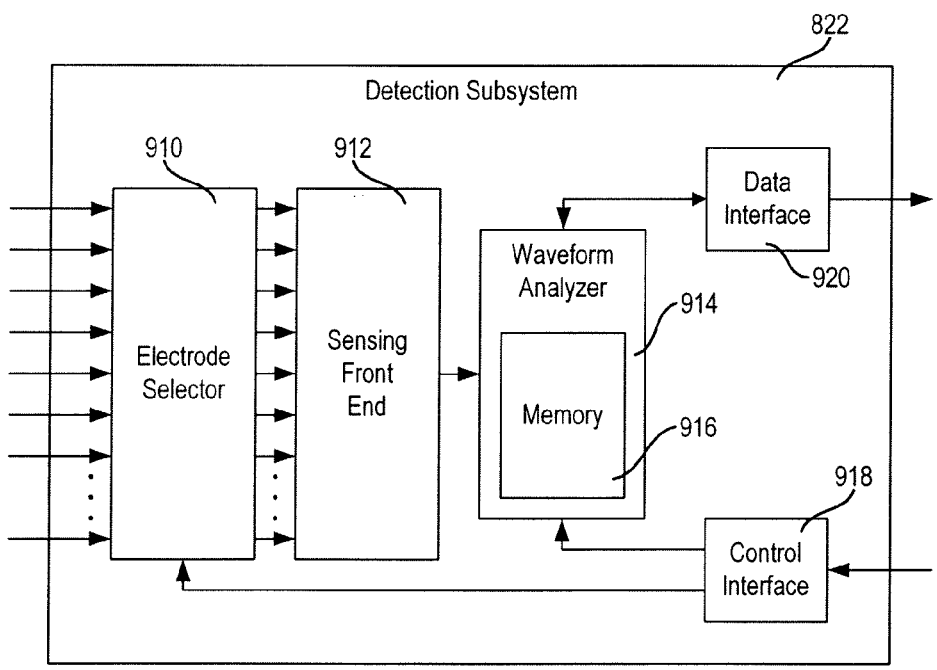
FIG. 25 is a block diagram illustrating the functional components of the detection subsystem of the implantable neurostimulator shown in FIG. 24.

FIG. 25 illustrates details of the detection subsystem 822 (FIG. 24). Inputs from the electrodes 812-818 are on the left, and connections to other subsystems are on the right.

Signals received from the electrodes 812-818 (as routed through the electrode interface 820) are received in an electrode selector 910. The electrode selector 910 allows the device to select which electrodes (of the electrodes 812-818) should be routed to which individual sensing channels of the detection subsystem 822, based on commands received through a control interface 918 from the memory subsystem 826 or the CPU 828 (FIG. 24). Preferably, each sensing channel of the detection subsystem 822 receives a bipolar signal representative of the difference in electrical potential between two selectable electrodes. Accordingly, the electrode selector 910 provides signals corresponding to each pair of selected electrodes (of the electrodes 812-818) to a sensing front end 912, which performs amplification, analog to digital conversion, and multiplexing functions on the signals in the sensing channels. The sensing front end will be described further below in connection with FIG. 26.

A multiplexed input signal representative of all active sensing channels is then fed from the sensing front end 912 to a waveform analyzer 914. The waveform analyzer 914 is preferably a special-purpose digital signal processor (DSP) adapted for use with the invention, or in an alternative embodiment, may comprise a programmable general purpose DSP. In the disclosed embodiment, the waveform analyzer has its own scratchpad memory area 916 used for local storage of data and program variables when the signal processing is being performed. In either case, the signal processor performs suitable measurement and detection methods described generally above and in greater detail below. Any results from such methods, as well as an digitized signals intended for storage transmission to external equipment, are passed to various other subsystems of the control module 910, including the memory subsystem 826 and the CPU 828 (FIG. 24) through a data interface 920. Similarly, the control interface 918 allows the waveform analyzer 914 and the electrode selector 910 to be in communication with the CPU 828.

Figure 26:
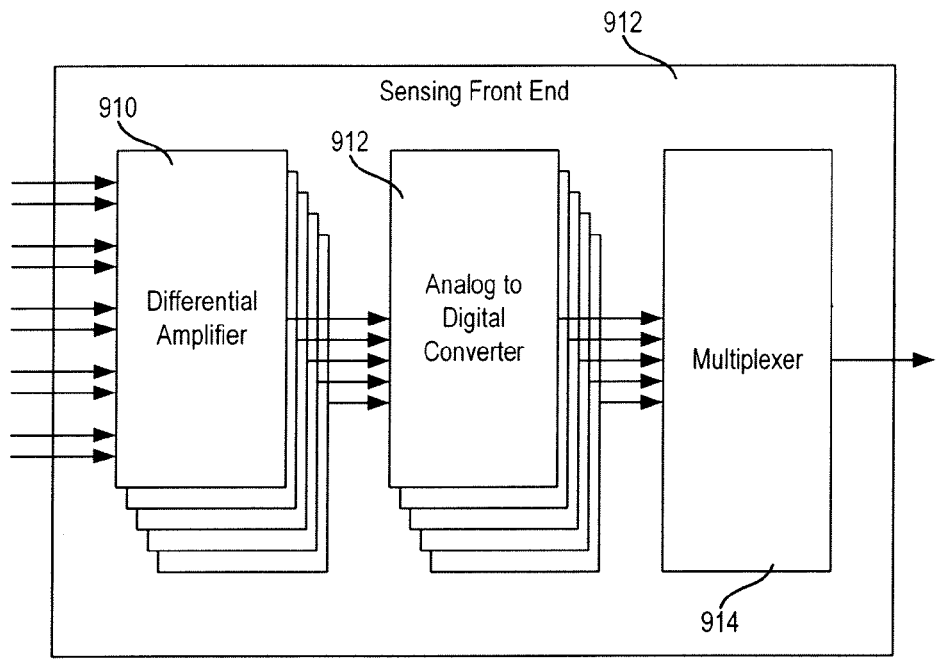
FIG. 26 is a block diagram illustrating the functional components of the waveform analyzer of the detection subsystem of FIG. 25.

Referring now to FIG. 26, the sensing front end 912 (FIG. 25) is illustrated in further detail. As shown, the sensing front end includes a plurality of differential amplifier channels 910, each of which receives a selected pair of inputs from the electrode selector 910. In a preferred embodiment of the invention, each of differential amplifier channels 910 is adapted to receive or to share inputs with one or more other differential amplifier channels 910 without adversely affecting the sensing and detection capabilities of a system according to the invention. Specifically, in an embodiment of the invention, there are at least eight electrodes, which can be mapped separately to eight differential amplifier channels 910 representing eight different sensing channels and capable of individually processing eight bipolar signals, each of which represents an electrical potential difference between two monopolar input signals received from the electrodes and applied to the sensing channels via the electrode selector 910. For clarity, only five channels are illustrated in FIG. 26, but it should be noted that any practical number of sensing channels may be employed in a system according to the invention.

Each differential amplifier channel 910 feeds a corresponding analog to digital converter (ADS) 912. Preferably, the analog to digital converters 912 are separately programmable with respect to sample rates—in the disclosed embodiment, the ADCs 912 convert analog signals into 10-bit unsigned integer digital data streams at a sample rate selectable between 250 Hz and 500 Hz. In several of the illustrations described below where waveforms are shown, sample rates of 250 Hz are typically used for simplicity. However, the invention shall not be deemed to be so limited, and numerous sample rate and resolution options are possible, with tradeoffs known to individuals of ordinary skill in the art of signal processing. The resulting digital signals are received by a multiplexer 914 that creates a single interleaved digital data stream representative of the data from all active sensing channels. As will be described in further detail below, not all of the sensing channels need to be used at one time, and it may in fact be advantageous in certain circumstances to deactivate certain sensing channels to reduce the power consumed by a system according to the invention.

It should be noted that as illustrated and described herein, a "sensing channel" is not necessarily a single physical or functional item that can be identified in any illustration. Rather, a sensing channel is formed from the functional sequence of operations described herein, and particularly represents a single electrical signal received from any pair or combination of electrodes, as preprocessed by a system according to the invention; in both analog and digital forms. See, e.g., U.S. patent application Ser. No. 09 517,797 to D. Fischell et al., filed on Mar. 2, 2000 and entitled "Neurological Event Detection Using Processed Display Channel Based Algorithms and Devices Incorporating These Procedures," which is hereby incorporated by reference as though set forth in full herein. At times (particularly after the multiplexer 914), multiple sensing channels are processed by the same physical and functional components of the system; notwithstanding that, it should be recognized that unless the description herein indicates to the contrary, a system according to the invention processes, handles, and treats each sensing channel independently.

The interleaved digital data stream is passed from the multiplexer 914, out of the sensing front end 912, and into the waveform analyzer 914. The waveform analyzer 914 is illustrated in detail in FIG. 27.

The interleaved digital data stream representing information from all of the active sensing channels is first received by a channel controller 1010. The channel controller applies information from the active sensing channels to a number of wave morphology analysis units 1012 and window analysis units 1014. It is preferred to have as many wave morphology analysis units 1012 and window analysis units 1014 as possible, consistent with the goals of efficiency, size, and low power consumption necessary for an implantable device. In a presently preferred embodiment of the invention, there are sixteen wave morphology analysis units 1012 and eight window analysis units 1014, each of which can receive data from any of the sensing channels of the sensing front end 912, and each of which can be operated with different and independent parameters, including differing sample rates, as will be discussed in further detail below.

Each of the wave morphology analysis units 1012 operates to extract certain feature information from an input waveform as described below in conjunction with FIGS. 29-31. Similarly, each of the window analysis units 1014 performs certain data reduction and signal analysis within time windows in the manner described in conjunction with FIGS. 32-37. Output data from the various wave morphology analysis units 1012 and window analysis units 1014 are combined via an event detector logic 1016. The event detector logic 1016 and the channel controller 1010 are controlled by control commands 1018 received from the control interface 918 (FIG. 25).

A "detection channel," as the term is used herein, refers to a data stream including the active sensing front end 912 and the analysis units of the waveform analyzer 914 processing that data stream, in both analog and digital forms. It should be noted that each detection channel can receive data from a single sensing channel; each sensing channel preferably can be applied to the input of any combination of detection channels. The latter selection is accomplished by the channel controller 1010. As with the sensing channels, not all detection channels need to be active; certain detection channels can be deactivated to save power or if additional detection processing is deemed unnecessary in certain applications.

In conjunction with the operation of the wave morphology units 1012 and the window analysis units 1014, a scratchpad memory area 916 is provided for temporary storage of processed data. The scratchpad memory area 916 may be physically part of the memory subsystem 826, or alternatively may be provided for the exclusive use of the waveform analyzer 914. Other subsystems and components of a system according to the invention may also be furnished with a local scratchpad memory, if such a configuration is advantageous.

Figure 28:
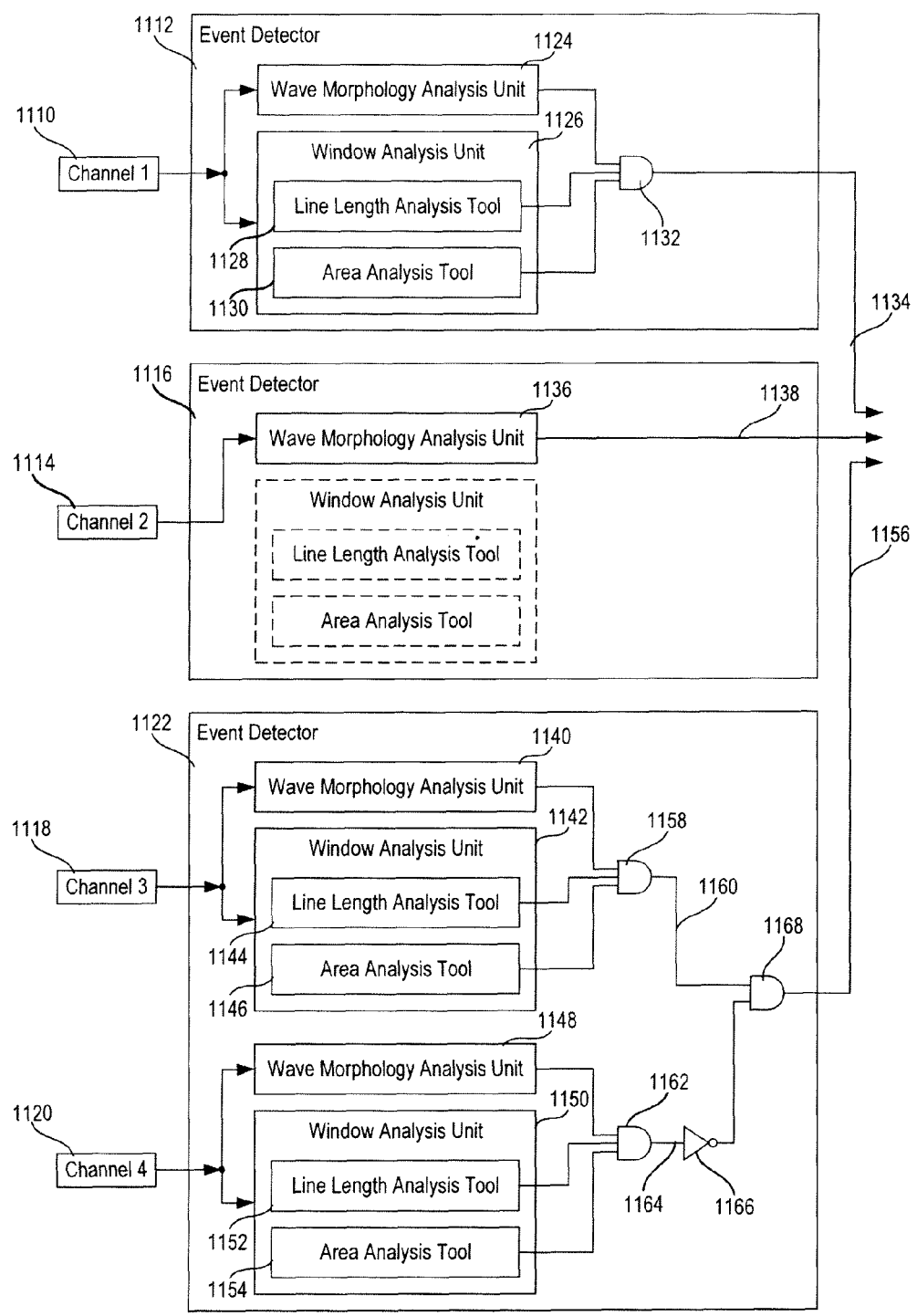
FIG. 28 is a block diagram illustrating the functional arrangement of components of the waveform analysis of the detection subsystem of FIG. 25 in one possible programmed embodiment.

The operation of the event detector logic 1016 is illustrated in detail in the functional block diagram of FIG. 28, in which four exemplary sensing channels are analyzed by three illustrative event detectors.

A first sensing channel 1110 provides input to a first event detector 1112. While the first event detector 1112 is illustrated as a functional block in the block diagram of FIG. 28, it should be recognized that it is a functional block only for purposes of illustration, and may not have any physical counterpart in a device according to the invention. Similarly, a second sensing channel 1114 provides input to a second event detector 1016, and a third input channel 1118 and a fourth input channel 1120 both provide input to a third event detector 1122.

Figure 27:
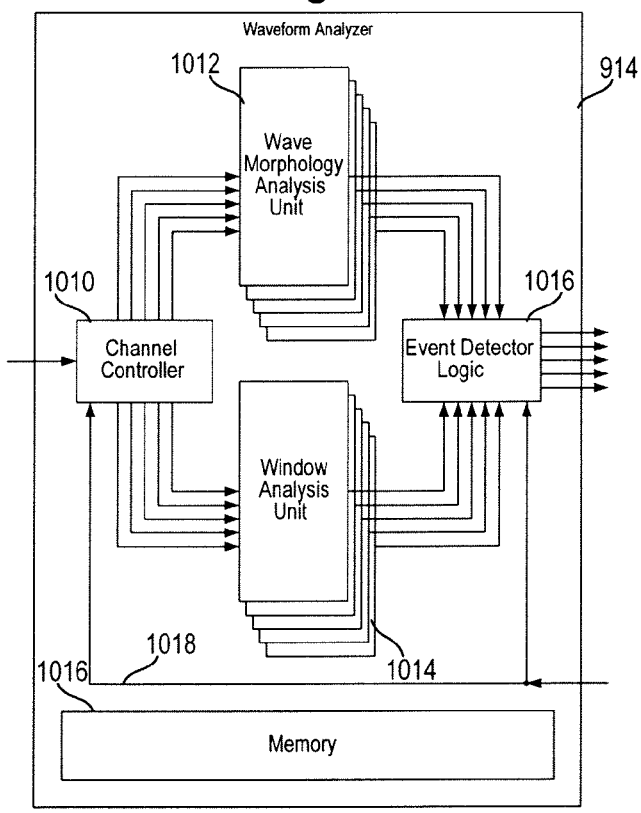
FIG. 27 is a block diagram illustrating the components of the waveform analyzer of the detection subsystem of FIG. 25.

Considering the processing performed by the event detectors 1112, 1116, and 1122, the first input channel 1110 feeds a signal to both a wave morphology analysis unit 1124 (one of the wave morphology analysis units 1012 of FIG. 27) and a window analysis unit 1126 (one of the window analysis units 1014 of FIG. 27). The window analysis unit 1126, in turn, includes a line length analysis tool 1128 and an area analysis tool 1130. As will be discussed in detail below, the line length analysis tool 1128 and the area analysis tool 1130 analyze different aspects of the signal from the first input channel 1110.

Outputs from the wave morphology analysis unit 1124, the line length analysis tool 1128, and the area analysis tool 1130 are combined in a Boolean AND operation 1132 and sent to an output 1134 for further use by a system. For example, if a combination of analysis tools in an event detector identifies several simultaneous (or near-simultaneous) types of activity in an input channel, a system according to the exemplary embodiment may be programmed to perform an action in response thereto. Details of the analysis tools and the combination processes used in event detectors according to the invention will be set forth in greater detail below.

In the second event detector 1116, only a wave morphology analysis unit 1136 is active. Accordingly, no Boolean operation needs to be performed, and the wave morphology analysis unit 1136 directly feeds an event detector output 1138.

The third event detector 1122 operates on two input channels 1118 and 1120 and includes two separate detection channels of analysis units: a first wave morphology analysis unit 1140 and a first window analysis unit 1142, the latter including a first line length analysis tool 1144 and a first area analysis tool 1146; and a second wave morphology analysis unit 1148 and a second window analysis unit 1150, the latter including a second line length analysis tool 1152 and a second area analysis tool 1154. The two detection channels of analysis units are combined to provide a single event detector output 1156.

In the first detection channel of analysis units 1140 and 1142, outputs from the first wave morphology analysis unit 1140, the first line length analysis tool 1144, and the first area analysis tool 1146 are combined via a Boolean AND operation 1158 into a first detection channel output 1160. Similarly, in the second detection channel of analysis units 1148 and 1150, outputs from the second wave morphology analysis unit 1148, the second line length analysis tool 1152, and the second area analysis tool 1154 are combined via a Boolean AND operation 1162 into a second detection channel output 1164. In the illustrated embodiment of the invention, the second detection channel output 1164 is invertible with selectable Boolean logic inversion 1166 before it is combined with the first detection channel output 1160. Subsequently, the first detection channel output 1160 and the second detection channel output 1164 are combined with a Boolean AND operation 1168 to provide a signal to the output 1156. In an alternative embodiment, a Boolean OR operation is used to combine the first detection channel output 1160 and the second detection channel output 1164.

In one embodiment of the invention, the second detection channel (analysis units 1148 and 1150) represents a "qualifying channel" with respect to the first detection channel (analysis units 1140 and 1142). In general, a qualifying channel allows a detection to be made only when both channels are in concurrence with regard to detection of an event. For example, a qualifying channel can be used to indicate when a seizure has "generalized," i.e., spread through a significant portion of a patient's brain. To do this, the third input channel 1118 and the fourth input channel 1120 are configured to receive EEG waveforms from separate amplifier channels coupled to electrodes in separate parts of the patient's brain (e.g., in opposite hemispheres). Accordingly, then, the Boolean AND operation 1168 will indicate a detection only when the first detection output 1160 and the second detection output 1164 both indicate the presence of an event (or, when Boolean logic inversion 1166 is present, when the first detection output 1160 indicates the presence of an event while the second detection output 1164 does not). As will be described in further detail below, the detection outputs 1160 and 1164 can be provided with selectable persistence (i.e., the ability to remain triggered for some time after the event is detected), allowing the Boolean AND combination 1168 to be satisfied even when there is not precise temporal synchronization between detections on the two channels.

It should be appreciated that the concept of a "qualifying channel" allows the flexible configuration of a device 600 according to one exemplary embodiment to achieve a number of advantageous results. In addition to the detection of generalization, as described above, a qualifying channel can be configured, for example, to detect noise so a detection output is valid only when noise is not present, to assist in device configuration in determining which of two sets of detection parameters is preferable (by setting up the different parameters in the first detection channel and the second detection channel, then replacing the Boolean AND combination with a Boolean OR combination), or to require a specific temporal sequence of detections (which would be achieved in software by the CPU 1128 after a Boolean OR combination of detections). There are numerous other possibilities.

The outputs 1134, 1138, and 1156 of the event detectors are preferably represented by Boolean flags, and as described below, provide information for the operation of a system according to the invention.

While FIG. 28 illustrates four different sensing channels providing input to four separate detection channels, it should be noted that a maximally flexible embodiment of the present invention would allow each sensing channel to be connected to one or more detection channels. It may be advantageous to program the different detection channels with different settings (e.g., thresholds) to facilitate alternate "views" of the same sensing channel data stream.

FIG. 29 illustrates three representative waveforms of the type expected to be manipulated by as system according to the invention. It should be noted, however, that the waveforms illustrated in FIG. 29 are illustrative only, and are not intended to represent any actual data. The first waveform 1210 is representative of an unprocessed electroencephalogram (EEG) or electrocorticogram (ECoG) waveform having a substantial amount of variability; the illustrated segment has a duration of approximately 160 ms and a dominant frequency (visible as the large-scale crests and valleys) of approximately 12.5 Hz. It will be recognized that the first waveform is rather rough and peaky; there is a substantial amount of high-frequency energy represented therein.

The second waveform 1212 represents a filtered version of the original EEG waveform 1210. As shown, most of the high-frequency energy has been eliminated from the signal, and the waveform 1212 is significantly smoother. In the disclosed embodiment of the invention, this filtering operation is performed in the sensing front end 912 before the analog to digital converters 1012 (FIG. 26).

The filtered waveform 1212 is then sampled by one of the analog to digital converters 1012; this operation is represented graphically in the third waveform 1214 of FIG. 29. As illustrated, a sample rate used in an embodiment of the invention is 250 Hz (4 ms sample duration), resulting in approximately 40 samples over the illustrated 160 ms segment. As is well known in the art of digital signal processing, the amplitude resolution of each sample is limited; in the disclosed embodiment, each sample is measured with a resolution of 10 bits (or 1024 possible values). As is apparent upon visual analysis of the third waveform, the dominant frequency component has a wavelength of approximately 20 samples, which corresponds to the dominant frequency of 12.5 Hz.

Referring now to FIG. 30, the processing of the wave morphology analysis units 1112 is described in conjunction with a filtered and sampled waveform 1310 of the type illustrated as the third waveform 1214 of FIG. 29.

In a first half wave 1312, which is partially illustrated in FIG. 30 the starting point occurs before the illustrated waveform segment 1310 begins), the waveform segment 1310 is essentially monotonically decreasing, except for a small first perturbation 1314. Accordingly, the first half wave 1312 is represented by a vector from the starting point (not shown) to a first local extremum 1316, where the waveform starts to move in the opposite direction. The first perturbation 1314 is of insufficient amplitude to be considered a local extremum, and is disregarded by a hysteresis mechanism (discussed in further detail below). A second half wave 1318 extends between the first local extremum 1316 and a second local extremum 1320. Again, a second perturbation 1322 is of insufficient amplitude to be considered an extremum. Likewise, a third half wave 1324 extends between the second local extremum 1320 and a third local extremum 1326; this may appear to be a small perturbation, but is greater in amplitude than a selected hysteresis threshold. The remaining half waves 1328, 1330, 1332, 1334, and 1336 are identified analogously. As will be discussed in further detail below, each of the identified half waves 1312, 1318, 1324, 1328, 1330, 1332, 1334, and 1336 has a corresponding duration 1338, 1340, 1342, 1344, 1346, 1348, 1350, and 1352, respectively, and analogously, a corresponding amplitude determined from the relative positions of each half wave's starting point and ending point along the vertical axis, and a slope direction, increasing or decreasing.

In a method performed according to one embodiment, it is particularly advantageous to allow for a programmable hysteresis setting in identifying the ends of half waves. In other words, as explained above, the end of an increasing or decreasing half wave might be prematurely identified as a result of quantization (and other) noise, low-amplitude signal components, and other perturbing factors, unless a small hysteresis allowance is made before a reversal of waveform direction (and a corresponding half wave end) is identified. Hysteresis allows for insignificant variations in a signal level inconsistent with the signal's overall movement to be ignored without the need for extensive further signal processing such as filtering. Without hysteresis, such small and insignificant variations might lead to substantial and gross changes in where half waves are identified, leading to unpredictable results.

Figure 31:
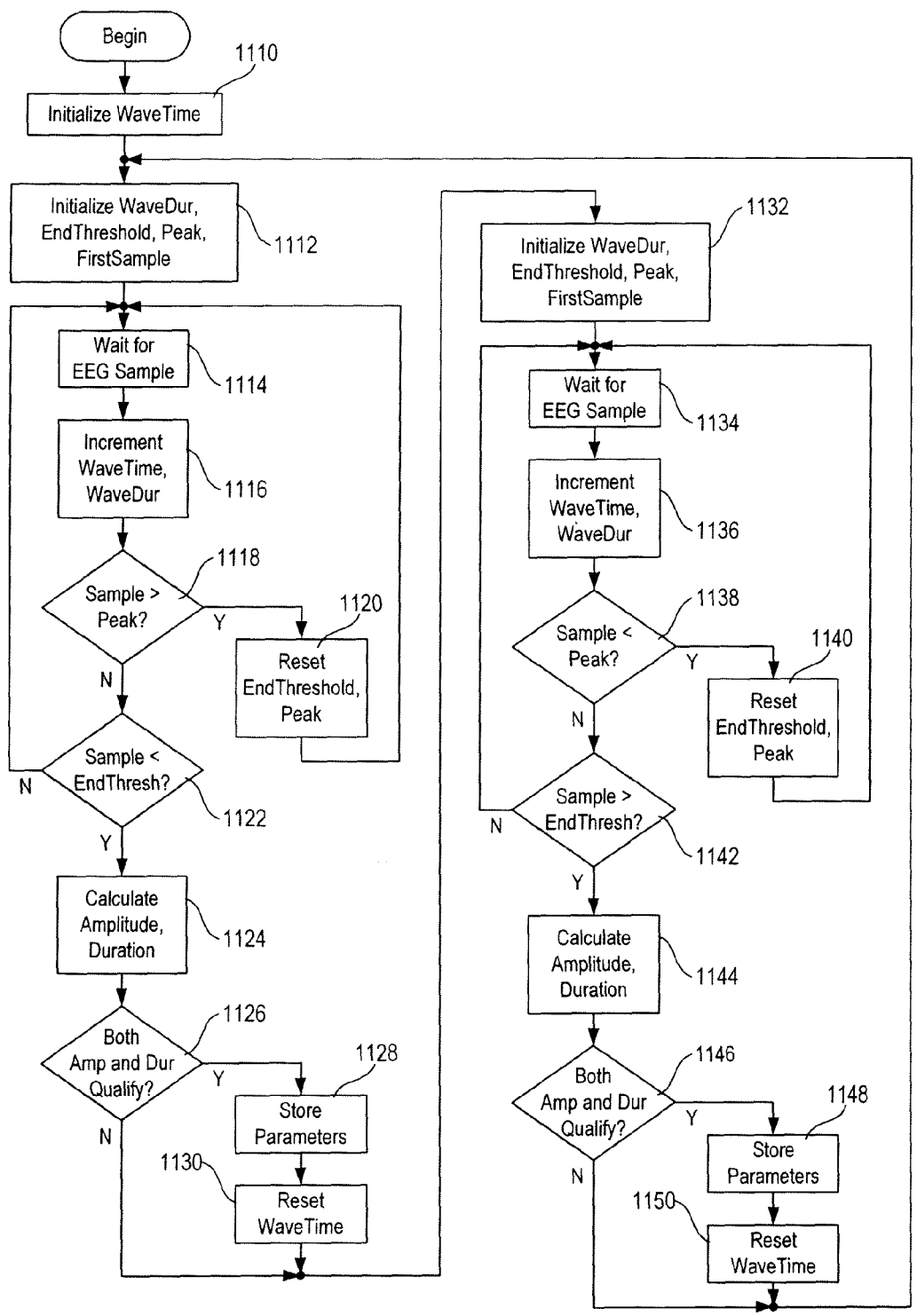
FIG. 31 is a flow chart illustrating the process performed by hardware functional components of the waveform analyzer of FIG. 27 in extracting half waves as illustrated in FIG. 30.

The processing steps performed with regard to the waveform 1310 and half waves of FIG. 30 are set forth in FIG. 31. The method begins by identifying an increasing half wave (with an ending amplitude higher than the starting amplitude, as in the second half wave 1318 of FIG. 30). To do this, a variable corresponding to half wave time is first initialized to zero (step 1410); then half wave duration, ending threshold, peak amplitude, and first sample value are all initialized (step 1412). Specifically, the half wave duration value is set to zero; the peak amplitude and first sample values are set to the amplitude value of the last observed sample, which as described above is a value having 10-bit precision; and the ending threshold is set to the last observed sample minus a small present hysteresis value. After waiting for a measurement of the current EEG sample (step 1414), the half wave time and half wave duration variables are incremented (step 1416). If the current EEG sample has an amplitude greater than the peak amplitude (step 1418), then the amplitude of the half wave is increasing (or continues to increase). Accordingly, the ending threshold is reset to be the current EEG sample's amplitude minus the hysteresis value, and the peak is reset to the current EEG sample's amplitude (step 1420), and the next sample is awaited (step 1414).

If the current EEG sample has an amplitude less than the ending threshold (step 1422), then the hysteresis value has been exceeded, and a local extremum has been identified. Accordingly, the end of the increasing half wave has been reached, and the amplitude and duration of the half wave are calculated (step 1424). The amplitude is equal to the peak amplitude minus the first sample value; the duration is equal to the current half wave duration. Otherwise, the next sample is awaited (step 1414).

If both the amplitude and the duration qualify by exceeding the corresponding present thresholds (step 1426), then the amplitude, duration, half wave time, half wave direction (increasing) are stored in a buffer (step 1428), and the half wave time is reset to zero (step 1430).

At the conclusion of the increasing half wave, the process continues by initializing wave duration, the ending threshold, the peak amplitude, and the first sample value (step 1432). Wave duration is set to zero; the ending threshold is set to the last sample value plus the hysteresis value, the peak amplitude and the first sample value are set to the most recent sample value.

After waiting for a measurement of the current EEG sample (step 1434), the half wave time and half wave duration variables are incremented (step 1436). If the current EEG sample has an amplitude lower than the peak amplitude (step 1438), then the amplitude of the half wave is decreasing (or continuing to decrease). Accordingly, the ending threshold is reset to be the current EEG sample's amplitude plus the hysteresis value, the peak is reset to the current EEG sample's amplitude (step 1440), and the next sample is awaited (step 1434).

If the current EEG sample has an amplitude greater than the ending threshold (step 1442), then the hysteresis value has been exceeded, and a local extremum has been identified. Accordingly, the end of the decreasing half wave has been reached, and the amplitude and duration of the half wave are calculated (step 1444). The amplitude is equal to the first sample value minus the peak amplitude, and the duration is equal to the current half wave duration. Otherwise, the next EEG sample is awaited (step 1434).

If both the amplitude and the duration qualify by exceeding corresponding preset thresholds (step 1446), then the amplitude, duration, half wave time, half wave direction (decreasing) are stored in a buffer (step 1448), and the half wave time is reset to zero (step 1450). It should be noted that, in the context of this specification, the term "exceed" in regard to a threshold value means to meet a specified criterion. Generally, to exceed a threshold herein is to have a numeric value greater than or equal to the threshold, although other interpretations (such as greater than, or less than, or less than or equal to, depending on the context) may be applicable and are deemed to be within the scope of the invention.

At the conclusion of the decreasing half wave, further half waves are then identified by repeating the process from step 1412. As half wave detection is an ongoing and continuous process, this procedure preferably does not exit, but may be suspended from time to time when conditions or device state call for it, e.g., when the device is inactive or when stimulation is being performed. Once suspended in accordance with the invention, the procedure should recommence with the first initialization step 1410.

Accordingly, the process depicted in FIG. 31 stores parameters corresponding to qualified half waves, including their directions, durations, amplitudes, and the elapsed time between adjacent qualified half waves (i.e., the half wave time variable). In the disclosed embodiment of the invention, to reduce power consumption, this procedure is performed in custom electronic hardware; it should be clear that the operations of FIG. 31 are performed in parallel for each active instance of the wave morphology analysis units 1012 (FIG. 27). It should also be noted, however, that certain software can also be used to advantageous effect in this context.

Figure 32:
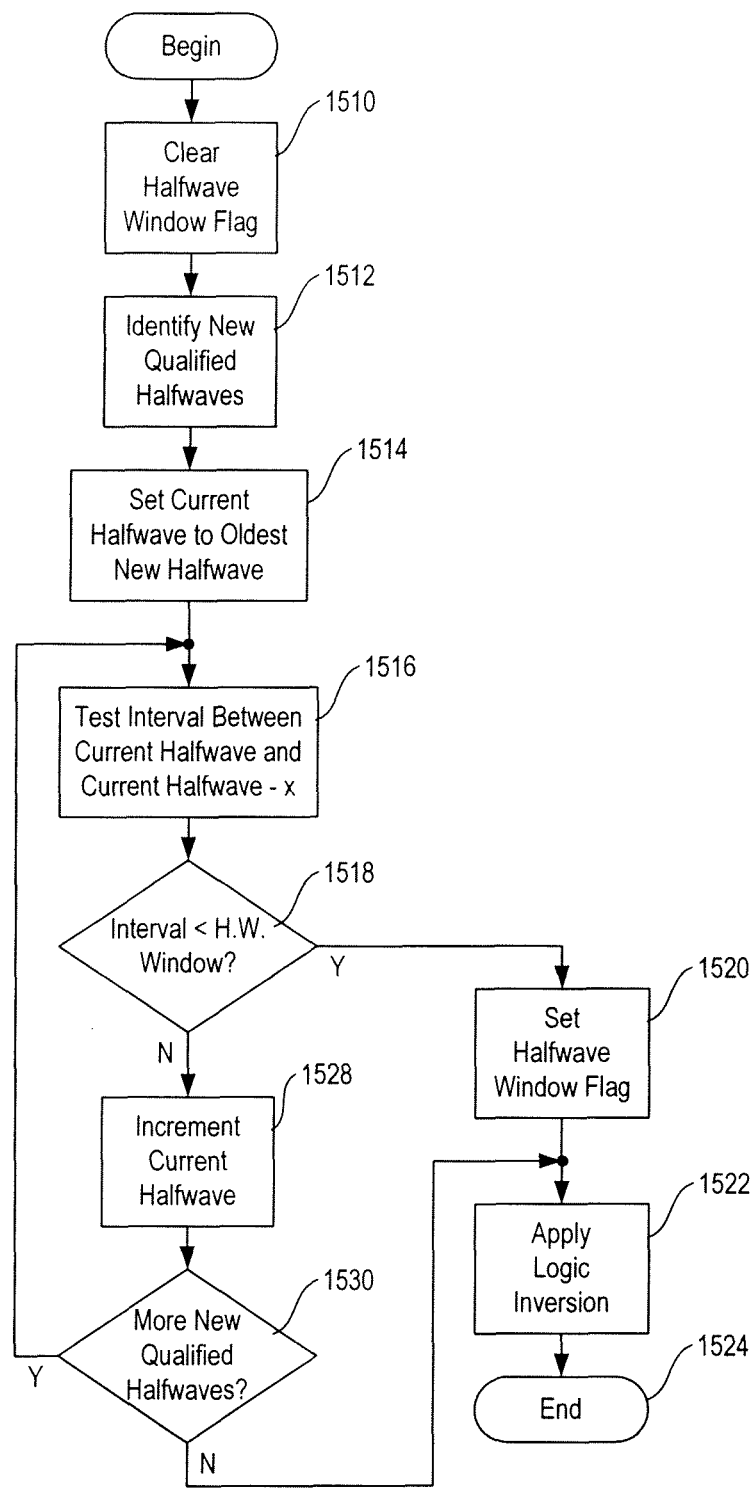
FIG. 32 is a flow chart illustrating the process performed by software in the central processing unit in extracting and analyzing half waves from an EEG signal.

This stored information is used in the software process illustrated in FIG. 32, which is performed on a periodic basis, preferably once every processing window (a recurring time interval that is either fixed or programmable) by a system according to the invention. Consistent with the other analysis tools described herein, the duration of an exemplary processing window is in one embodiment of the invention 128 ms, which corresponds to 32 samples at a 250 Hz sampling rate.

Each time the software process of FIG. 32 is invoked, the half wave window flag is first cleared (step 1510). Any qualified half waves identified by the process set forth in FIG. 31 that are newly identified since the last invocation of the procedure (i.e., all qualified half waves that ended within the preceding processing window) are identified (step 1512). A "current half wave" pointer is set to point to the oldest qualified half wave identified in the most recent processing window (step 1514). The time interval between the current half wave and the prior x half waves is then measured (step 1516), where x is a specified minimum number of half waves (preferably a programmable value) to be identified within a selected half wave time window (the duration of which is another programmable value) to result in the possible detection of a neurological event. If the time interval is less than the duration of the half wave time window (step 1518), then the half wave window flag is set (step 1520), logic inversion is selectively applied (step 1522), and the procedure ends (step 1524). Logic inversion, a mechanism for determining whether an analysis unit is triggered by the presence or absence of a condition, is explained in greater detail below. Otherwise, the current half wave pointer is incremented to point to the next new half wave (step 1528), and if there are no more new half waves (step 1530), logic inversion is applied if desired (step 1522), and the procedure ends (step 1524). Otherwise, the next time interval is tested (step 1516) and the process continues from there.

Logic inversion allows the output flag for the wave morphology analysis unit (or any other analyzer) to be selectively inverted. If logic inversion is configured to be applied to an output of a particular analysis unit, then the corresponding flag will be clear when the detection criteria (e.g., number of qualified half waves) is met, and set when the detection criteria is not met. This capability provides some additional flexibility in configuration, facilitating detection of the absence of certain signal characteristics when, for example, the presence of those characteristics is the norm.

Figure 33:
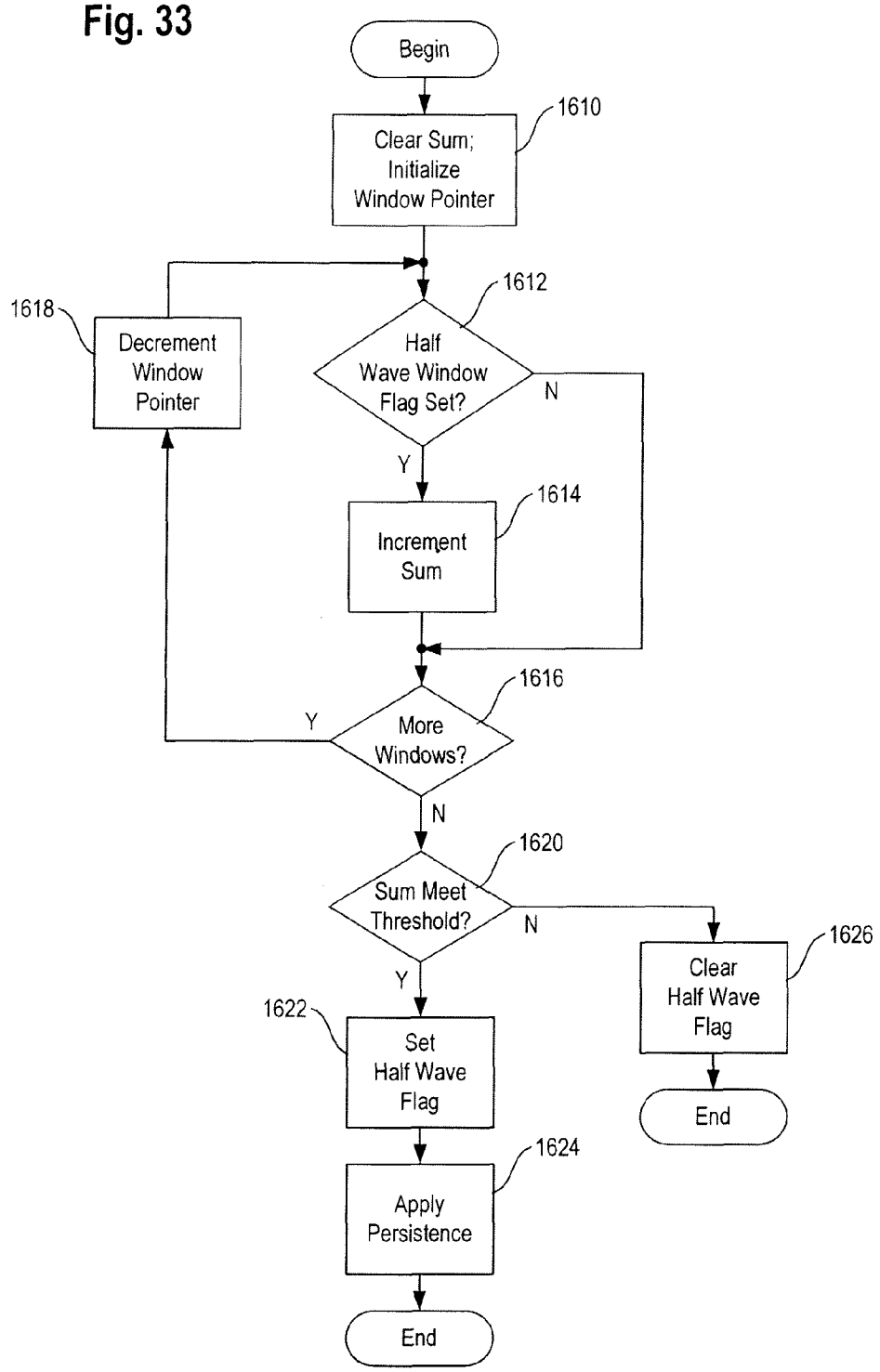
FIG. 33 is a flow chart illustrating the process performed by the software in the central processing unit in the application of an X of Y criterion to half wave windows.

In a preferred embodiment of the invention, the half wave window flag (set in step 1520) indicates whether a sufficient number of qualified half waves occur over an interval ending in the most recent processing window. To reduce the occurrence of spurious detections, an X of Y criterion is applied, causing the wave morphology analysis units to trigger only if a sufficient number of qualified half waves occur in X of the Y most recent processing windows, where X and Y are parameters individually adjustable for each analysis tool. This process is illustrated in FIG. 33.

Initially, a sum (representing recent processing windows having the half wave window flag set) is cleared to zero and a current window pointer is initialized to point to the most recent processing window (step 1610). If the half wave window flag corresponding to the current window pointer is set (step 1612), then the sum is incremented (step 1614). If there are more processing windows to examine (for an X of Y criterion, a total of Y processing windows, including the most recent, should be considered) (step 1616), then the window pointer is decremented (step 1618) and the flag testing and sum incrementing steps (steps 1612-1614) are repeated.

After Y windows have been considered, if the sum of windows having set half wave window flags meets the threshold X (step 1620), then the half wave analysis flag is set (step 1622), persistence (described below) is applied (step 1624), and the procedure is complete. Otherwise, the half wave analysis flag is cleared (step 1626).

Persistence, another per-analysis-tool setting, allows the effect of an event detection (a flag set) to persist beyond the end of the detection window in which the event occurs. In the disclosed system according to the invention, persistence may be set anywhere from one second to fifteen seconds (though other settings are possible), so if detections with multiple analysis tools do not all occur simultaneously (though they should still occur within a fairly short time period), a Boolean combination of flags will still yield positive results. Persistence can also be used with a single analysis tool to smooth the results.

When the process of FIG. 33 is completed, the half wave analysis flag (set or cleared in steps 1622 and 1626, respectively) indicates whether an event has been detected in the corresponding channel of the wave morphology units 1012, or stated another way, whether a sufficient number of qualified half waves have appeared in X of the Y most recent processing windows. Although in the disclosed embodiment, the steps of FIGS. 32 and 33 are performed in software, it should be recognized that some or all of those steps can be performed using custom electronics, if it proves advantageous in the desired application to use such a configuration.

FIG. 34 illustrates the waveform of FIG. 29, further depicting line lengths identified within a time window. The time window used with respect to FIGS. 34-36 may be different from the half wave processing window described above in connection with FIGS. 32-33, but in a preferred embodiment, refers to the same time intervals. From an implementation standpoint, a single device interrupt upon the conclusion of each processing window allows all of the analysis tools to perform the necessary corresponding software processes; the line length analysis process of FIG. 36 (described below) is one such example. A waveform 1710 is a filtered and otherwise pre-processed EEG signal as received in one of the window analysis units 714 from the sensing front end 812. As discussed above, line lengths are considered within time windows. As illustrated in FIG. 34, the duration of an exemplary window 1712 is 32 samples, which is equivalent to 128 ms at a 250 Hz sampling rate.

The total line length for the window 1712 is the sum of the sample-to-sample amplitude differences within that window 1712. For example, the first contribution to the line length within the window 1712 is a first amplitude difference 1714 between a previous sample 1716 occurring immediately before the window 1712 and a first sample 1718 occurring within the window 1712. The next contribution comes from a second amplitude difference 1720 between a first sample 1418 and a second sample 1722; a further contribution 1724 comes from a third amplitude difference between the second sample 1722 and a third sample 1726; and so on. At the end of the window 1712, the final contribution to the line length comes from a last amplitude difference 1730 between a second-last sample 1732 in the window 1712 and a last sample 1734 in the window 1712. Note that all line lengths, whether increasing or decreasing in direction, are accumulated as positive values by the invention; accordingly, a decreasing amplitude difference 1714 and an increasing amplitude difference 1728 both contribute to a greater line length.

As illustrated herein, and as discussed in detail above, there are thirty-two samples within the window 1712. The illustrated window 1712 has a duration of 128 ms, and accordingly, the illustrated sample rate is 250 Hz. It should be noted, however, that alternate window durations and sample rates are possible and considered to be within the scope of the present invention.

Figure 35:
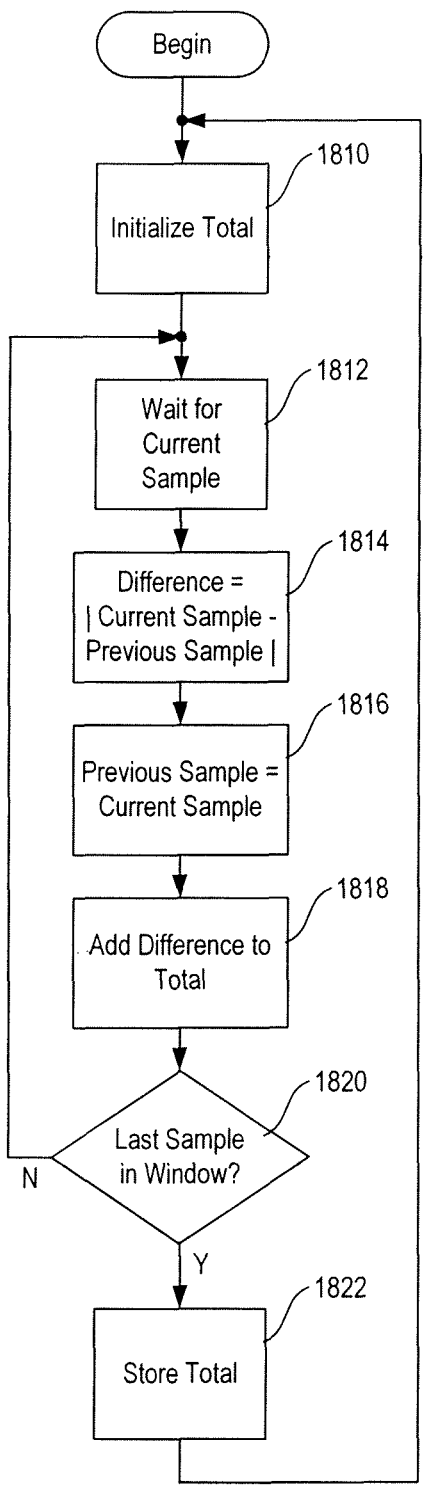
FIG. 35 is a flow chart illustrating the process performed by hardware functional components of the waveform in analyzer of FIG. 27 in calculating the line length function as illustrated in FIG. 34.

The line lengths illustrated in FIG. 34 are calculated as shown by the flow chart of FIG. 35, which is invoked at the beginning of a new time window. Initially, a line length total variable is initialized to zero (step 1810). The current sample is awaited (step 1812), and the absolute value of the amplitude difference between the current sample and the previous sample (which, when considering the first sample in a window, may come from the last sample in a previous window) is measured (step 1814).

In various alternative embodiments of the invention, either the measured difference (as calculated in step 1814, described above), or the sample values used to calculate the difference may be mathematically transformed in useful nonlinear ways. For example, it may be advantageous in certain circumstances to calculate the difference between adjacent samples using the squares of the sample values, or to calculate the square of the difference between sample values, or both. It is contemplated that other transformations (such as square root, exponentiation, logarithm, and other nonlinear functions) might also be advantageous in certain circumstances. Whether or not to perform such a transformation and the nature of any transformation to be performed are preferably programmable parameters of the device 600.

For use in the next iteration, the previous sample is replaced with the value of the current sample (step 1516), and the calculated absolute value is added to the total (step 1818). If there are more samples remaining in the window 1712 (step 1820), another current sample is awaited (step 1812) and the process continues. Otherwise, the line length calculation for the window 1712 is complete, and the total is stored (step 1822, the total is re-initialized to zero (step 1810), and the process continues.

As with the half wave analysis method set forth above, the line length calculation does not need to terminate; it can be free-running yet interruptible. If the line length calculation is restarted after having been suspended, it should be re-initialized and restarted at the beginning of a window. This synchronization can be accomplished through hardware interrupts.

Figure 36:
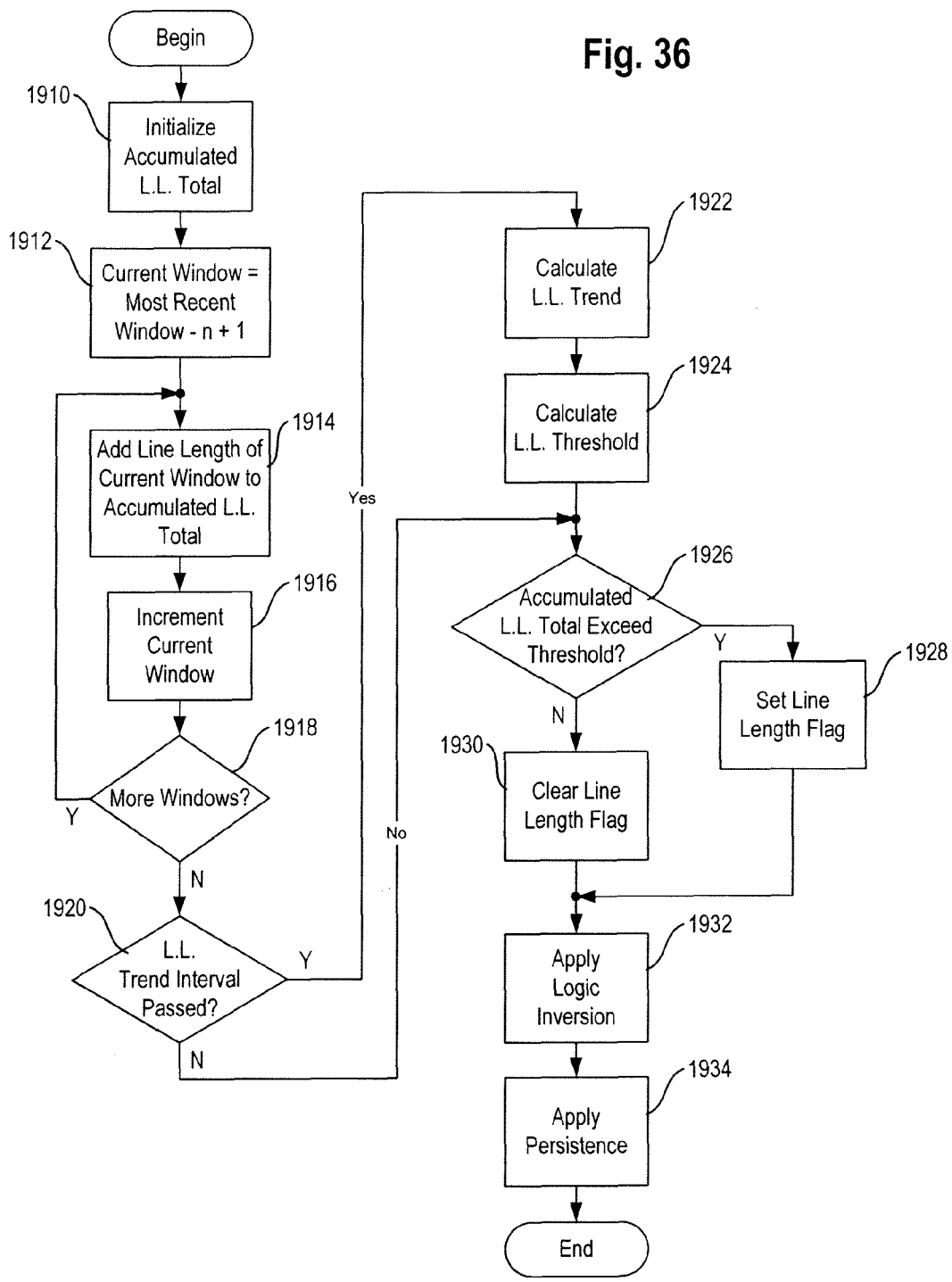
FIG. 36 is a flow chart illustrating the process performed by software in the central processing unit in calculating and analyzing the line length function of an EEG signal.

The line lengths calculated as shown in FIG. 35 are then processed as indicated in the flow chart of FIG. 36, which is performed after each window 1712 is calculated and stored (step 1822).

The process begins by calculating a running accumulated line length total over a period of n time windows. Where n>1, the effect is that of a sliding window; in an alternative embodiment, an actual sliding window processing methodology may be used. First, the accumulated total is initialized to zero (step 1910). A current window pointer is set to indicate the $n^{th}$-last window, i.e., the window (n−1) windows before the most recent window (step 1912). The line length of the current window is added to the total (step 1914), the current window pointer is incremented (step 1916), and if there are more windows between the current window pointer and the most recent (last) window (step 1918), the adding and incrementing steps (1914-1916) are repeated. Accordingly, by this process, the resulting total includes the line lengths for each of the n most recent windows.

In the disclosed embodiment of the invention, the accumulated total line length is compared to a dynamic threshold, which is based on a trend of recently observed line lengths. The trend is recalculated regularly and periodically, after each recurring line length trend interval (which is preferably a fixed or programmed time interval). Each time the line length trend interval passes (step 1920), the line length trend is calculated or updated (step 1922). In a presently preferred embodiment of the invention, this is accomplished by calculating a normalized moving average of several trend samples, each of which represents several consecutive windows of line lengths. A new trend sample is taken and the moving average is recalculated upon every line length trend interval. The number of trend samples used in the normalized moving average and the number of consecutive windows of the line length measurements per trend sample are preferably both fixed or programmable values.

After the line length trend has been calculated, the line length threshold is calculated (step 1924) based on the new line length trend. In the disclosed embodiment of the invention, the threshold may be set as either a percentage of the line length trend (either below 100% for a threshold that is lower than the trend, or above 100% for a threshold that is higher than the trend) or alternatively a fixed numeric offset from the line length trend (either negative for a threshold that is lower than the trend, or positive for a threshold that is higher than the trend). It should be observed that other methods for deriving a numeric threshold from a numeric trend are possible and deemed to be within the scope of the invention.

The first time the process of FIG. 36 is performed, there is generally no line length trend against which to set a threshold. Accordingly, for the first several passes through the process (until a sufficient amount of EEG data has been processed to establish a trend), the threshold is essentially undefined and the line length detector should not return a positive detection. Some "settling time" is required to establish trends and thresholds before a detection can be made.

If the accumulated line length total exceeds the calculated threshold (step 1926), then a flag is set (step 1928) indicating a line-length-based event detection on the current window analysis unit channel 1014. As described above, in the disclosed embodiment of the invention, the threshold is dynamically calculated from a line length trend, but alternatively, the threshold may be static, either fixed or programmed into the device 600. If the accumulated line length total does not exceed the threshold, the flag is cleared (step 1930). Once the line length flag has been either set or cleared, logic inversion is applied (step 1932), persistence is applied (step 1934), and the procedure terminates.

The resulting persistent line length flag indicates whether the threshold has been exceeded within one or more windows over a time period corresponding to the line length flag persistence. As will be discussed in further detail below, line length event detections can be combined with the half wave event detections, as well as any other applicable detection criteria according to the invention.

FIG. 37 illustrates the waveform of FIG. 29 with area under the curve identified within a window. Area under the curve, which in some circumstances is somewhat representative of a signal's energy (though energy of a waveform is more accurately represented by the area under the square of a waveform), is another detection criterion in accordance with the invention.

The total area under the curve represented by a waveform 2010 within the window 2012 is equal to the sum of the absolute values of the areas of each rectangular region of unit width vertically bounded by the horizontal axis and the sample. For example, the first contribution to the area under the curve within the window 2012 comes from a first region 2014 between a first sample 2016 and a baseline 2017. A second contribution to the area under the curve within the window 2012 comes from a second region 2018, including areas between a second sample 2020 and the baseline 2017. There are similar regions and contributions for a third sample 2022 and the baseline 2017, a fourth sample 2024 and the baseline 2017, and so on. It should be observed that the region widths are not important—the area under each sample can be considered the product of the sample's amplitude and a unit width, which can be disregarded. In a similar manner, each region is accumulated and added to the total area under the curve within the window 2012. Although the concept of separate rectangular regions is a useful construct for visualizing the idea of area under a curve, it should be noted that a process for calculating area need not partition areas into regions as shown in FIG. 37—it is only necessary to accumulate the absolute value of the waveform's amplitude at each sample, as the unit width of each region can be disregarded. The process for doing this will be set forth in detail below in connection with FIG. 38.

Figure 38:
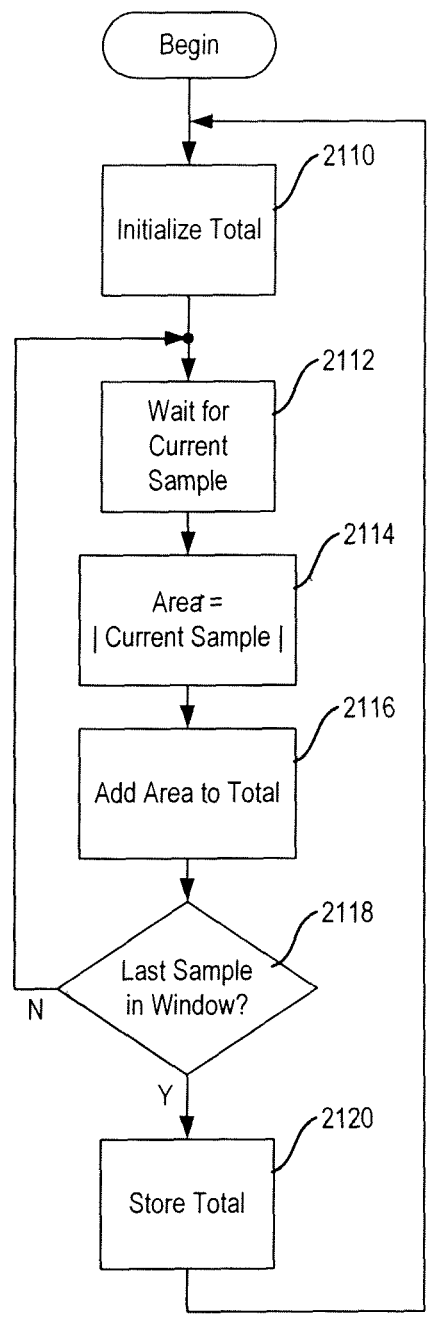
FIG. 38 is a flow chart illustrating the process performed by hardware functional components of the waveform analyzer of FIG. 37 in calculating the area function as illustrated in FIG. 37.

The areas under the curve illustrated in FIG. 37 are calculated as shown by the flow chart of FIG. 38, which is invoked at the beginning of a time window. Initially, an area total variable is initialized to zero (step 2110). The current sample is awaited (step 2112), and the absolute value of the current sample is measured (step 2114).

As with the line length calculation method described above (with reference to FIG. 35), in various alternative embodiments of the invention, the current sample (as measured in step 2114, described above) may be mathematically transformed in useful nonlinear ways. For example, it may be advantageous in certain circumstances to calculate the square of the current sample rather than its absolute value. The result of such a transformation by squaring each sample will generally be more representative of signal energy, though it is contemplated that other transformations (such as square root, exponentiation, logarithm, and other nonlinear functions) might also be advantageous in certain circumstances. Whether or not to perform such a transformation and the nature of any transformation to be performed are preferably programmable parameters of the device 600.

The calculated absolute value is added to the total (step 2116). If there are more samples remaining in the window 2012 (step 2118), another current sample is awaited (step 2112) and the process continues. Otherwise, the area calculation for the window 2012 is complete, and the total is stored (step 2120), the total is re-initialized to zero (step 2110), and the process continues.

As with the half wave and line length analysis methods set forth above, the area calculation does not need to terminate; it can be free-running yet interruptible. If the area calculation is restarted after having been suspended, it should be re-initialized and restarted at the beginning of a window. This synchronization can be accomplished through hardware interrupts.

Figure 39:
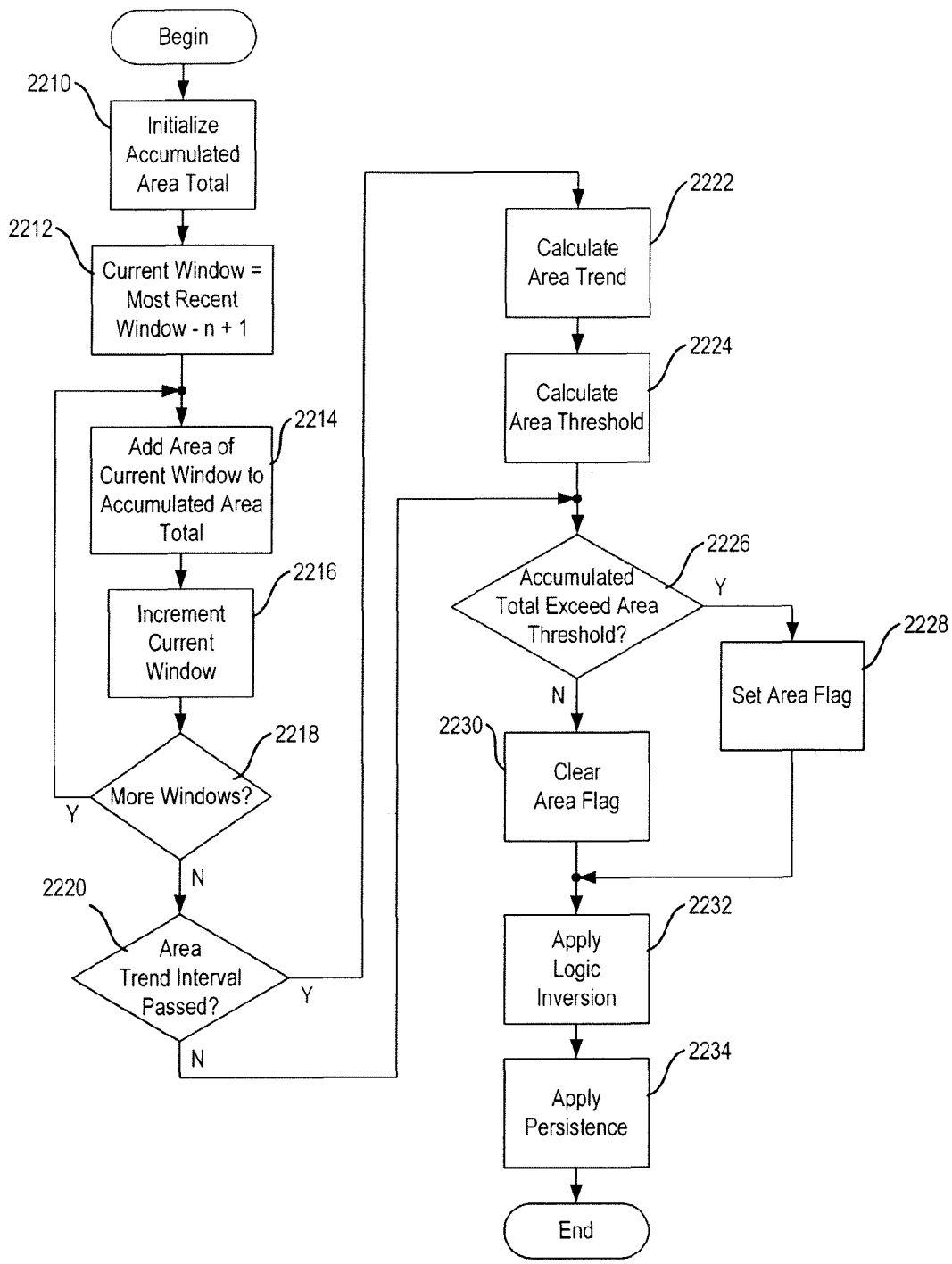
FIG. 39 is a flow chart illustrating the process performed by software in the central processing unit in calculating and analyzing the area function of an EEG signal.

The line lengths calculated as shown in FIG. 38 are then processed as indicated in the flow chart of FIG. 39, which is performed after each window 2012 is calculated and stored (step 2120).

The process begins by calculating a running accumulated area total over a period of n time windows. Where n>1, the effect is that of a sliding window; in an alternative embodiment an actual sliding window processing methodology may be used. First, the accumulated total is initialized to zero (step 2210). A current window pointer is set to indicate the $n^{th}$-last window, i.e., the window (n−1) windows before the most recent window (step 2212). The area for the current window is added to the total (step 2214), the current window pointer is incremented (step 2216), and if there are more windows between the current window and the most recent (last) window (step 2218), the adding and incrementing steps (2214-2216) are repeated. Accordingly, by this process, the resulting total includes the areas under the curve for each of the n most recent windows.

In the disclosed embodiment of the invention, the accumulated total area is compared to a dynamic threshold, which is based on a trend of recently observed areas. The trend is recalculated regularly and periodically, after each recurring area trend interval (which is preferably a fixed or programmed time interval). Each time the area trend interval passes (step 2220), the area trend is calculated or updated (step 2222). In a presently preferred embodiment of the invention, this is accomplished by calculating a normalized moving average of several trend samples, each of which represents several consecutive windows of areas. A new trend sample is taken and the moving average is recalculated upon every area trend interval. The number of trend samples used in the normalized moving average and the number of consecutive windows of area measurements per trend sample are preferably both fixed or programmable values.

After the area trend has been calculated, the area threshold is calculated (step 2224) based on the new area trend. As with line length, discussed above, the threshold may be set as either a percentage of the area trend (either below 100% for a threshold that is lower than the trend, or above 100% for a threshold that is higher than the trend) or alternatively a fixed numeric offset from the area trend (either negative for a threshold that is lower than the trend, or positive for a threshold that is higher than the trend).

The first time the process of FIG. 39 is performed, there is generally no area trend against which to set a threshold. Accordingly, for the first several passes through the process (until a sufficient amount of EEG data has been processed to establish a trend), the threshold is essentially undefined and the area detector should not return a positive detection. Some "settling time" is required to establish trends and thresholds before a detection can be made.

If the accumulated total exceeds the calculated threshold (step 2226), then a flag is set (step 2228) indicating an area-based event detection on the current window analysis unit channel 1014. Otherwise, the flag is cleared (step 2230). Once the area flag has been either set or cleared, logic inversion is applied (step 2232), persistence is applied (step 2234), and the procedure terminates.

The resulting persistent area flag indicates whether the threshold has been exceeded within one or more windows over a time period corresponding to the area flag persistence. As will be discussed in further detail below, area event detections can be combined with the half wave event detections, line length event detections, as well as any other applicable detection criteria according to the present embodiments.

In a preferred embodiment, each threshold for each channel and each analysis tool can be programmed separately; accordingly, a large number of individual thresholds may be used in a system according to the invention. It should be noted thresholds can vary widely; they can be updated by a physician via the external programmer 612 (FIG. 23), and some analysis tool thresholds (e.g., line length and area) can also be automatically varied depending upon observed trends in the data. This is preferably accomplished based on a moving average of a specified number of window observations of line length or area, adjusted as desired via a fixed offset or percentage offset, and may compensate to some extent for diurnal and other normal variations in brain electrophysiological parameters.

With regard to the flow charts of FIGS. 31-33, 35-36, and 38-39, it should be noted that there can be a variety of ways these processes are implemented. For example, state machines, software, hardware (including ASICs, FPGAs, and other customer electronics), and various combinations of software and hardware, are all solutions that would be possible to practitioners of ordinary skill in the art of electronics and systems design. It should further be noted that the steps performed in software need not be, as some of them can be implemented in hardware, if desired, to further reduce computational load on the processor. In the context of the invention, it is not believed to be advantageous to have the software perform additional steps, as that would likely increase power consumption.

In one embodiment, one of the detection schemes set forth above (e.g., half wave detection) is adapted to use an X of Y criterion to weed out spurious detections. This can be implemented via a shift register, as usual, or by more efficient computational methods. As described above, half waves are analyzed on a window-by-window basis, and as described above (in connection with FIG. 33), the window results are updated on a separate analysis window interval. If the detection criterion (i.e., a certain number of half waves in less than a specified time period) is met for any of the half waves occurring in the most recent window, then detection is satisfied within that window. If that occurs for at least X of the Y most recent windows, then the half wave analysis tool triggers a detection. If desired, other detection algorithms (such as line length and area) may operate in much the same way: if thresholds are exceeded in at least X of the Y most recent windows, then the corresponding analysis tool triggers a detection.

Also, in the disclosed embodiment, each detection flag, after being set, remains set for a selected amount of time, allowing them to be combined by Boolean logic (as described below) without necessarily being simultaneous.

Figure 40:
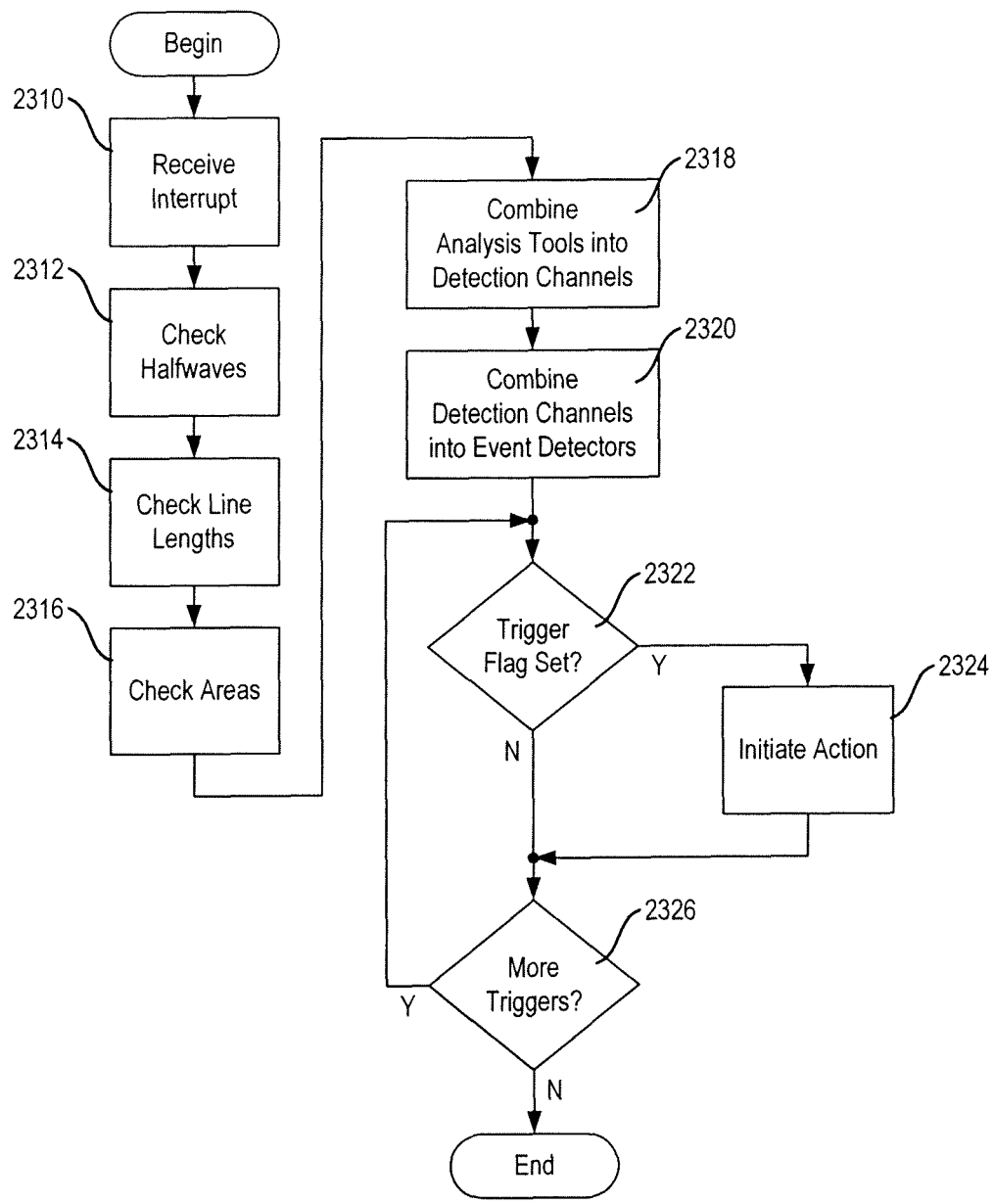
FIG. 40 is a flow chart illustrating the process performed by event-driven software in the central processing unit to analyze half wave, line length, and area information for detection.

As indicated above, each of the software processes set forth above (FIGS. 32-33, 36, and 39) correspond to functions performed by the wave morphology analysis units 1012 and window analysis units 1014. Each one is initiated periodically, typically once per detection window (1512, 1812). The outputs from the half wave and window analysis units 1012 and 1014, namely the flags generated in response to counted qualified half waves, accumulated line lengths, and accumulated areas are combined to identify event detections as functionally illustrated in FIG. 28 and as described via flow chart in FIG. 40.

The process begins with the receipt of a timer interrupt (step 2310), which is typically generated on a regular periodic basis to indicate the edges of successive time windows. Accordingly, in a system or method according to the disclosed embodiment of the invention, such a timer interrupt is received every 128 ms, or as otherwise programmed or designed. Then the half wave (step 2312, FIGS. 32-33), line length (step 2314, FIG. 36), and area (step 2316, FIG. 39) analysis tools are evaluated with respect to the latest data generated thereby, via the half wave analysis flag, the line length flag, and the area flag for each active channel. The steps of checking the analysis tools (steps 2312, 2314, and 2316) can be performed in any desired order or in parallel, as they are generally not interdependent. It should be noted that the foregoing analysis tools should be checked for every active channel, and may be skipped for inactive detection channels.

Flags, indicating whether particular signal characteristics have been identified in each active channel, for each active analysis tool, are then combined into detection channels (step 2318) as illustrated in FIG. 28. In the disclosed embodiment of the invention, this operation is performed as described in detail below with reference to FIG. 41. Each detection channel is a Boolean AND combination of analysis tool flags for a single channel, and as disclosed above, there are preferably at least eight channels in a system according to the invention.

The flags for multiple detection channels are then combined into event detector flags (step 2320), which are indicative of identified neurological events calling for action by the device. This process is described below, see FIG. 40, and is in general a Boolean combination of detection channels, if there is more than one channel per event detector.

If an event detector flag is set (step 2322), then a corresponding action is initiated (step 2324) by the device. Actions according to the invention can include the presentation of a warning to the patient, an application of therapeutic electrical stimulation, a delivery of a dose of a drug, an initiation of a device mode change, or a recording of certain EEG signals; it will be appreciated that there are numerous other possibilities. It is preferred, but not necessary, for actions initiated by a device according to the invention to be performed in parallel with the sensing and detection operations described in detail herein. It should be recognized that the application of electrical stimulation to the brain may require suspension of certain of the sensing and detection operations, as electrical stimulation signals may otherwise feed back into the detection system 822 (FIG. 24), causing undesirable results and signal artifacts.

Multiple event detector flags are possible, each one representing a different combination of detection channel flags. If there are further event detector flags to consider (step 2326), those event detector flags are also evaluated (step 2322) and may cause further actions by the device (step 2324). It should be noted that, in general, actions performed by the device (as in step 23240 may be in part dependent on a device state—even if certain combinations of events do occur, no action may be taken if the device is in an inactive state, for example.

Figure 41:
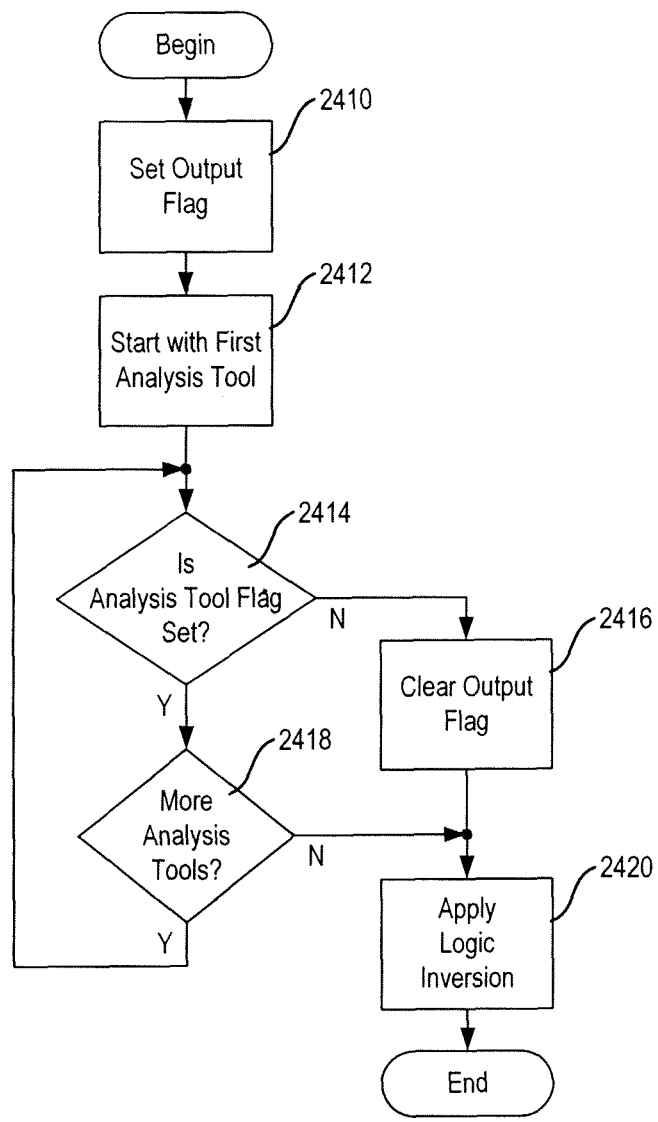
FIG. 41 is a flow chart illustrating the combination of analysis tools into detection channels in one embodiment.

As described above, and as illustrated in FIG. 40 as step 2318, a corresponding set of analysis tool flags is combined into a detection channel flag as shown in FIG. 41 (see also FIG. 38). Initially, the output detection channel flag is set (step 2410). Beginning with the first analysis tool for a particular detection channel (step 2412), if the corresponding analysis tool flag is not set (step 2414), then the output detection channel flag is cleared (step 2416).

If the corresponding analysis tool flag is set (step 2414), the output detection channel flag remains set, and further analysis tools for the same channel, if any (step 2418), are evaluated. Accordingly, this combination procedure operates as a Boolean AND operation—if any of the enabled and active analysis tools for a particular detection channel does not have a set output flag, then no detection channel flag is output by the procedure.

A clear analysis tool flag indicates that no detection has been made within the flag persistence period, and for those analysis tools that employ an X of Y criterion, that such criterion has not been met. In certain circumstances, it may be advantageous to also provide detection channel flags with logic inversion. Where a desired criterion (i.e., combination of analysis tools) is not met, the output flag is set (rather than cleared, which is the default action). This can be accomplished by providing selectable Boolean logic inversion (step 2420) corresponding to each event detector.

Figure 42:
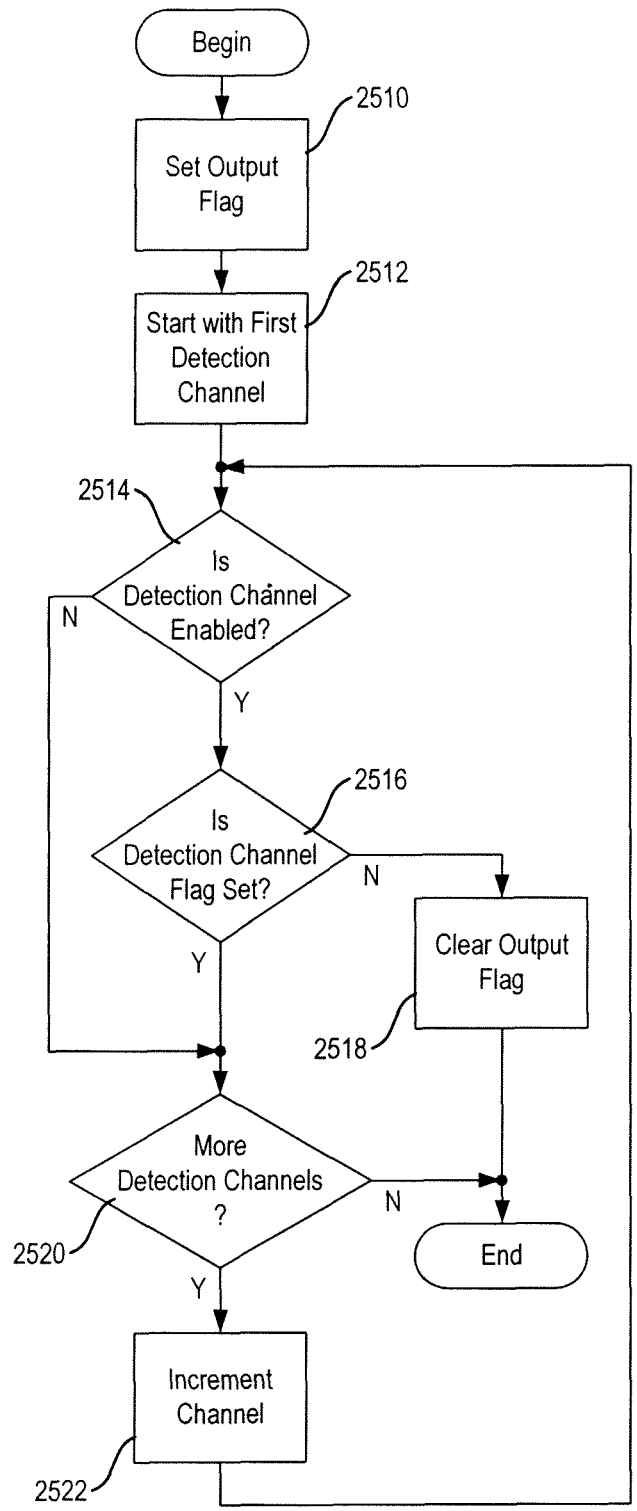
FIG. 42 is a flow chart illustrating the combination of detection channels into event detectors in one embodiment.

Also as described above, and as illustrated in FIG. 40 as step 2320, multiple detection channel flags are combined into a single event detector flag as shown in FIG. 42 (see also FIG. 38). Initially, the output event detector flag is set (step 2510). Beginning with the first detection channel for a particular event detector (step 2512), if the channel is not enabled (step 2514), then no check is made. If the channel is enabled and the corresponding detection channel flag is not set (step 2516), then the output event detector flag is cleared (step 2518) and the combination procedure exits. If the corresponding detection channel flag is set (step 2516), the output event detector flag remains set, and further detection channels, if any (step 2520), are evaluated after incrementing the channel being considered (step 2522). Accordingly, this combination procedure also operates as a Boolean AND operation—if any of the enabled and active detection channels does not have a set output flag, then no event detector flag is output by the procedure. It should also be observed that a Boolean OR combination of detection channels may provide useful information in certain circumstances; a software or hardware flow chart accomplishing such a combination is not illustrated, but could easily be created by an individual of ordinary skill in digital electronic design or computer programming.

An implantable version of a system according to the present embodiments advantageously ahs a long-term average current consumption on the order of 10 microamps, allowing the implanted device to operate on power provided by a coin cell or similarly small battery for a period of years without need for replacement. It should be noted, however, that as battery and power supply configuration vary, the long-term average current consumption of a device according to the invention may also vary and still provide satisfactory performance.

It should be observed that while the foregoing detailed description of various embodiments is set forth in some detail, the invention is not limited to those details and an implantable neurostimulator or neurological disorder detection device made according to the invention can differ from the disclosed embodiments in numerous ways. In particular, it will be appreciated that embodiments of the present invention may be employed in many different applications to detect anomalous neurological characteristics in at least one portion of a patient's brain. It will be appreciated that the functions disclosed herein as being performed by hardware and software, respectively, may be performed differently in an alternative embodiment. It should further be noted that functional distinctions are made above for purposes of explanation and clarity; structural distinctions in a system or method according to the invention may not be drawn along the same boundaries.

Figure 43:
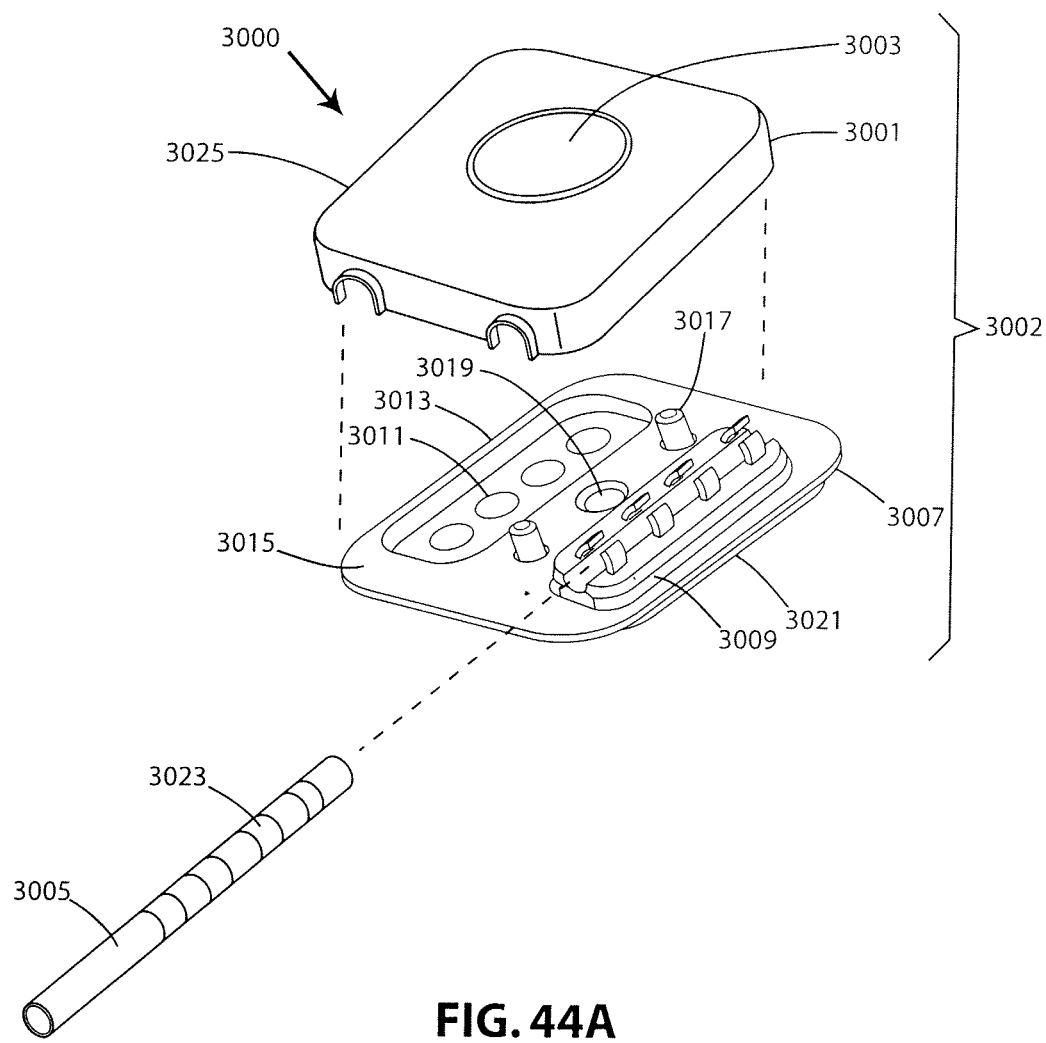
FIG. 43 is a perspective view of an electrode lead connector according to one embodiment shown disassembled into a clamp housing and a connector carriage with a split interposer seated therein and having an electrode lead according to one of the embodiments disclosed in the above FIGS.

FIG. 43 illustrates an implantable lead connector assembly 3000 that is connectable to an electrode lead 3005, which may be in the form of any of the leads described hereinbefore (e.g., reinforced depth lead 100 of FIG. 1 or the reinforced cortical lead 500 of FIG. 9). A connector housing 3002 of the lead connector assembly 3000 desirably includes three conceptual parts: a clamp housing 3001, a connector carriage 3007, and an interposer or removable seal 3009. Various of these functional sections may be combined or integrated as shown below, but the preferred exemplary device should have the following: a.) a functional clamp that holds the implantable lead connector assembly 3000 closed and preferably simultaneously holds the various electrode leads in place while isolating the various electrical contacts, b.) an interposer or seal that accepts the proximal end of the various electrode leads and cooperatively (upon clamping or closing the inventive connector assembly) seals the various electrical contacts and "makes" the circuit with the lead contacts in a such a way that the information or stimulus passing through the connector is isolated into the circuitry as intended by the designer, and c.) a connector carriage supporting the interposer, often serving as a portion of the clamping function, and desirably serving as a passageway for electrical signals into and out of the attached stimulator or signal processor.

Specifically, shown in FIG. 43, between the clamp housing 3001 and the connector carriage 3007, the electrode lead 3005 is variously received by, held in place by, and positioned by an interposer or removable seal 3009 that accommodates and electrically isolates electrical conductive members 3021 in the connector carriage 3007. In this specification, the terms "interposer," "removable seal," and "interposer seal" may be used to describe the component designated "3009" in FIG. 43 because of the multiple functions performed by that component.

In any case, each of the electrical conductive members 3021 make electrical contact with a corresponding lead terminus or proximal contact 3023 on electrode lead 3005. It is often the case in such service, that some amount of fluid (typically conductive) may be present within the confines of inventive connector assembly 3002 after the device is closed and in service. The interposer 3009 is to seal one electrical conductive member 3021 from all non-common electrically conductive or active members thus tending to eliminate the passage of erroneous information to the attached signal processor and to certify the passage of stimulation to appropriate sectors of the brain.

In this variation of the invention, the electrical conductive members 3021 pass through the connector carriage 3007 and eventually project from the lead connector assembly 3000 as feedthrough pins 3013 (FIG. 46) where they may be linked to an implantable device such as a signal processor or stimulator mentioned elsewhere.

During assembly, the connector housing 3002 (clamp housing 3001 and connector carriage 3007) may be joined by the fastener 3003 actuating the inventive connector assembly. In this variation of the invention, engaging the fastener 3003 seals the electrode lead 3005 in the interposer seal 3009 and presses the electrical conductive members 3021 against the proximal contacts or termini 3023 on the electrode lead 3005. This forms an electrical circuit between the electrical conductive members 3021 and the electrode lead.

As shown in the Figures, the lead connector assembly 3000 may receive multiple, e.g., one or two, electrode leads for connection to an implantable device. However, the invention is not so limited. The connector housing 3002 may be extended or adapted to accommodate three or more electrical leads. Furthermore, although the external profile of the connector housing 3002 is shown to be rectangular, the outer profiles of the clamp housing 3001 and the cooperating carriage 3007 may be of any convenient shape. To aid in attachment, the lead connector assembly's 3000 shape may be adapted to fit a mounting device or a neural stimulator or signal processing device.

The lead connector assembly 3000 desirably is small enough to be implanted within a patient's cranium, in a patient's cranial bone wall, or under the patient's scalp. The overall dimensions of the lead connector assembly 3000 will typically depend upon a variety of factors, e.g., the number of leads that the connector assembly is to accommodate, the size of the electrode leads, the size of the cranium, etc. For instance and illustrative of the tidy size of the inventive device, the lead connector assembly 3000 shown in FIG. 43 has a depth of approximately 6.5 mm, and a length of approximately 15.0 mm and a breadth of approximately 13.0 mm. As indicated, these dimensions are not limiting; the ultimate size and shape can vary greatly without affecting the performance of the device.

Returning to FIG. 43, the connector housing 3002 is shown to be made up of at least a clamp housing 3001 and a connector carriage 3007. In the variation found in FIG. 43, these two components are depicted to be separable and such separability facilitates installation and replacement of electrode lead 3005; however, the clamp housing 3001 and a connector carriage 3007 may be integrated into a single element or perhaps joined by a hinge. The clamp housing can be made of a biocompatible material such as polyetheretherketone (PEEK). The interior of the clamp housing 3001 holds the interposer 3009 in place and therefore desirably conforms in shape to that of the interposer 3009. This concept is discussed in greater detail below, particularly with respect to FIG. 46. Because of the many variations in the shape of the interposer 3009 (see below), a variety of clamp housing designs is contemplated and clearly the interior shape of the clamp housing 3001 is not limited to one having a recessed region that fits the shape of the interposer 3009.

The interior of the clamp housing 3001 may include one or more sealing gaskets to isolate the interior of the clamp housing 3001 from external fluids after closure of the connector housing 3002 by fastener 3003. Preferably, however, the interposer 3009 provides any required sealing. As noted above, the interposer 3009 isolates each of the electrical physical contacts occurring between the electrode lead 3005 and the electrical conductive members 3021 variously from each other and from the connector carriage 3007.

Desirably, the various gaskets and the interposer 3009 are made of a biocompatible polymer, and perhaps an inert elastomer such as suitable silicone (for example, MED4950, a medical grade silicone offered by NuSil Technology of Carpinteria, Calif.). One of ordinary skill in this design art will appreciate the existence of and selection of other materials suitable for this function and for the other materials noted by example herein. A coating such as PARYLENE (polyparaxyxylene) may be applied to prevent fusion adhesion between the seal and other surfaces.

Clamp housing 3001 attaches to connector carriage 3007. In the same way as was the case with the clamp housing 3001, the interior of the connector carriage 3007 desirably supports and conforms to the interposer 3009. In FIG. 43, this relationship is seen by the recessed region 3017 into which the interposer 3009 fits. The framework of the connector carriage 3007 may be of a suitable biocompatible material, e.g., titanium. The region of the connector carriage 3007 directly adjacent to seating for the interposer 3009 is the baseplate 3011. Pin members 3013 pass through this baseplate 3011 and project from the exterior of the connector carriage 3007 (see FIG. 47) where they are connectable (directly or indirectly) to an implantable device such as a signal processor, stimulator, or other device. This variation of the invention includes non-integral pins 3013 passing though baseplate 3011. The depicted pins 3013 are fixed to the baseplate 3011 but, unlike the variation discussed above, are separable from the electrical conductive members 3021. Other variations include, of course, the use of electrical conductive connectors 3021 that are integrated with pins 3013.

Depending on the specific design, the baseplate 3011 supports or contains the electrical conductive members 3021 and generally provides a sealing surface for interposer seal 3009. A filtering capacitor 3305 (FIG. 46) may be physically and electrically connected to baseplate 3011 and to the electrical conductive members 3021. The electrical conductive members 3021 may also be secured to the baseplate 3011 in a number of ways: for instance, by forming the baseplate 3011 as a co-fired ceramic with appropriate choice of conductive regions, the electrical conductive members 3021 may be made to be integral with the baseplate 3011. Alternately, as noted above, the electrical conductive members 3021 may be of an assemblage containing pins 3013 that are attached to baseplate 3011 by, e.g., use of a biocompatible brazing material.

As shown in FIG. 43, the connection to the electrode lead 3005 may include two parts: a feedthrough pin 3013 and a compressible electrical connection member 3021. The compressible electrical connection members 3021 may be, for instance, spring contacts or fuzz button connectors and other similarly functional components. Preferably, the compressible electrical connection members 3021 is a spring contact. A spring contact is an open or closed loop of a biocompatible, conductive material, such as a pure metal or an alloy (such as 80-20 Platinum-Iridium) that achieves a predictable amount of opposing force when compressed.

Alternatively, the compressible electrical connection members 3021 may be fuzz buttons. Fuzz buttons may be made from a very fine diameter wire, e.g., of Pt—Ir, that is formed, much like a steel wool pad, into a shape approximating a cylinder. These forms are commercially available from Tecknit Co of Cranford, N.J. Other shapes (for example, multiple coils) and other conductive materials may also serve as compressible electrical connection members.

The feedthrough pin 3013 is the portion of the electrical conductive member that extends through the baseplate 3011, projects externally, and may then be attached, directly or indirectly, to the implantable device. Typically, the feedthrough pin 3013 contains or is made of a suitable biocompatible, corrosion-resistant, highly conductive metal or alloy, e.g., a member of the Noble Metal group, e.g., platinum, palladium, iridium, and preferably alloys of platinum and iridium. The feedthrough pin 3013 and the compressible electrical connection member 3021 may, of course, be fabricated from the same conductive material or even made as a single element.

The connector carriage utilizing fuzz button connectors is shown in FIGS. 43-46. The feedthrough pins 3013 and fuzz button contacts 3021 are separable components of each electrical conductive member. FIGS. 48-51 show highly preferred connector carriages comprising feedthrough pins and spring contacts that are welded together (by laser welding, for example).

As noted above, the lead connector assembly 3000 of FIG. 43 is depicted to accept two interposer seals 3009 each accommodating four electrical connections to each electrode lead 3005. The number of connections 3023 from a particular electrode lead 3005 is not limited to four, but is set by the chosen geometry of the electrode lead 3005. The lead connector assembly 3000 of this invention may be configured to connect to electrode leads having a much higher density of electrodes simply by designing the location or spacing of the electrical conductive members and interposer openings to conform with the number and spacing of the various electrode termini 3023.

The connector housing 3002 is typically assembled by aligning the clamp housing 3001 and the connector carriage 3007. Ancillary assembly design aids such as alignment posts 3015 on the connector carriage 3007 and matching holes (not shown) in the underside of the clamp housing 3001 help in aligning the connector carriage 3007 to the clamp housing 3001. Such alignment posts may be installed into mating holes or sockets in the connector carriage (or the connector housing) or may be formed integrally with the carriage or housing. The clamp housing 3001 and connector carriage 3007 may be secured together by the fastener 3003 once the one or more electrode leads 3005 are properly positioned in interposer 3009.

The fastener 3003 shown in FIG. 43 is a screw-type locking mechanism, which would desirably be pre-installed and captured in the clamp housing 3001 and is adapted to lock into a threaded hole found in the connector carriage 3007, sealing the electrode lead 3005 in place within the interposer 3009. The fastener 3003 may be made out of a biocompatible polymer or of a metal such as titanium. The head of the exemplified fastener 3003 shown in FIG. 43 is flush with the clamp housing 3001 and has a hexagonal opening for fastening and unfastening. The ability to reopen and adjust this lead connector assembly 3001 is an additional benefit of this invention. The fastener 3003 need not be a screw-type locking mechanism. Other fastener types—clips, Dzus-type closures, snap fasteners, integral helical joints allowing the clamp housing to twist into a closed position, clamps external to the clamp housing 3001, and other closing and fastening devices having the specified function apparent to the skilled worker—are within the ambit of this disclosure.

In practice, the inventive lead connector assembly 3000 may be assembled around the electrode leads 3005. The proximal end (or "connector end") of the depicted electrode lead 3005 has a number of proximal electrode contacts or termini 3023 that are shown in FIG. 43 to be ring-type. Each of those proximal contacts 3023 are in electrical contact with the distal lead electrodes implanted into the brain. The connector end of the electrode lead 3005 fits into the interposer 3009. The interposer 3009 may be made from any suitable biocompatible insulating material, such as a silicone (for example, MED4950 silicone from NuSil Technology), that is preferably elastomeric. The interposer 3009 includes an axial passageway to allow lengthwise entrance of the electrode lead 3005 and openings extending generally radially to the axial passageway that typically contain the electrical connection members 3021 discussed at length above. The physical and electrical contact between each proximal electrode contact 3023 of the electrode lead 3005 are thus made.

Figure 44A:
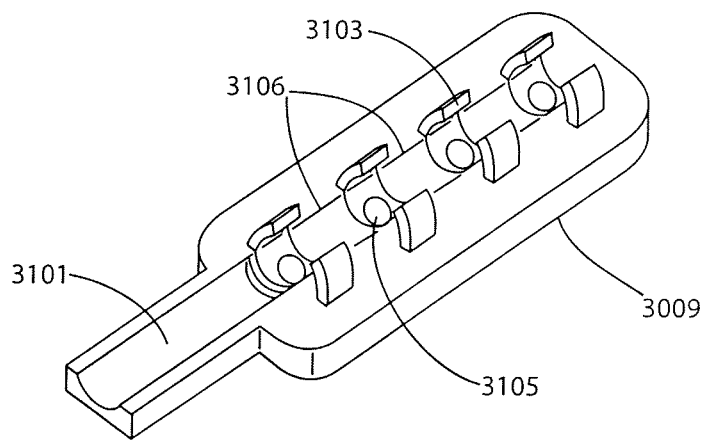
FIG. 44A is a perspective view of one variation of an interposer for holding fuzz button contacts.

FIGS. 44A, 44B, and 48A-48E show variations of the interposers. In FIG. 44A, the interposer 3009 has an axial passageway or channel 3101 and a series of bendable, but substantially rigid clips 3103 adapted to hold an electrode lead (e.g., electrode lead 3005 in FIG. 43) in place. This variation works especially well when the compressible electrical conductive members 3105 are fuzz buttons. The interposer 3009 holds electrical conductive members 3105 in the openings exposed to the electrical contacts of the electrode lead. There are many variations of the overall shape of the interposer 3009 of FIG. 44A that would also be effective. For example, rather than having rigid clips that are partially open to secure the electrode lead, the interposer could more completely enclose the electrode lead.

FIG. 44A also shows a number of seal surfaces 3106 that conform to the spacing between the various proximal electrode contacts 3023 on the electrode lead 3005 and form a portion of the seal isolating a specific electrode contact 3023 in a chamber-like opening. The corresponding portion forming the remainder of the seal wall may be seen as the saddle-like component 3008 found in the FIG. 46 depiction.

Figure 44B:
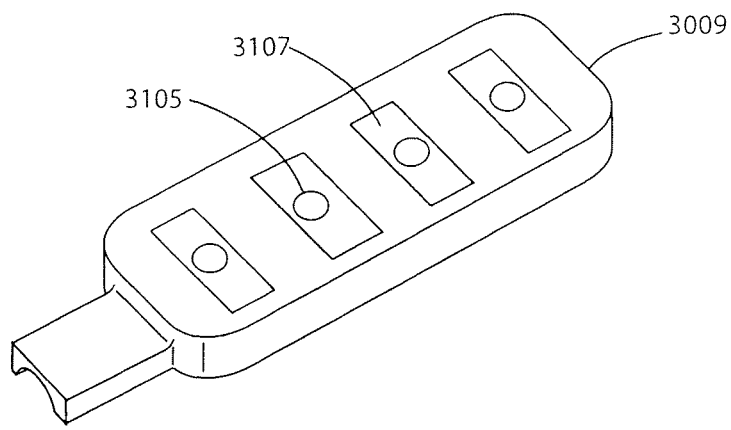
FIG. 44B is a perspective view of the interposer of FIG. 44A from the opposite side.

FIG. 44B illustrates the underside of the interposer 3009 shown in FIG. 44A. This side contacts the baseplate of the connector carriage 3007 as shown in FIG. 43. The compressible electrical conductive members 3105 extend through the interposer 3009 and are adapted to make electrical contact with the feedthrough pins 3013, shown in FIG. 43. The compressible electrical conductive members 3105 may be held in the openings of the interposer 3009 by various structures and adhesives.

Figure 45:
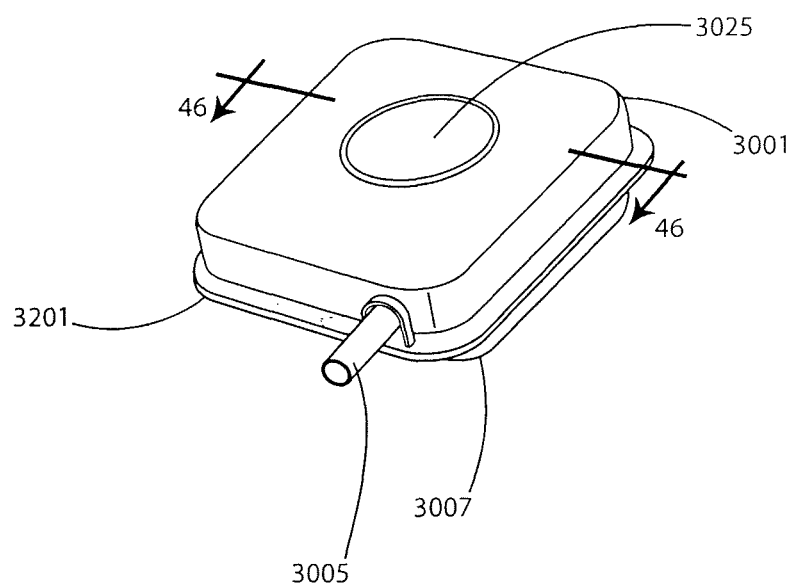
FIG. 45 is a perspective view of the fully assembled lead connector containing a single electrode lead.

FIG. 45 illustrates the assembled and sealed lead connector assembly 3000. After inserting the electrode lead 3005 into the interposer, the interposer is held between the clamp housing 3001 and connector carriage 3007. The fastener 3003 is engaged, locking the clamp housing 3001 to the connector carriage 3007, and making electrical contacts between the electrode contact of the electrode lead and the electrical conductive members (the fuzz button connector and the feedthrough pin). The fastener put the compressible fuzz button connector in compression against the electrode lead, and also seals each contact of the electrode lead within the interposer. It is within the scope of this invention that the interposer 3009 and its complementary section that fits above the portion shown in FIG. 44A within the clamp housing (all discussed elsewhere in more detail), may be detachable or removable from the connector assembly or, alternatively, those interposer seals may each be fixed (e.g., glued) respectively within clamp housing 3001 and connector carriage 3007. This is more thoroughly illustrated in FIG. 46.

Figure 46:
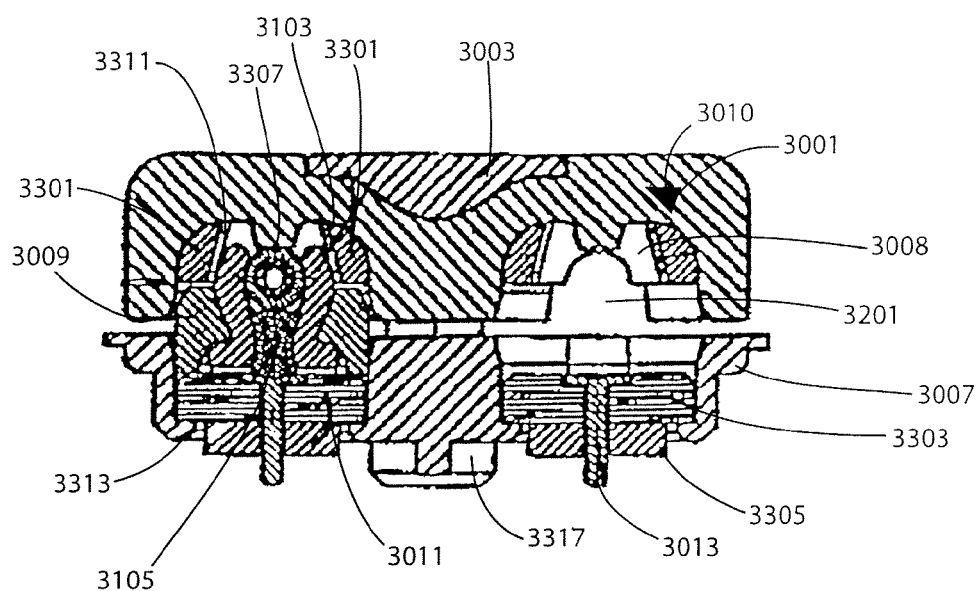
FIG. 46 is a cross-sectional view of a lead connector with fuzz button contacts taken along line A-A' of FIG. 45.

FIG. 46 shows a cross-section through the sealed lead connector assembly 3000 of FIG. 45 (at section line A'-A). The electrode lead is shown sectioned through an electrode contact 3307. With the fastener engaged, the electrical conductor member 3105 presses against the electrode contact 3307 and also against the first side of the feedthrough pin 3013. The feedthrough pin 3013 is shown to be slightly concave to maximize the common contact surface area between the electrical conductor member 3105 and the feedthrough pin 3013. This variation of the invention shows the feedthrough pin 3013 to be embedded in the baseplate 3011. As noted above, the baseplate 3011 is seated into and is hermetically attached to the base of the connector carriage 3007 and mates with the interposer 3009.

In the variation shown in FIG. 46, the baseplate 3011 has a ceramic layer 3303 that supports and insulates the feedthrough pins 3013 and a capacitive element 3305 that filters transients that are transmitted through the feedthrough pins 3013. The baseplate 3011 is held in the connector carriage 3007 and may be supported by an annular lip 3313 in the bottom of the depression into which the interposer 3009 resides.

The interposer 3009 is held in a recessed region of the connector carriage 3007, and the component rigid clips 3103 hold the electrode contact in position against the electrical conductor member 3105. A complementary ramp 3301 is situated inside a complementary upper interposer seal 3010, in turn within clamp housing 3001. The complementary ramp 3301 maintains the "arms" of the molded clip 3103 together and against the electrode lead. The complementary upper interposer seal 3010 secures the lead in place and promotes compressional contact between the electrical conductor member 3105 and that electrode lead. Adjacent ramps 3301 may be seen seal component 3008 portion of the complementary upper interposer seal 3010, mentioned above. This seal component 3008, in conjunction with the seal surfaces 3106 (in FIG. 44A), provides assurance that the non-common electrode contacts are fluid tight and electrically isolated from non-common adjacent electrode contacts. The surfaces variously of the seal and the interposer 3009 may be provided with a coating 3311 (for example, with PARYLENE) to prevent sticking or fusion adhesion amongst the seal 3008, the seal surface 3106 (FIG. 44A), the interposer 3009, and the electrode lead. The sealed lead connector assembly 3000 of FIGS. 45 and 46 are depicted to contain only one interposer and electrode lead. The space for a second lead 3201 is shown unoccupied.

Figure 47:
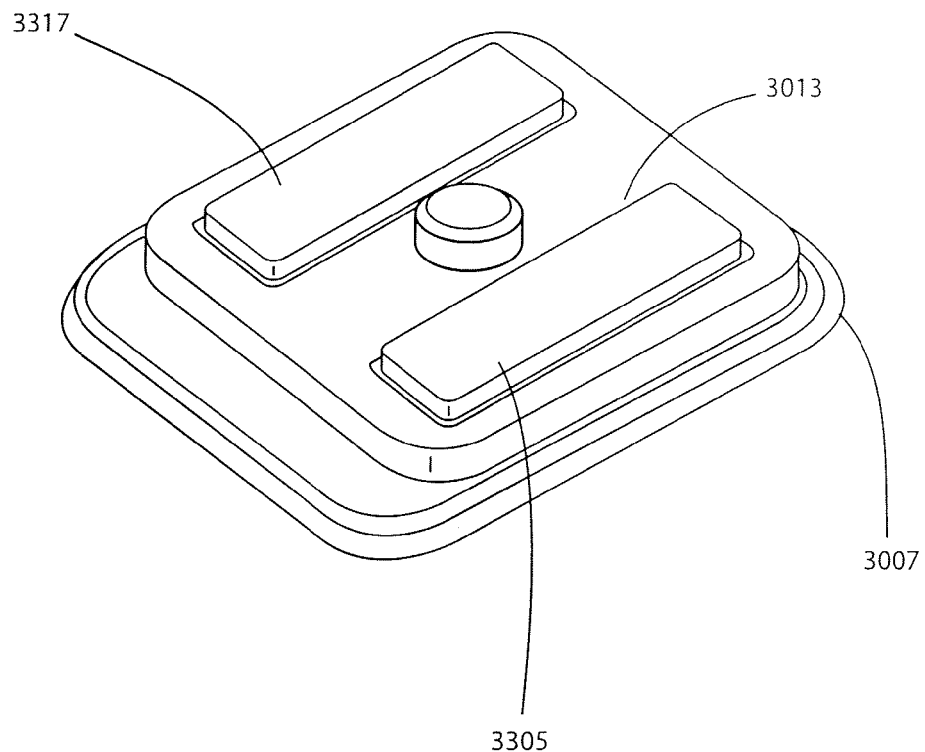
FIG. 47 is a perspective view of the opposite side of the connector carriage of FIG. 43.

FIG. 47 shows the exterior lower surface of the connector carriage 3007. The exterior layer of the capacitor element 3305 is shown. The most distant or second end of the feedthrough pins 3013 project externally above the outer layer of the capacitor element 3305 and is adapted to contact or otherwise to connect with an implantable device, such as a stimulator or signal processor. The cylindrical protrusion 3317 in this variation of the invention forms a complementary section of the fastener (3003 in FIG. 43) in that it houses a female threaded section when the fastener 3003 is a screw or a bolt. Other fastener pairs will mandate other complementary fastener components in the protrusion 3317. In this variation, the fastener screw threads into the connector carriage 3007. A locking nut or other locking mechanism, split ring, or crown washers may be employed to hold the fastener in place as eventually fastened, all as the designer sees fit. Furthermore, the shape of the protrusion 3317 and of the entire outer surface of the connector carriage 3007 may be designed to allow mating to or attachment of an implantable device. Of course, numerous attachment methods are suitable for the fastener, provided that the hermeticity of any attached implantable device is not compromised.

Figure 48A:
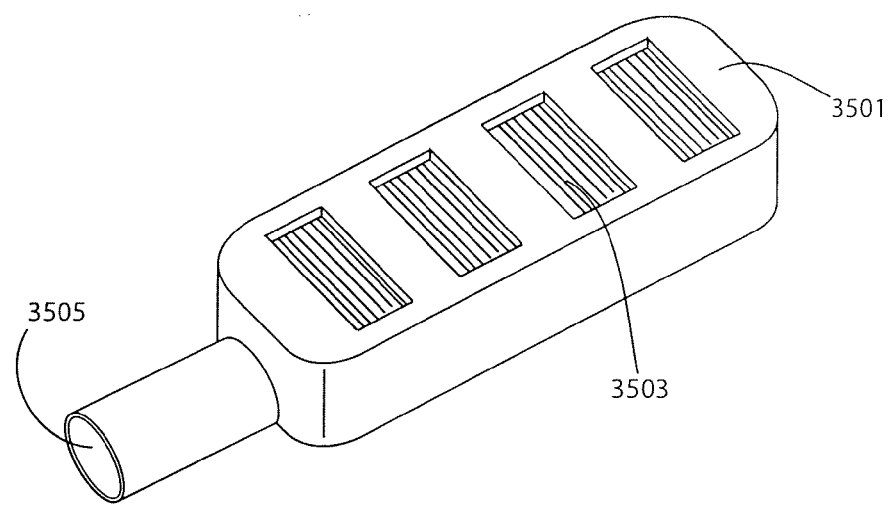
FIG. 48A is a perspective view of a variation of an interposer.

FIG. 48A shows a second, but preferred, variation of the interposer 3501 that works well when the electrical connection member 3503 is a spring contact. The connector end or terminal end of an electrode lead is inserted axially into the hollow channel 3505. The various openings in the interposer 3501 allow the spring contacts to enter the interposer 3501 and form an electrical connection with the proximal contacts of the electrode lead. It is desirable that the interposer 3501 be sized in such a way that when later inserted into the clamp housing (see, for instance, the depiction in FIG. 49A), the clamp housing squeezes the (preferably elastomeric) interposer 3501 and, in turn, squeezes the lead and retains both in an properly aligned condition for subsequent assembly into the completed inventive housing assembly. A "properly aligned condition" means that the proximal contacts of the electrode lead are aligned in position for later electrical continuity with the complementary portions of the inventive device, e.g., the electrode lead has not undertaken any axial or longitudinal movement with respect to the interposer. The use of the interposer to temporarily maintain various portions of the inventive device in practical subassemblies during a surgical procedure is applicable to other variations of the interposer discussed elsewhere in this specification. Indeed, it is within the scope of this invention to use other devices or assembly aids to hold various parts of the inventive device together during those surgical procedures.

FIG. 48B shows a perspective view of a variation of the interposer 3520 that is substantially closed, having only one opening, an axial passageway 3522, that is adapted to accept the proximal end of an electrode lead. In this variation, the compressible electric conductor members are conductive regions 3524 that match up with the spacings of the proximal contacts on an electrode lead. The interposer 3520 is desirably of a selection of polymers, preferably elastomers, adapted to create the differential conductivity. The conductive regions 3524 are surrounded by non-conductive areas or regions 3526 that allow isolation of the current flow from or to the electrode lead to the passthrough terminals discussed elsewhere. Construction of this variation via normal polymer molding techniques should be apparent to those of ordinary skill in this art. The spring clip and fuzz buttons discussed elsewhere are not necessary in this variation. Although the axial passageway or bore 3522 is shown to be smooth, other bore configurations are suitable, e.g., with projections, projecting rings, etc. The functions of contact and of sealing are to be accomplished by the structure, however. This variation fits into the connector carriage 3007 in the same way as do the other variations discussed elsewhere.

FIG. 48C shows a cross-section of the FIG. 48B interposer 3520. Shown are the conductive regions 3524 and the surrounding non-conductive areas or regions 3526 as well as the axial bore or passageway 3522. The interposer 3520 device is depicted to be symmetrical, although it need not be. The conductive regions 3524 may be situated on but one side of the interposer 3520 adjacent the passthrough terminals, although the installation in the housing must be made with more care.

FIG. 48D shows a perspective view of another variation of the interposer 3540 that comprises compressible electric conductor members that are conductive regions 3542 surrounded by a non-conductive region or regions 3544. This variation requires a separate cooperating upper shell to complete the seal portions shown in the axial passageway 3548. This axial passageway 3548 is adapted to accept the proximal end of an electrode lead. Again, the compressible electric conductor members are conductive regions 3542 that match up in physical spacing with the spacings of the proximal contacts on an electrode lead. This variation fits into the connector carriage 3007 in the same way as do the other variations discussed elsewhere.

FIG. 48E shows a cross-section of the FIG. 48D interposer 3540. Shown are the conductive regions 3542 and the surrounding non-conductive area or regions 3544 as well as the axial bore or passageway 3548.

Figure 49A:
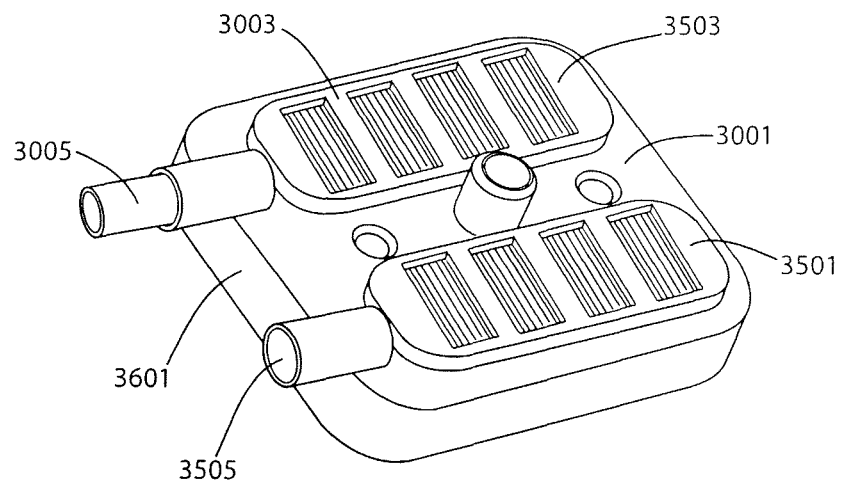
FIG. 49A is a perspective view of a clamp housing holding two interposers, one of which has an electrode lead inserted into it.
Figure 49B:
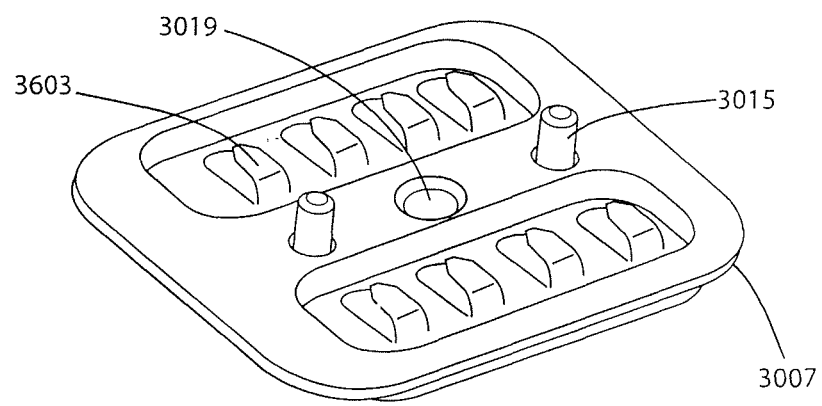
FIG. 49B is a perspective view of a variation of a connector carriage with spring contacts.

FIGS. 49A and 49B show placement of the interposer 3501, after insertion of the electrode lead 105 into that interposer, in turn into the connector carriage 3007 much in the same way as shown in FIGS. 43 and 46 above. The interposer 3501 is held in the clamp housing 3001. Alternatively, the clamp housing 3001 and the interposer 3501 may be integrated into a single structure. Additionally, the interposer may be preattached to the clamp housing 3001. An electrode lead 3005 is inserted into one of the interposers 3501. The connector carriage 3007 may be aligned with the clamp housing 3001 using optional alignment posts 3015 fitting into complementary holes 3601 on the clamp housing 3001. Combining the connector carriage 3007 with the clamp housing 3001 causes the spring electrical conductor members 3603 to enter the openings in the interposer 3503, and make an electrical contact with the electrode lead 3005. A fastener 3003 may be used to place compression on the spring electrical conductor members 3603 and to lock the connector carriage 3007 and the clamp housing 3001 together.

In this variation of the invention, the electrical connection members (the spring contacts) 3603 are welded to the proximal side of the feedthrough pins on the connector carriage (e.g., by laser spot welding). The spring contact can be made of a suitably springy, conductive, preferably inert metal or alloy (such as 80-20 Platinum-Iridium).

Figure 50:
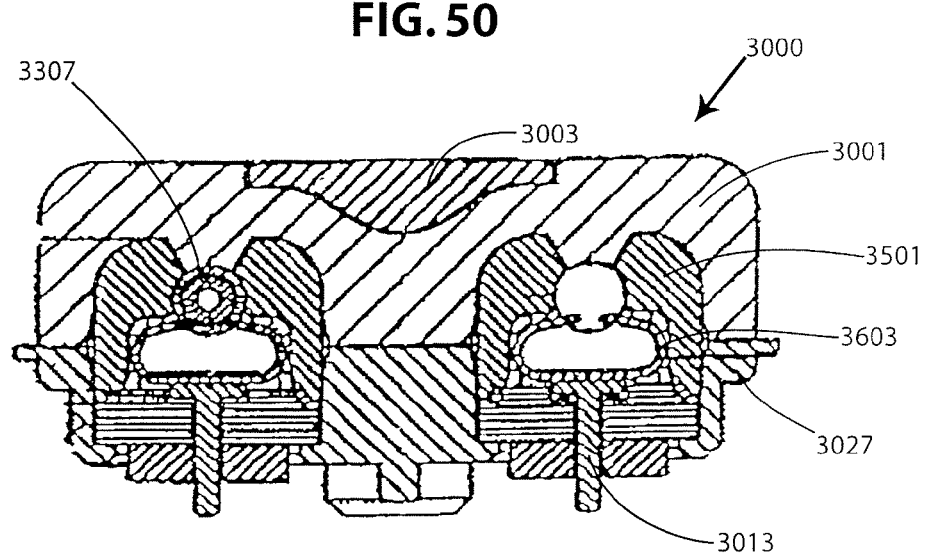
FIG. 50 is a cross-sectional view of the lead connector with spring contacts taken along line A-A' of FIG. 45.

FIG. 50 is another cross-section of the lead connector assembly 3000, this time showing the electrical connection members (the spring contacts) 3603 and the interposer 3501 of FIGS. 48, 49A, and 49B. The electrical connection members (the spring contacts) 3603 have been attached to the feedthrough pin 3013, perhaps by welding, and is in electrical contact with a proximal electrode or terminus of the electrode lead 3307. The clamp housing 3001 is locked onto the connector carriage 3007 using fastener 3003. This whole variation of the interposer also effectively seals the electrical contact between the electrode lead and the compressible electrical connection member from external fluids and from adjacent non-common electrical contacts and from any conductive portions of connector carriage 3007.

Figure 51A:
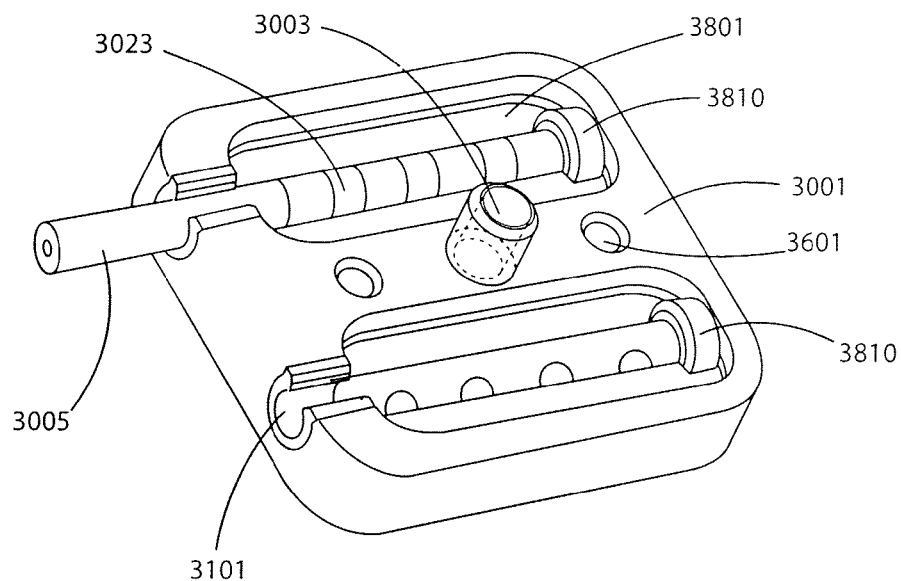
FIG. 51A is a perspective view of a clamp housing holding the top half of two split interposers, one holding an electrode lead.
Figure 51B:
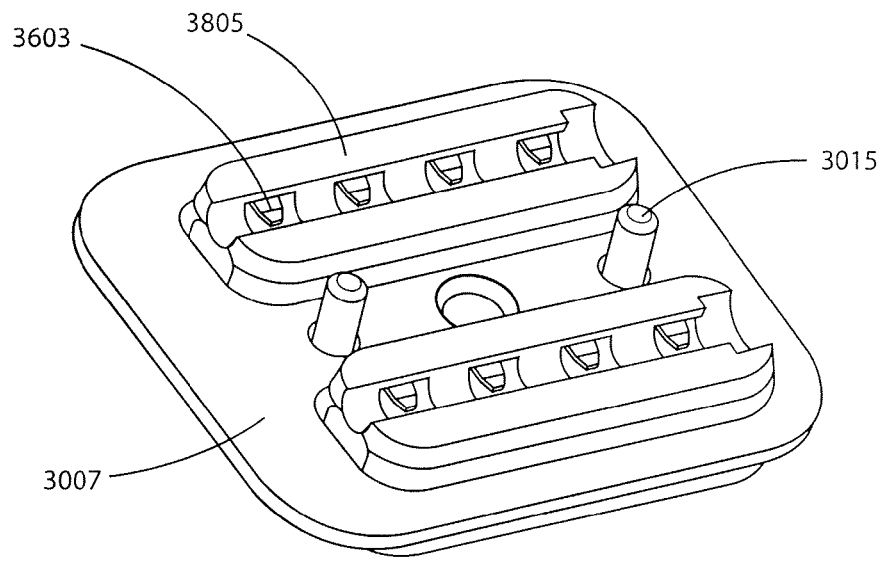
FIG. 51B is a perspective view of a variation of a connector carriage with spring contacts and the bottom halves of two split interposers.

FIGS. 51A and 51B show another variation of the interposer in which the interposer is split into an upper half 3801 (see FIG. 51A) and a lower half 3805 (see FIG. 51B). The upper half 3801 of the interposer is set in the clamp housing 3001. In FIG. 51A, the upper half 3801 of the interposer may be seen residing in a recessed portion of the clamp housing 3001. An electrode lead 3005 is shown seated in the channel of the upper half 3801. The proximal contacts or termini 3023 of the electrode lead 3005 are exposed in the view shown in FIG. 51A. The lower half 3805 of the interposer is attached to the lead positioners 3810 and has openings that fit the spring contacts 3603 attached to the feedthrough pins (not seen in this view). As noted above, the interposer upper half 3801 and lower half 3805 may each be produced in such a way as to be affixed permanently in the respective clamp housing 3001 and connector carriage 3007 or they may be made in such a way as to be removable. The alignment posts 3015 help join the clamp housing 3001 to the connector carriage, connecting the lower half 3805 of the interposer with the upper half 3801 of the interposer. The alignment posts 3015 in FIGS. 51A and 51B (just as in FIG. 43) project from the connector carriage into the clamp housing 3001. However, alternatively, the alignment posts may just as well project from the clamp housing 3001 into the connector carriage 3007. Alternatively, alignment pins may be completely separate elements.

One other desirable feature is the presence of one or more lead positioners 3810 such as are shown in FIG. 51A. In this depiction, the lead positioners 3810 are situated in the clamp housing 3001. This hooped variation of the lead positioner 3810 allows a user physician to situate the lead 3005 into the clamp housing 3001 and be sure that lead 3005 is properly positioned so that as the clamp housing 3001 is later placed onto the connector carriage 3007, the proximal contacts 3023 on the lead 3005 are properly indexed onto the spring contacts 3803. Additionally, this arrangement allows sequential assembly of the inventive device in the operating room and makes fewer the number of parts the physician must coordinate at any one time during that assembly.

Finally, fastening the fastener 3003 puts the spring electrical conductor members 3803 in compression against the electrode contacts and ensures electrical connections between the spring contacts 3603 and the electrode contacts 3023 on the electrode lead.

The present application thus provides medical electrical leads that have reinforced constructions to overcome the disadvantages associated with conventional medical electrical leads. More specifically, the present medical electrical leads have reinforced proximal and distal portions to enhance the rigidity of these lead portions and to also disperse stress away from the distal and proximal ends of the lead where a distalmost electrode and a proximalmost lead connection terminal, respectively, reside. This results in an improved conductive interface between the distalmost electrode and the conductor and the proximalmost lead connection and the conductor and also greatly reduces or eliminates the likelihood that the electrode or lead connection terminal can become completely dislodged from the lead body.

It should be observed that while the foregoing detailed description of various embodiments of the present invention is set forth in some detail, the invention is not limited to those details and an implantable medical electrical lead made or used according to the invention can differ from the disclosed embodiments in numerous ways. In particular, it will be appreciated that embodiments of the present invention may be employed in many different applications for sensing or stimulation, not just in the brain. Leads according to the invention may have utility in connection with peripheral nerves, muscles, other portions of the body, and other applications. Hence, the appropriate scope hereof is deemed to be in accordance with the claims set forth below.

What is claimed is:

1. A method of fabricating a reinforced medical electrical lead, the method comprising:
   providing at least one conductor;
   disposing a flexible shaft around the at least one conductor, the at least one conductor having first and second end sections that extend beyond ends of the flexible shaft;
   electrically connecting at least one lead connection terminal to the second end section of the at least one conductor;
   providing a first longitudinal reinforcing sheath, the first reinforcing sheath defining a first longitudinal lumen;
   inserting a section of a core member within the first longitudinal lumen at a distal end of the first reinforcing sheath;
   disposing a reinforcing sleeve around a length of the reinforcing sheath, the reinforcing sleeve surrounding the inserted section of the core member;
   compressing selected sections of the reinforcing sleeve around the first reinforcing sheath and the inserted section of the core member to enhance the rigidity at the distal end and retain the core member in place;
   disposing the crimped first reinforcing sheath through an inner channel defined by the first end section of the at least one conductor; and
   extending the flexible shaft so that the at least one conductor and the at least one lead connection terminal are at least partially embedded within the flexible shaft.

2. The method of claim 1, wherein disposing the crimped first reinforcing sheath through an inner channel defined by the first end section of the at least one conductor results in the at least one conductor being helically arranged around the first reinforcing sheath.

3. The method of claim 1, further comprising:
   providing a second longitudinal reinforcing sheath, the second reinforcing sheath defining a second longitudinal lumen;
   coupling a proximal end of the second reinforcing sheath to a bushing having a longitudinal bore extending therethrough and in communication with the second longitudinal lumen; and
   disposing the second longitudinal reinforcing sheath through the inner channel of the at least one conductor at the second end section thereof.

4. The method of claim 3, further comprising:
   disposing a proximal reinforcing element between the at least one lead connection terminal and the bushing.

5. The method of claim 4, wherein the proximal reinforcing element comprises an elongated reinforcing cable formed of arranged fibers, and the method further includes:
   wrapping and retaining the reinforcing cable around the bushing within a radial groove formed therein and disposing the reinforcing cable within an axial slot formed in the bushing substantially perpendicular to the radial groove, the reinforcing cable serving to enhance the robustness of the proximal portion.

6. The method of claim 1, further comprising:
   molding a relatively rigid distal tip around a head of the core member that extends beyond the distal end of the first reinforcing element.

7. The method of claim 1, further comprising electrically connecting at least one electrode to the first end section of the at least one conductor, and wherein extending the flexible shaft includes:
   injecting a material around the at least one electrode and the at least one lead connection terminal in a mold such that the length of the tubular shaft is extended to surround the first and second end sections of the at least one conductor, resulting in the at least one electrode and the at least one lead connection terminal being partially embedded in the extended flexible shaft.

* * * * *